US012220451B2

(12) United States Patent
Gunn et al.

(10) Patent No.: US 12,220,451 B2
(45) Date of Patent: Feb. 11, 2025

(54) CELL-BASED VACCINE COMPOSITIONS AND METHODS OF USE

(71) Applicant: Duke University, Durham, NC (US)

(72) Inventors: Michael D. Gunn, Durham, NC (US); Min-Nung Huang, Durham, NC (US)

(73) Assignee: Duke University, Durham, NC (US)

( * ) Notice: Subject to any disclaimer, the term of this patent is extended or adjusted under 35 U.S.C. 154(b) by 123 days.

(21) Appl. No.: 16/075,830

(22) PCT Filed: Feb. 3, 2017

(86) PCT No.: PCT/US2017/016362
§ 371 (c)(1),
(2) Date: Aug. 6, 2018

(87) PCT Pub. No.: WO2017/136633
PCT Pub. Date: Aug. 10, 2017

(65) Prior Publication Data
US 2019/0381158 A1    Dec. 19, 2019

Related U.S. Application Data

(60) Provisional application No. 62/291,086, filed on Feb. 4, 2016.

(51) Int. Cl.
*A61K 39/00* (2006.01)
*A61K 35/15* (2015.01)
*A61K 45/06* (2006.01)

(52) U.S. Cl.
CPC ...... *A61K 39/001156* (2018.08); *A61K 35/15* (2013.01); *A61K 2039/5158* (2013.01); *A61K 2039/876* (2018.08); *A61K 45/06* (2013.01)

(58) Field of Classification Search
None
See application file for complete search history.

(56) References Cited

U.S. PATENT DOCUMENTS

| | | | | |
|---|---|---|---|---|
| 8,383,665 B2 * | 2/2013 | Watson | ............... | A61K 31/7028 514/412 |
| 10,617,749 B1 * | 4/2020 | Hanks | ..................... | A61K 45/06 |
| 10,925,944 B2 * | 2/2021 | De Vries | ................ | A61K 35/15 |
| 2005/0158328 A1 | 7/2005 | Karlsson-Parra | | |
| 2008/0187559 A1 | 8/2008 | Kitabwalla | | |
| 2014/0037606 A1 * | 2/2014 | Amiel | .................. | C12N 5/0639 424/93.71 |
| 2014/0141046 A1 * | 5/2014 | Karlsson-Parra | .... | C12N 5/0645 424/277.1 |
| 2020/0101147 A1 * | 4/2020 | Zeng | ........................ | A61P 37/04 |
| 2021/0038702 A1 * | 2/2021 | De Vries | ................ | A61K 35/15 |

FOREIGN PATENT DOCUMENTS

| | | | |
|---|---|---|---|
| CN | 1951499 | * | 10/2006 |
| EP | 0979284 B2 | | 2/2000 |

OTHER PUBLICATIONS

Laborde et al., Frontiers in Immunology 2014, v.5 1-5.*
Srivastava S, et al. Cell-to-cell transfer of M. tuberculosis antigens optimizes CD4 T cell priming. Cell Host Microbe. 2014;15(6):741-52.
Thery C, et al. Membrane vesicles as conveyors of immune responses. Nature reviews Immunology. 2009;9(8):581-93.
Thurner B, et al. Generation of large numbers of fully mature and stable dendritic cells from leukapheresis products for clinical application. J Immunol Methods 1999, 223(1): 1-15.
Tivnan A, et al. Advances in immunotherapy for the treatment of glioblastoma. J Neurooncol. 2016.
Tolley, J. O., et al. "A high-yield, high-purity elutriation method for preparing human granulocytes demonstrating enhanced experimental lifetimes." Journal of leukocyte biology 42.1 (1987): 43-50.
Van Elsas A, et al. Elucidating the autoimmune and antitumor effector mechanisms of a treatment based on cytotoxic T lymphocyte antigen-4 blockade in combination with a B16 melanoma vaccine: comparison of prophylaxis and therapy. J Exp Med. 2001;194(4):481-9.
Wimmers F, et al. Paradigm Shift in Dendritic Cell-Based Immunotherapy: From in vitro Generated Monocyte-Derived DCs to Naturally Circulating DC Subsets. Front Immunol. 2014;5:165.
Xu Y, et al. Macrophages transfer antigens to dendritic cells by releasing exosomes containing dead-cell-associated antigens partially through a ceramide-dependent pathway to enhance CD4(+) T-cell responses. Immunology. 2016;149(2):157-71.
Zhang Y, et al. Microparticles released by Listeria monocytogenes-infected macrophages are required for dendritic cell-elicited protective immunity. Cell Mol Immunol. 2012;9(6):489-96.
Allan RS, et al. Migratory dendritic cells transfer antigen to a lymph node-resident dendritic cell population for efficient CTL priming. Immunity. 2006;25(1):153-62.
Andersen BM, et al. Increasing the efficacy of tumor cell vaccines by enhancing cross priming. Cancer Lett. 2012;325(2):155-64.
Backer R, et al. Effective collaboration between marginal metallophilic macrophages and CD8+ dendritic cells in the generation of cytotoxic T cells. Proc Natl Acad Sci U S A. 2010;107(1):216-21.
Balboa L, et al. Monocyte-derived dendritic cells early exposed to *Mycobacterium tuberculosis* induce an enhanced T helper 17 response and transfer mycobacterial antigens. Int J Med Microbiol. 2016;306(7):541-53.
Belz GT, et al. Cutting edge: conventional CD8 alpha+ dendritic cells are generally involved in priming CTL immunity to viruses. J Immunol. 2004; 172(4):1996-2000.

(Continued)

*Primary Examiner* — Michail A Belyavskyi
(74) *Attorney, Agent, or Firm* — Quarles & Brady, LLP

(57) ABSTRACT

Methods of generating an autologous cellular vaccine comprising monocytes or neutrophils and an antigenic polypeptide or nucleotide encoding the antigenic polypeptide are provided. The antigen-loaded cell-based vaccine compositions made using these methods are also provided. Methods of using the antigen-loaded cell-based vaccine compositions are also provided and these vaccines may be used to treat cancer. Kits for carrying out the methods described herein are also provided.

17 Claims, 28 Drawing Sheets

Specification includes a Sequence Listing.

(56) References Cited

OTHER PUBLICATIONS

Berger TG, et al. Efficient elutriation of monocytes within a closed system (Elutra) for clinical-scale generation of dendritic cells. J Immunol Methods 2005, 298(1-2): 61-72.
Cawood R, et al. Recombinant viral vaccines for cancer. Trends Mol Med. 2012;18(9):564-74.
Chiang CL, et al. Whole Tumor Antigen Vaccines: Where Are We? Vaccines (Basel). 2015;3(2):344-72.
Daniels GA, et al. A simple method to cure established tumors by inflammatory killing of normal cells. Nat Biotechnol 2004, 22(9): 1125-1132.
Davies LC, et al. Tissue-resident macrophages. Nat Immunol. 2013;14(10):986-95.
Den Haan JM, et al. CD8(+) but not CD8(-) dendritic cells cross-prime cytotoxic T cells in vivo. J Exp Med. 2000;192(12):1685-96.
FDA. Dendreon PROVENGE. Product Info. Revised Oct. 2014. 19 pages.
Fehres CM, et al. Understanding the biology of antigen cross-presentation for the design of vaccines against cancer. Front Immunol. 2014;5:149.
Gehring AJ, et al. Mobilizing monocytes to cross-present circulating viral antigen in chronic infection. J Clin Invest. 2013;123(9):3766-76.
Geissmann F, et al. Blood monocytes consist of two principal subsets with distinct migratory properties. Immunity. 2003;19(1):71-82.
Gudmundsdottir H, et al. Dynamics and requirements of T cell clonal expansion in vivo at the single-cell level: effector function is linked to proliferative capacity. J Immunol. 1999;162(9):5212-23.
Helft J, et al. GM-CSF Mouse Bone Marrow Cultures Comprise a Heterogeneous Population of CD11c(+)MHCII(+) Macrophages and Dendritic Cells. Immunity. 2015;42(6):1197-211.
Inaba K, et al. Isolation of dendritic cells. Current protocols in immunology / edited by John E Coligan [et al]. 2001; Chapter 3:Unit 3 7.
International Searching Authority. International Search Report and Written Opinion for application PCT/US2017/016362. Mailed on Apr. 21, 2017.
Jakubzick C, et al. Minimal differentiation of classical monocytes as they survey steady-state tissues and transport antigen to lymph nodes. Immunity. 2013;39(3):599-610.
Jung S, et al. In vivo depletion of CD11c+ dendritic cells abrogates priming of CD8+ T cells by exogenous cell-associated antigens. Immunity. 2002;17(2):211-20.
Kajimoto T, et al. Ongoing activation of sphingosine 1-phosphate receptors mediates maturation of exosomal multivesicular endosomes. Nature communications. 2013;4:2712.
Kim S, et al. Monocyte enrichment from leukapheresis products by using the Elutra cell separator. Transfusion. 2007;47(12):2290-6.
Klebanoff CA, et al. Therapeutic cancer vaccines: are we there yet? Immunol Rev. 2011;239(1):27-44.
Kumai T, et al. Peptide vaccines in cancer-old concept revisited. Curr Opin Immunol. 2016;45:1-7.
Kurts C, et al. Cross-priming in health and disease. Nature reviews Immunology. 2010;10(6):403-14.
Le Borgne M, et al. Dendritic cells rapidly recruited into epithelial tissues via CCR6/CCL20 are responsible for CD8+ T cell crosspriming in vivo. Immunity. 2006;24(2):191-201.

Lin KL, et al. CCR2-antagonist prophylaxis reduces pulmonary immune pathology and markedly improves survival during influenza infection. J Immunol. 2011;186(1):508-15.
Mazzini E, et al. Oral tolerance can be established via gap junction transfer of fed antigens from CX3CR1(+) macrophages to CD103(+) dendritic cells. Immunity. 2014;40(2):248-61.
Mendoza-Naranjo A, et al. Functional gap junctions facilitate melanoma antigen transfer and cross-presentation between human dendritic cells. J Immunol. 2007;178(11):6949-57.
Mitchell DA, et al. Tetanus toxoid and CCL3 improve dendritic cell vaccines in mice and glioblastoma patients. Nature 2015, 519(7543): 366-369.
Nair S, et al. Isolation and generation of human dendritic cells. Current protocols in immunology / edited by John E Coligan [et al]. 2012;Chapter 7:Unit7 32.
Nakano, H., et al. "Blood-derived inflammatory dendritic cells in lymph nodes stimulate acute T helper type 1 immune responses." Nature immunology 10.4 (2009): 394-402.
Neijssen J, et al. Cross-presentation by intercellular peptide transfer through gap junctions. Nature. 2005;434(7029):83-8.
Oh T, et al. Immunocompetent murine models for the study of glioblastoma immunotherapy. J Transl Med. 2014;12:107.
Oviedo-Orta E, et al. Gap junctions and connexin-mediated communication in the immune system. Biochimica et biophysica acta. 2004;1662(1-2):102-12.
Palucka K, et al. Cancer immunotherapy via dendritic cells. Nat Rev Cancer. 2012;12(4):265-77.
Phua KK, et al. Whole Blood Cells Loaded with Messenger RNA as an Anti-Tumor Vaccine. Adv Healthc Mater. 2013.
Qu C, et al. MHC class I/peptide transfer between dendritic cells overcomes poor cross-presentation by monocyte-derived APCs that engulf dying cells. J Immunol. 2009;182(6):3650-9.
Randolph GJ, et al. Antigen presentation by monocytes and monocyte-derived cells. Curr Opin Immunol. 2008;20(1):52-60.
Russo V, et al. Lymphocytes genetically modified to express tumor antigens target DCs in vivo and induce antitumor immunity. J Clin Invest. 2007;117(10):3087-96.
Saccheri F, et al. Bacteria-induced gap junctions in tumors favor antigen cross-presentation and antitumor Immunity. Science translational medicine. 2010;2(44):44ra57.
Samstein M, et al. Essential yet limited role for CCR2(+) inflammatory monocytes during *Mycobacterium tuberculosis*-specific T cell priming. Elife. 2013;2:e01086.
Sanchez-Perez L, et al. Potent selection of antigen loss variants of B16 melanoma following inflammatory killing of melanocytes in vivo. Cancer Res 2005, 65(5): 2009-2017.
Schreiber HA, et al. Intestinal monocytes and macrophages are required for T cell polarization in response to Citrobacter rodentium. J Exp Med. 2013;210(10):2025-39.
Schumacher T, et al. A vaccine targeting mutant IDH1 induces antitumour immunity. Nature. 2014;512(7514):324-7.
Sharma P, et al. Immune Checkpoint Targeting in Cancer Therapy: Toward Combination Strategies with Curative Potential. Cell. 2015;161(2):205-14.
Signori E, et al. DNA vaccination strategies for anti-tumour effective gene therapy protocols. Cancer Immunol Immunother. 2010;59(10):1583-91.
Soudja SM, et al. Inflammatory monocytes activate memory CD8(+) T and innate NK lymphocytes independent of cognate antigen during microbial pathogen invasion. Immunity. 2012;37(3):549-62.
SQZ Biotechnologies. SQZ Biotech Expands Cell Therapy Partnership with Roche to Develop Antigen Presenting Cells for Immune-Oncology. Press Release dated Oct. 15, 2018.

\* cited by examiner

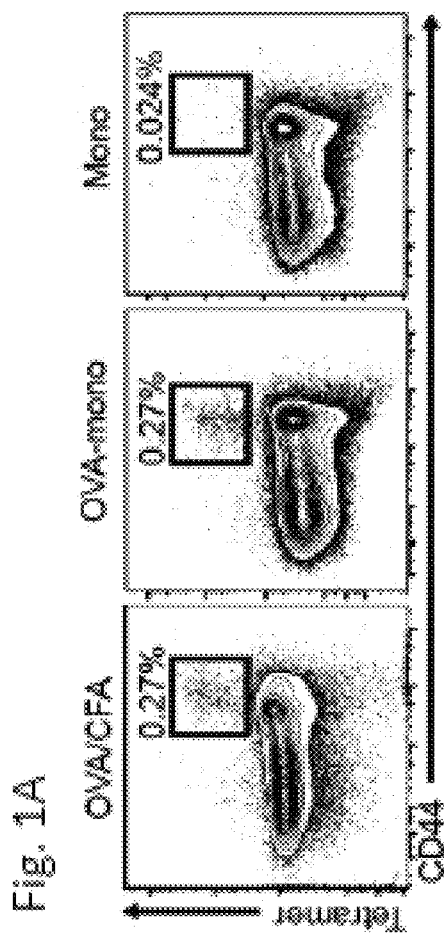
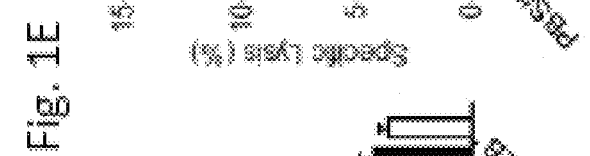
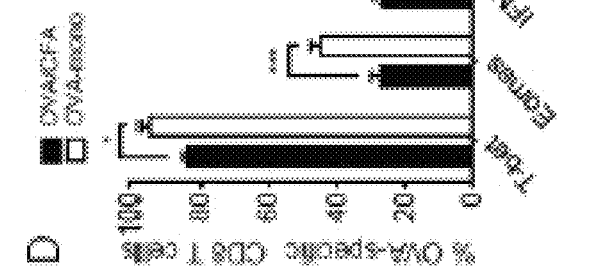
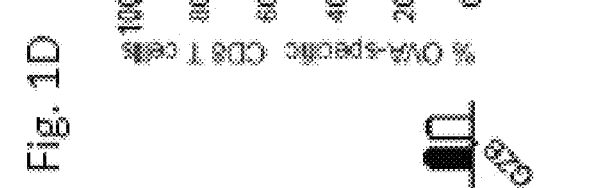
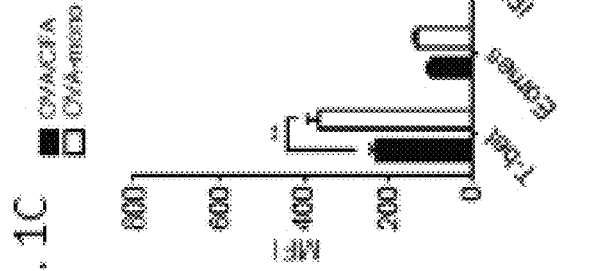
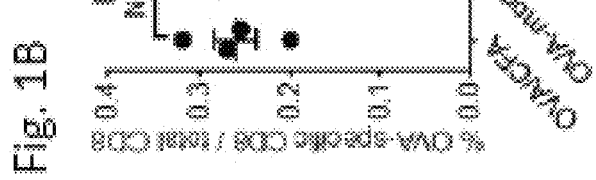

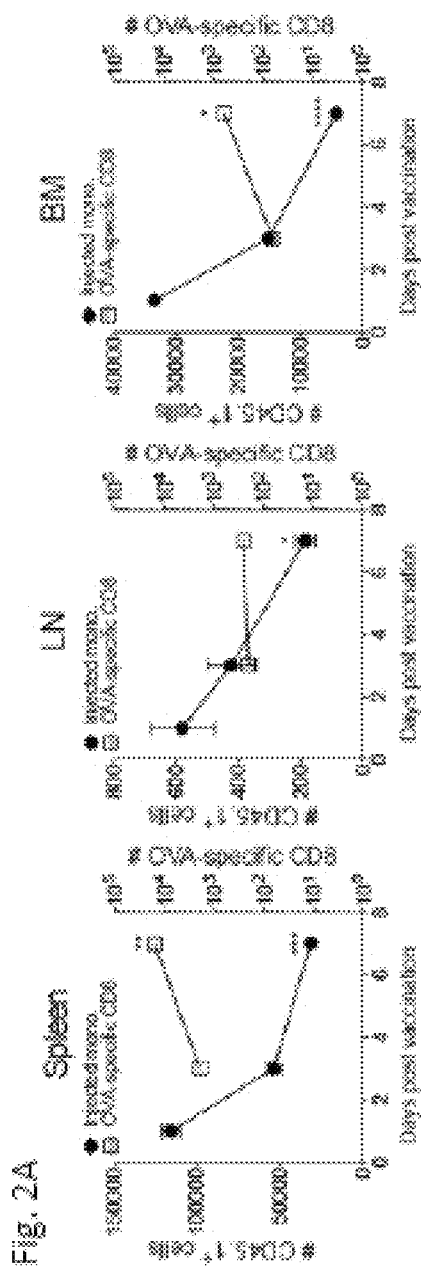
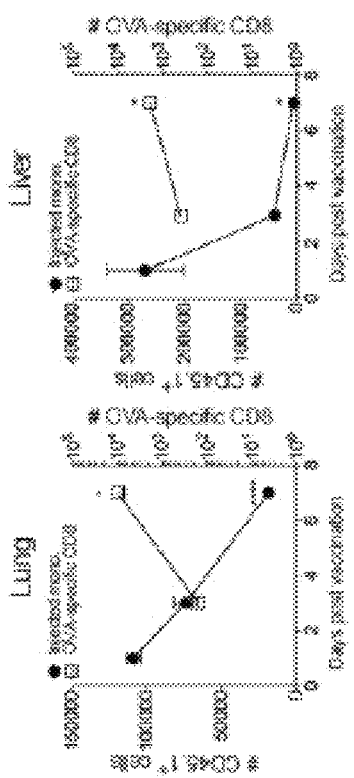
Fig. 2A / Fig. 2A (cont.)
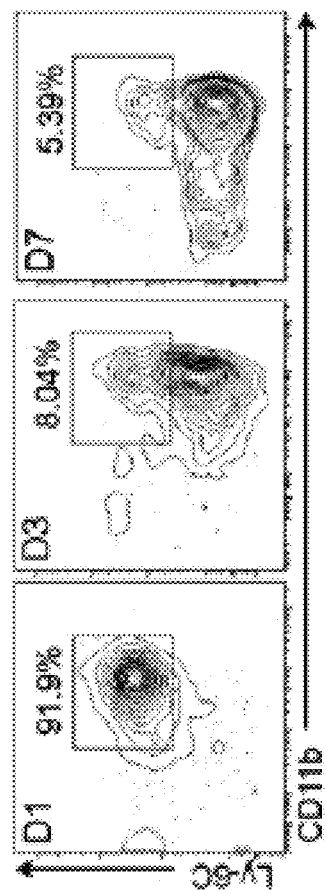
Fig. 2B

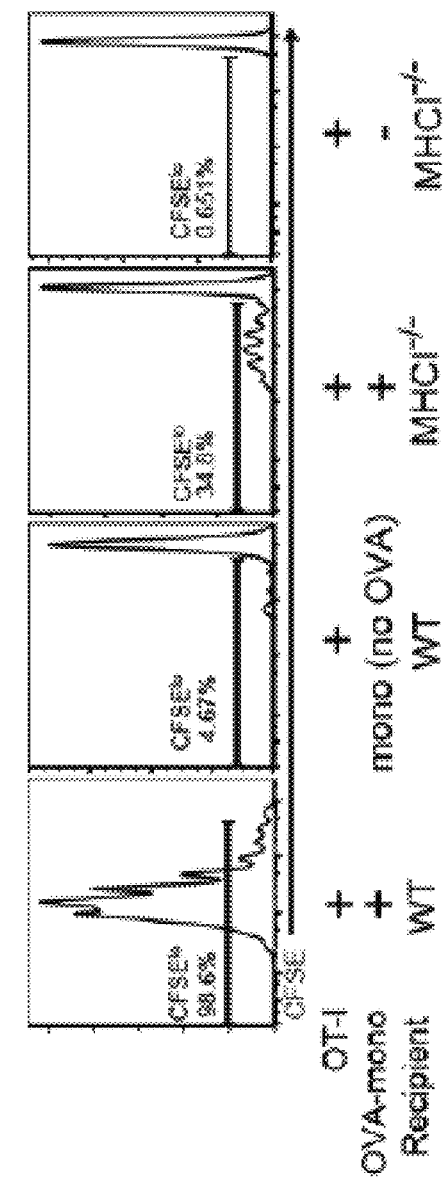
Fig. 3A
Fig. 3B
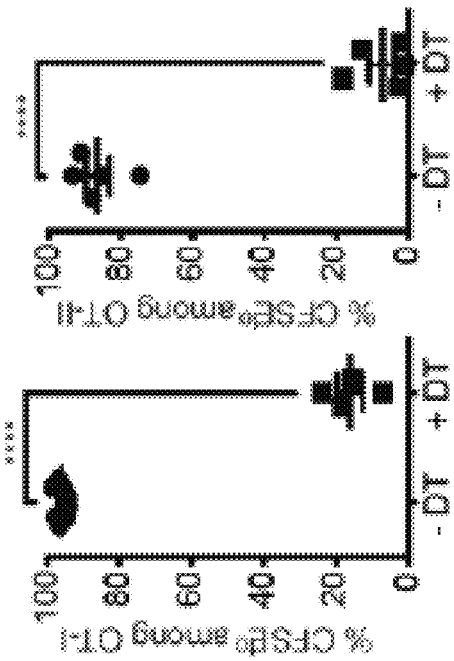
Fig. 3D
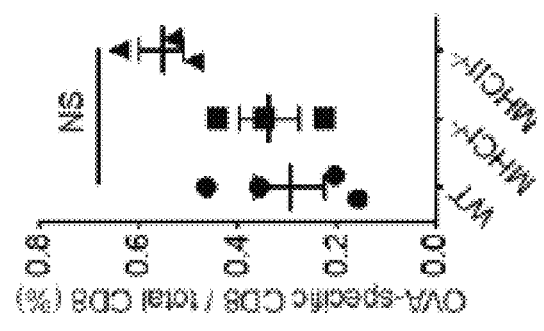
Fig. 3C
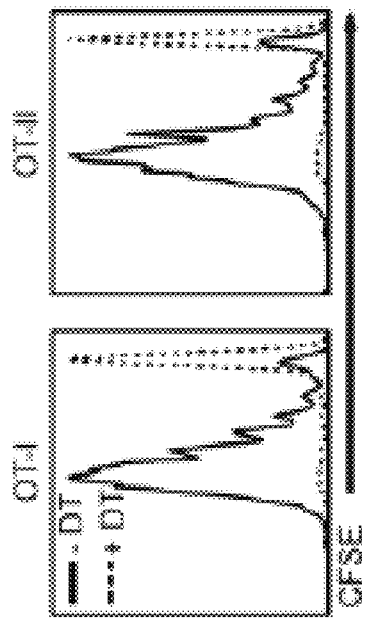

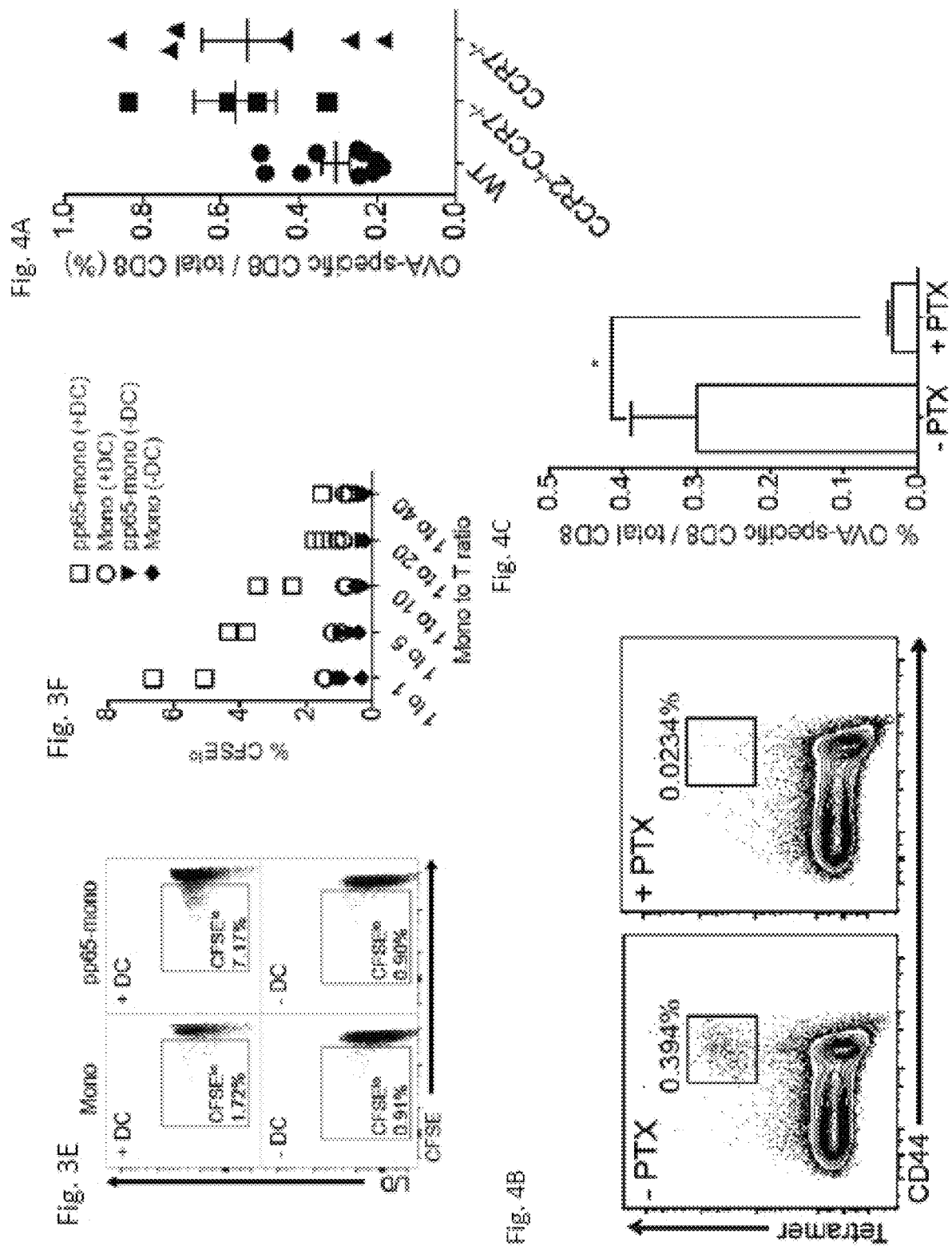

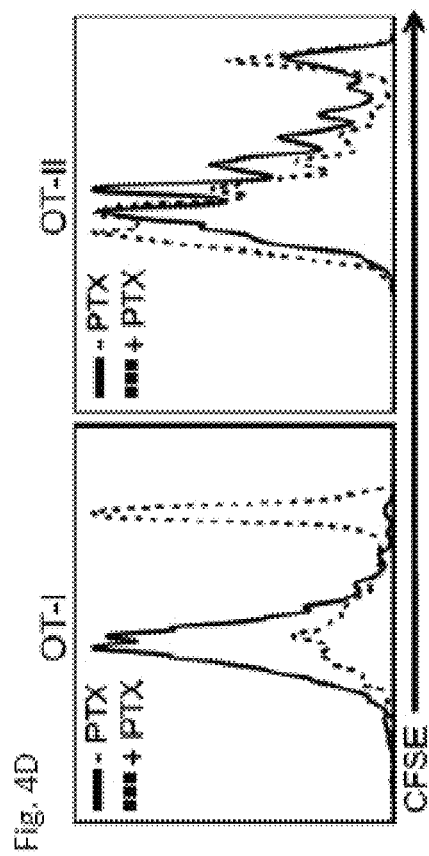
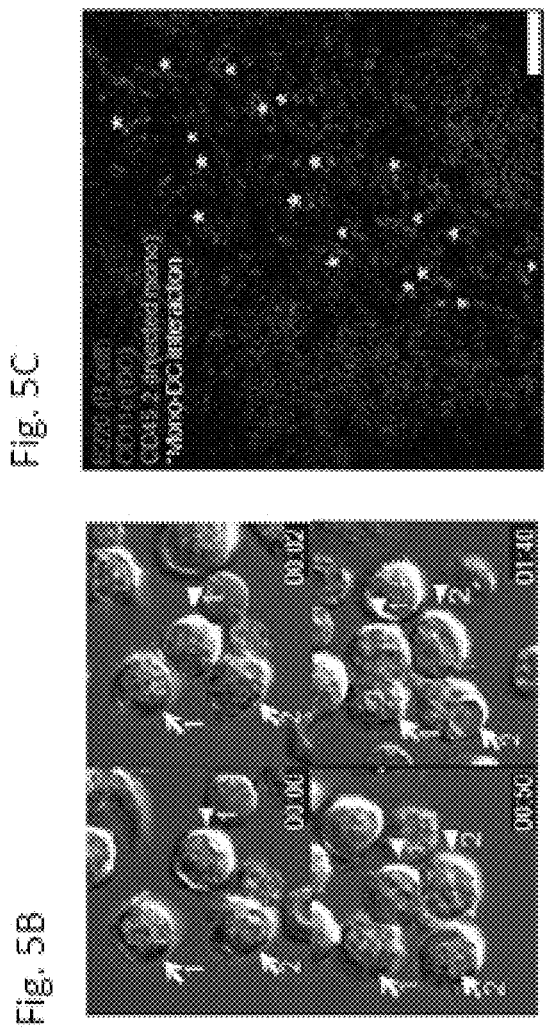
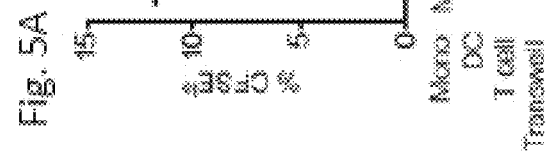

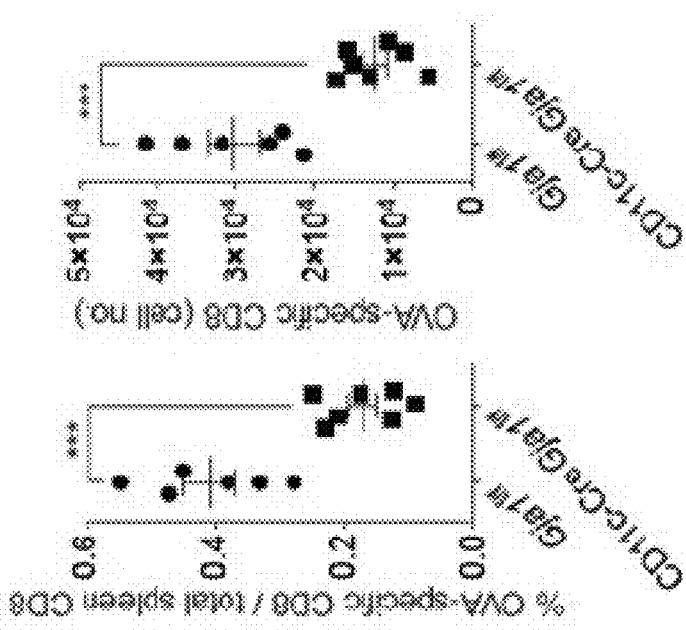
Fig. 5J
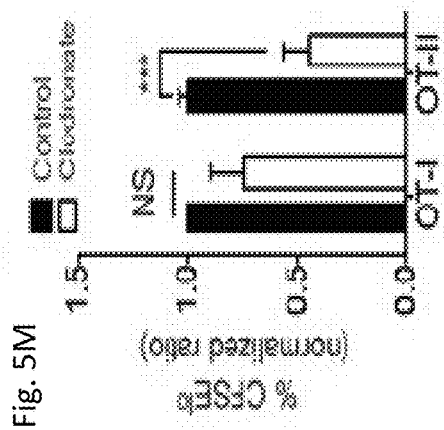
Fig. 5M
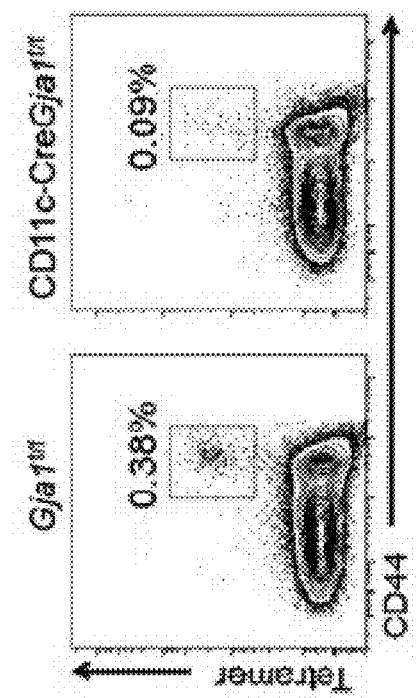
Fig. 5I
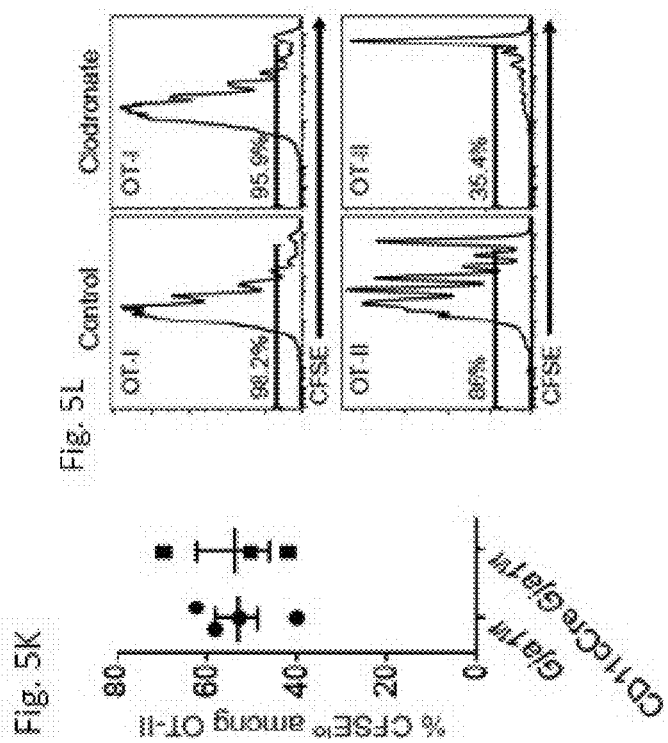
Fig. 5L
Fig. 5K

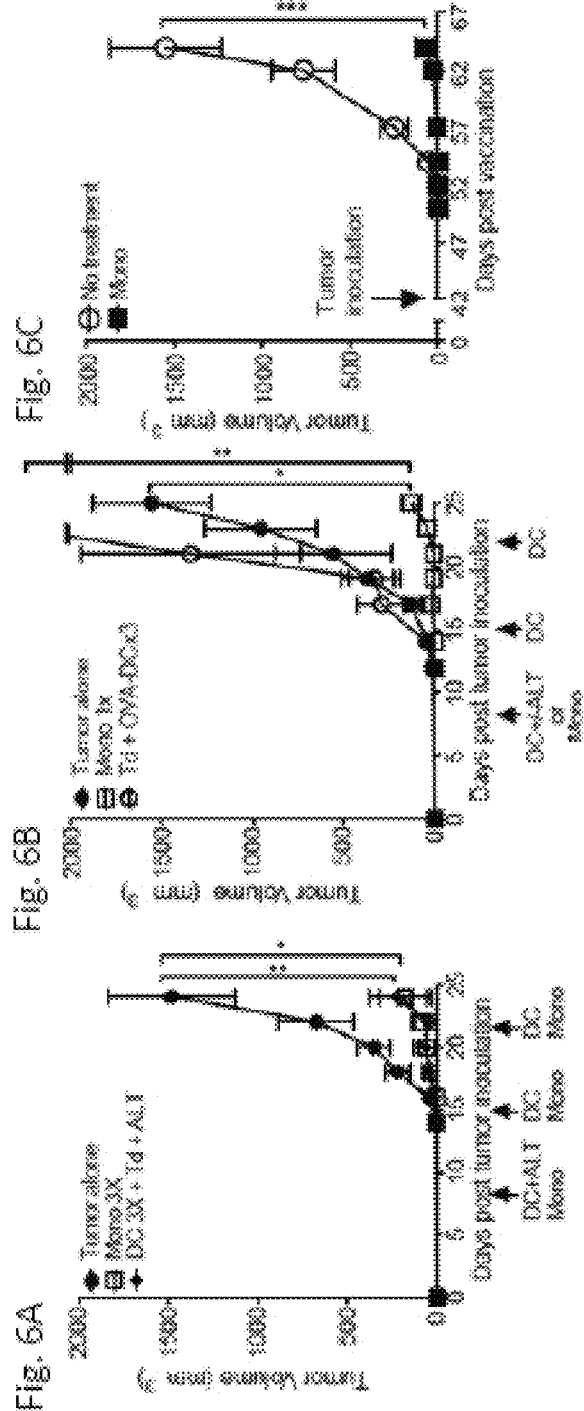
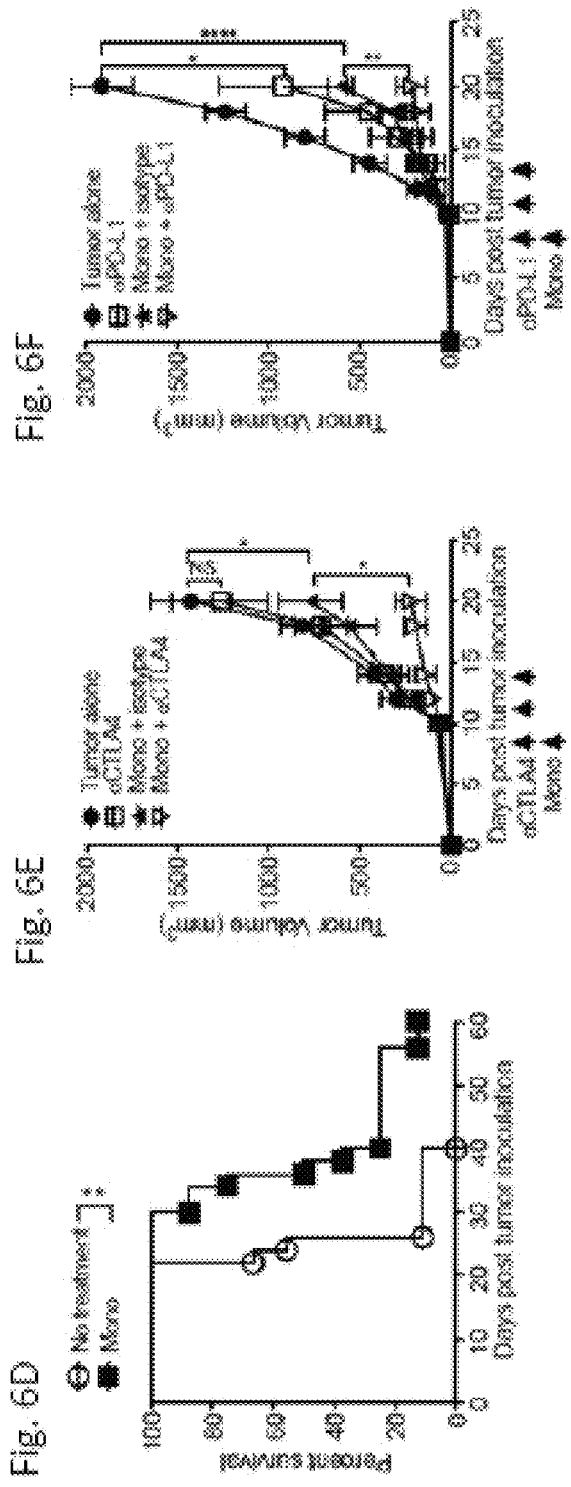
Fig. 6A
Fig. 6B
Fig. 6C
Fig. 6D
Fig. 6E
Fig. 6F

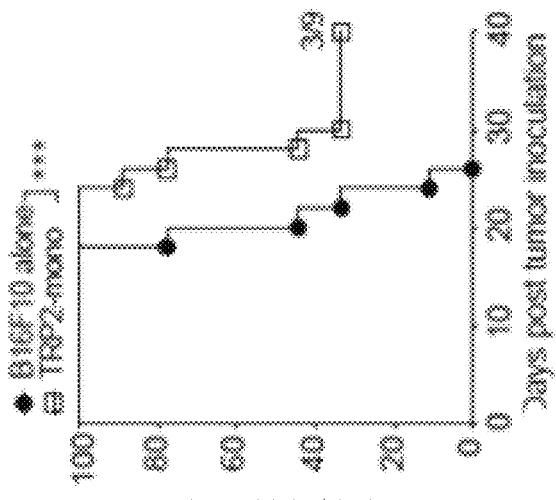
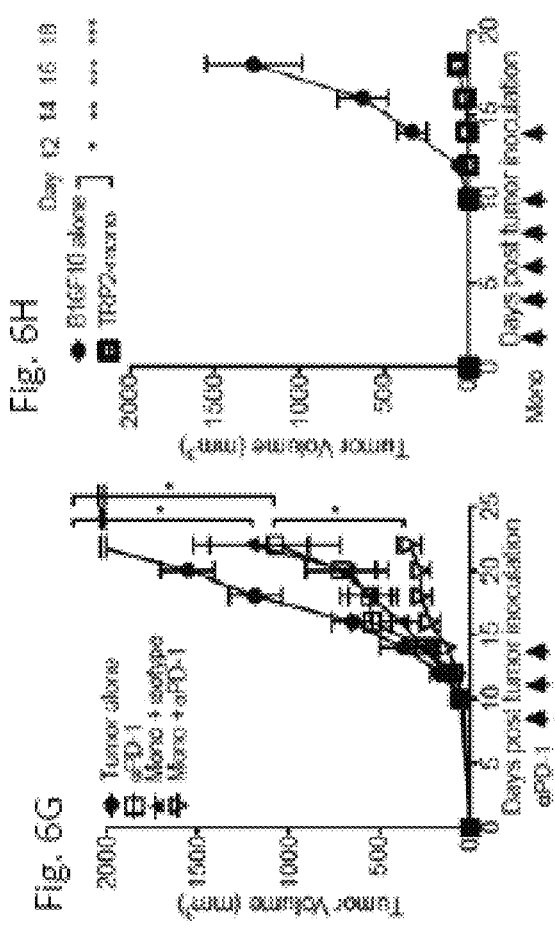
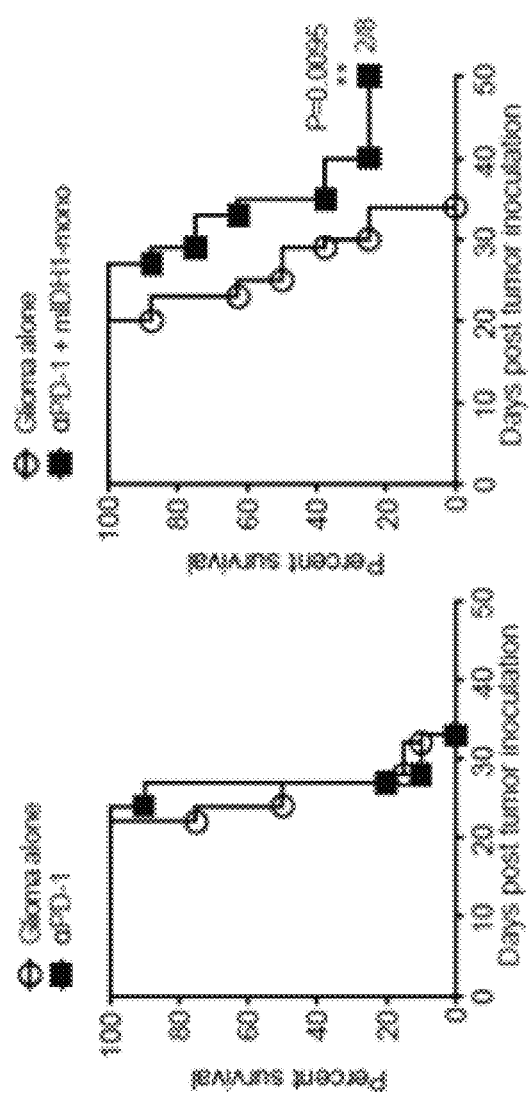

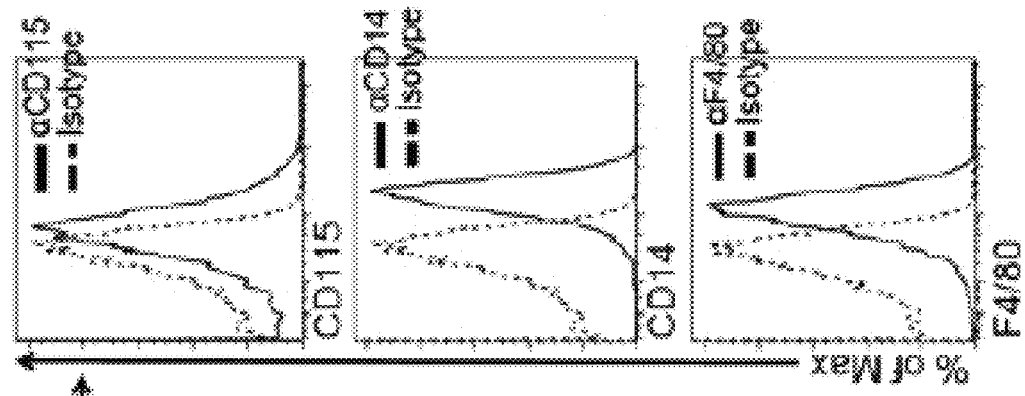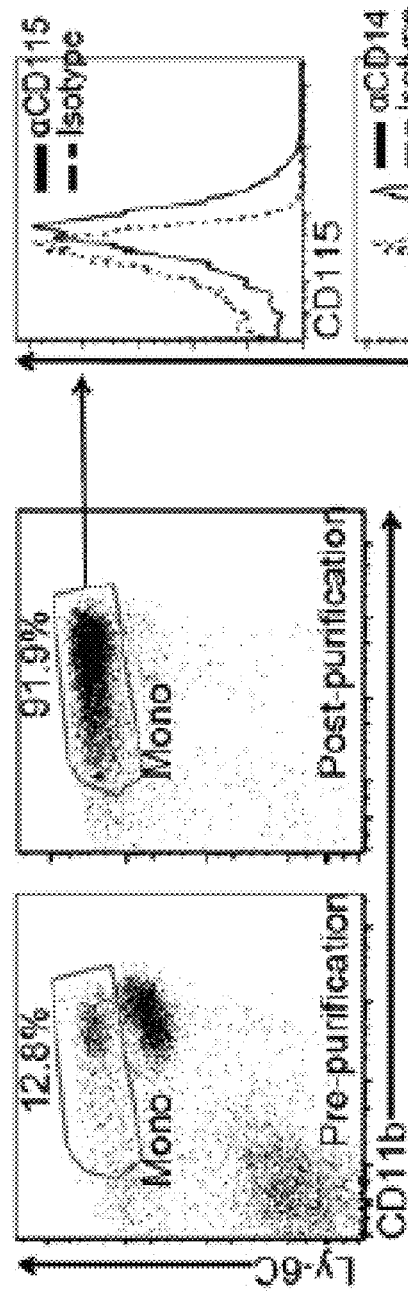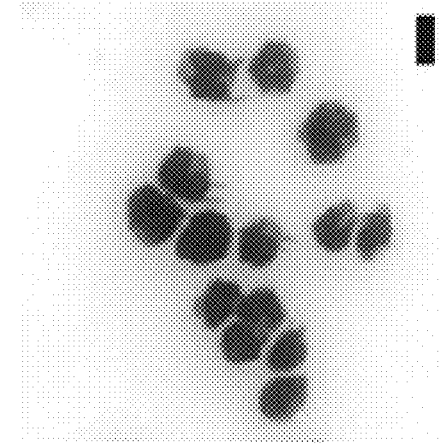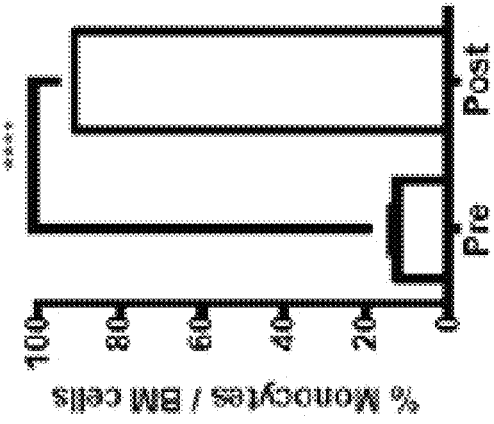

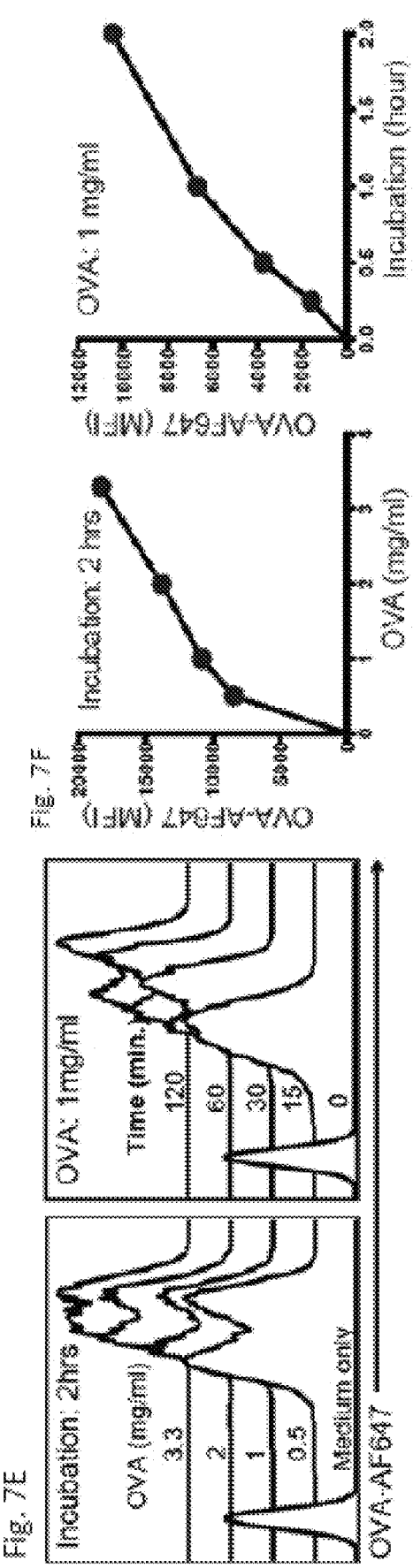

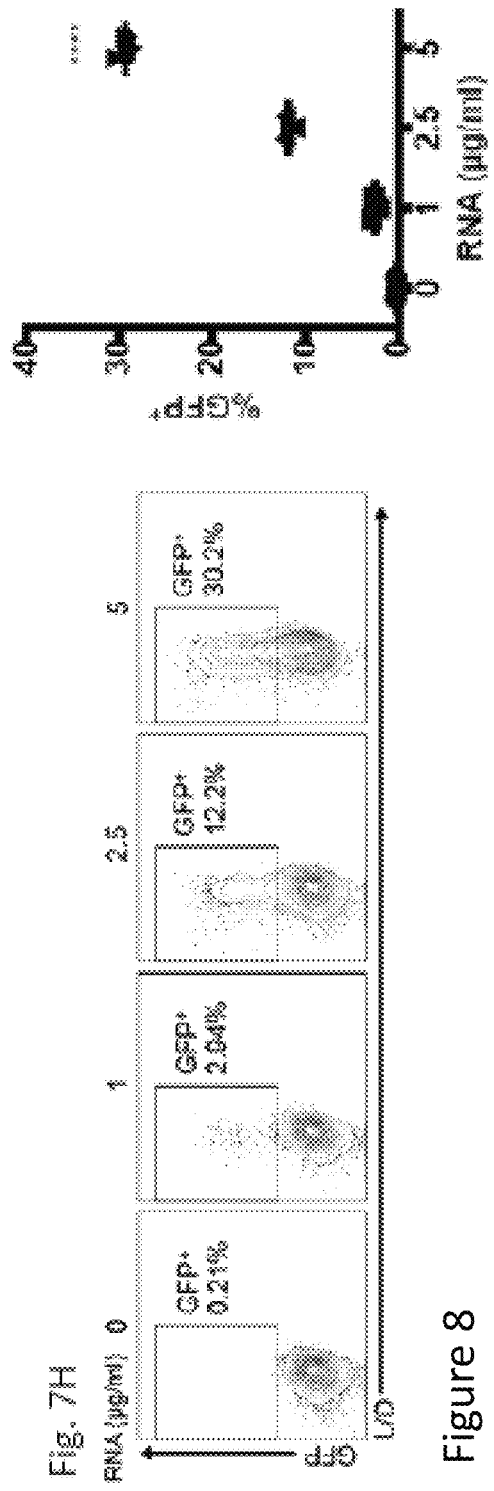
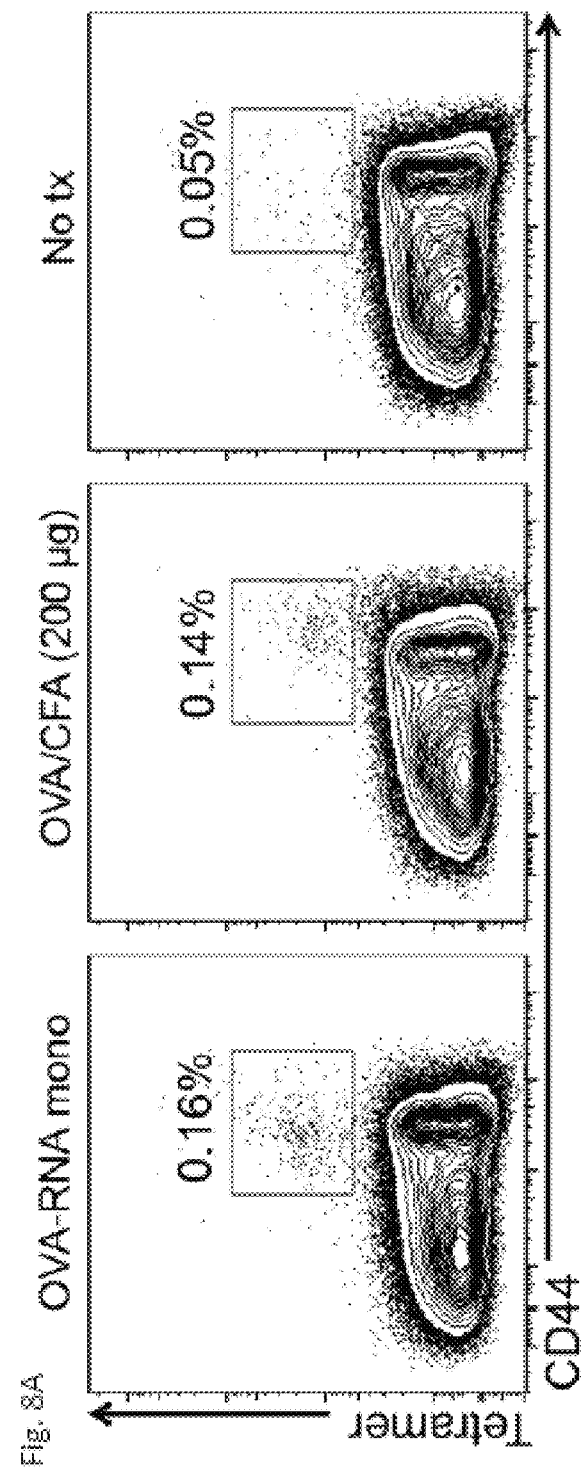
Figure 8

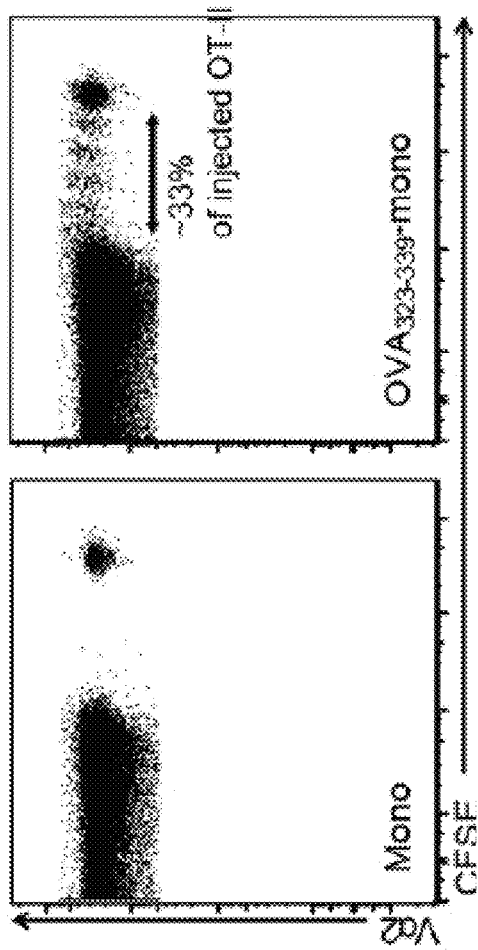
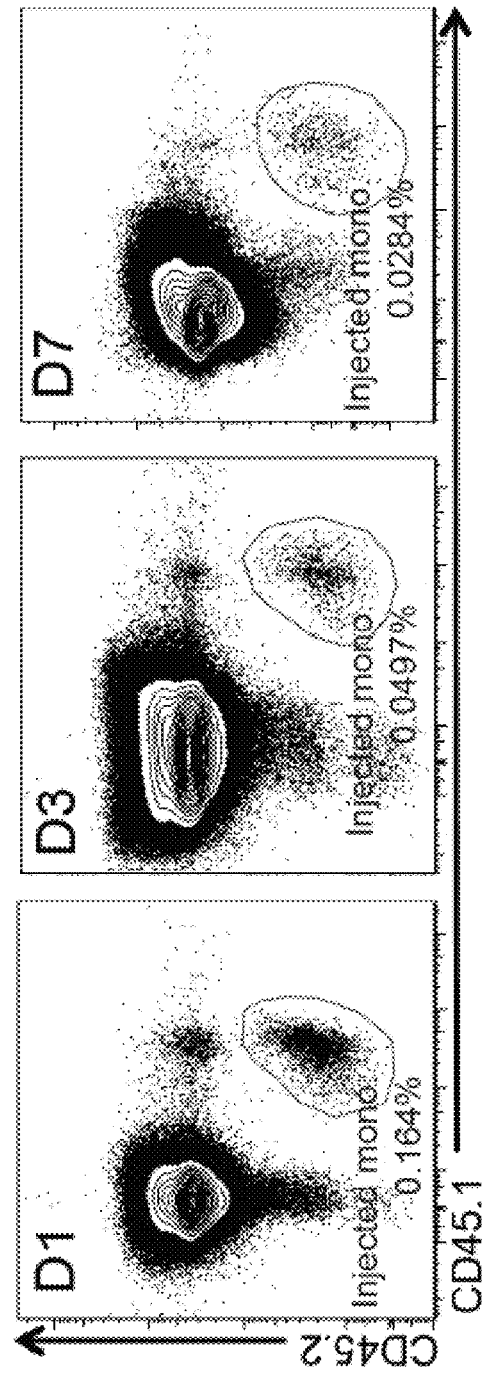
Figure 9

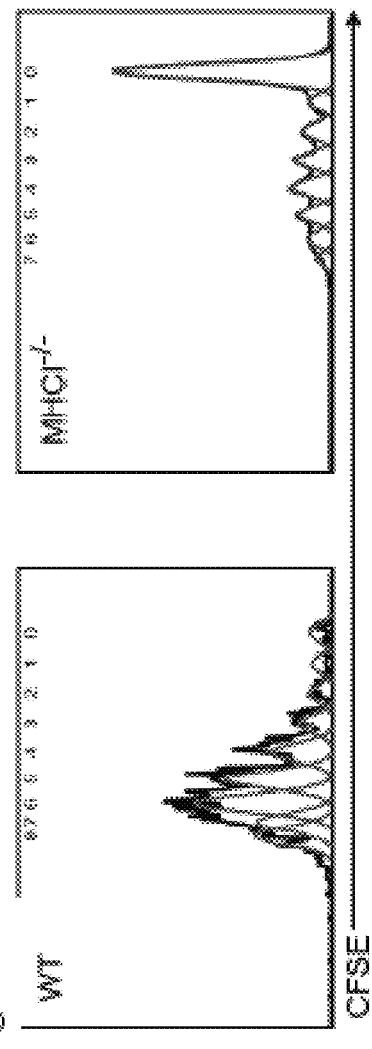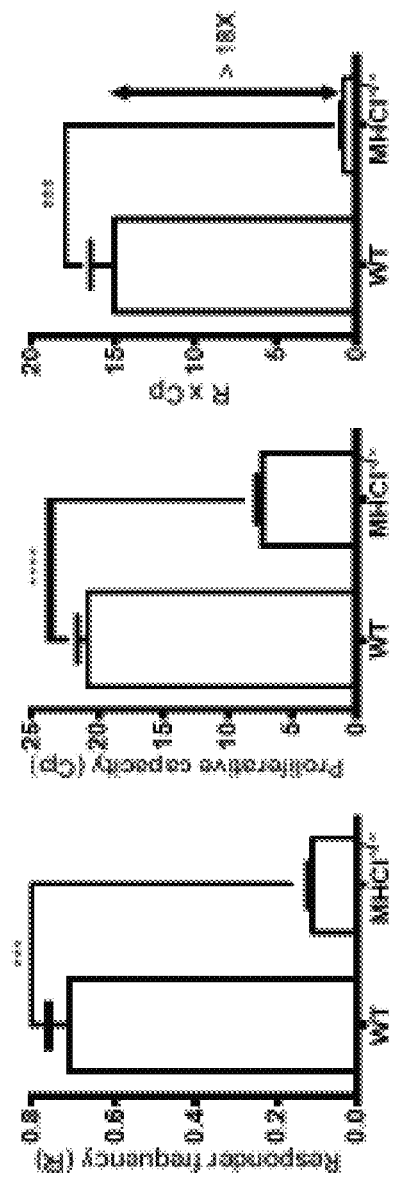
Fig. 10A
Fig. 10B

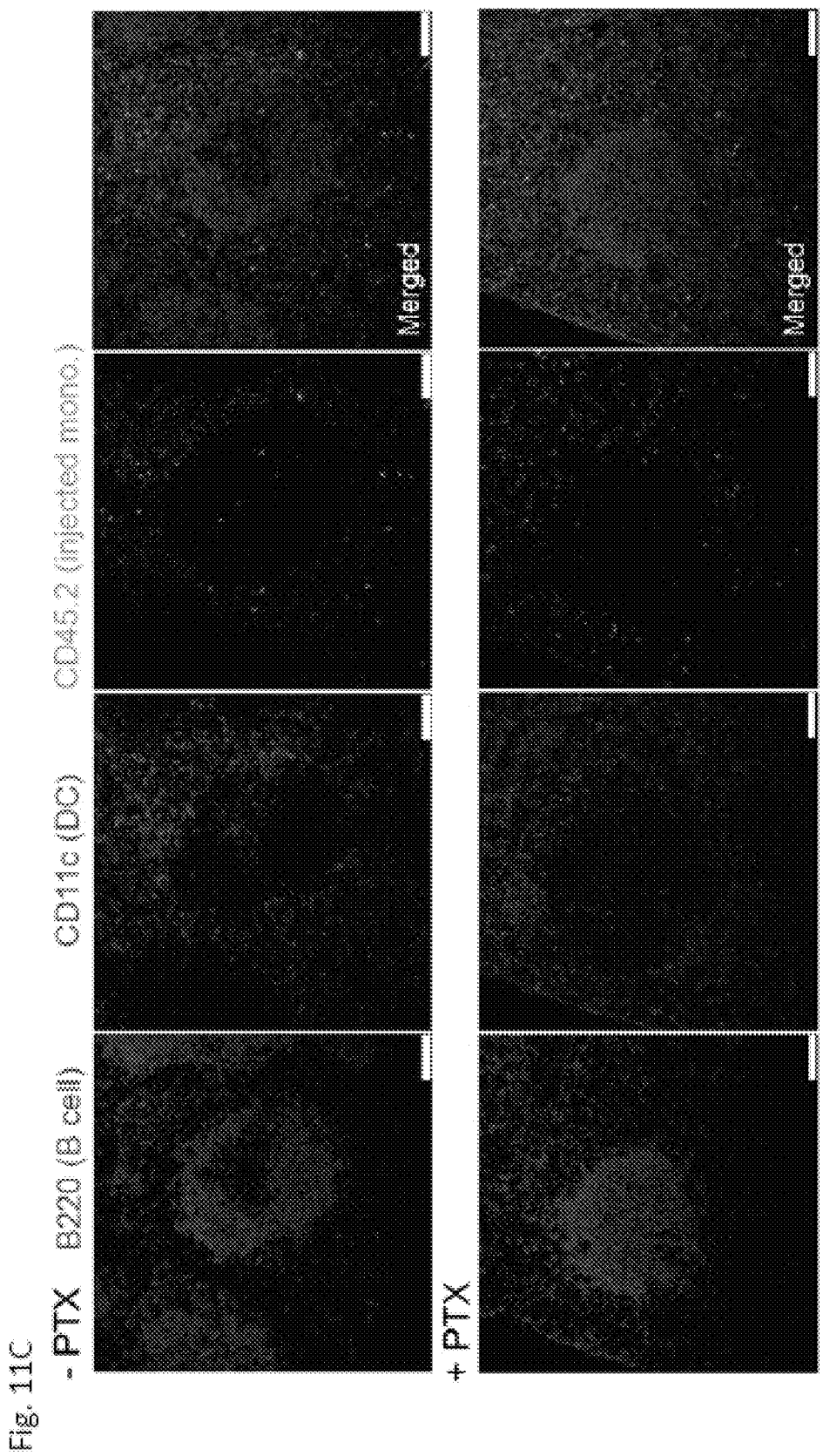

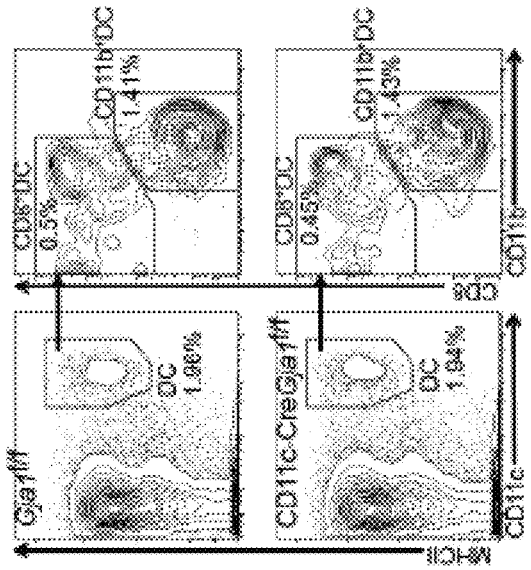
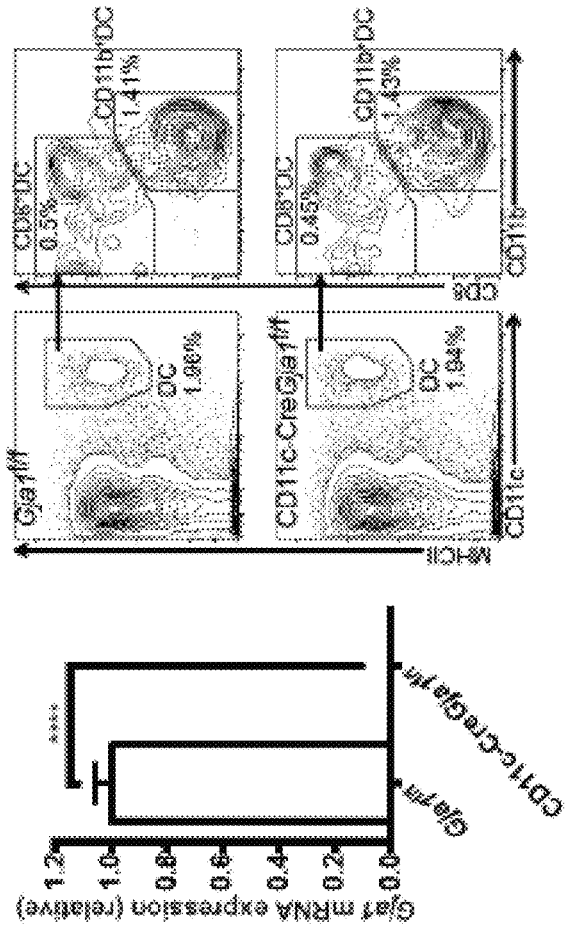
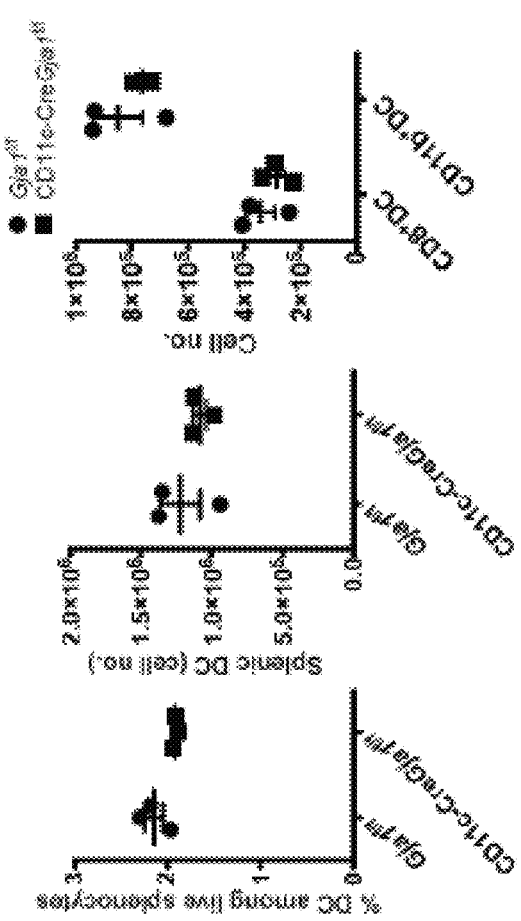
Fig. 14A
Fig. 14B
Fig. 14C

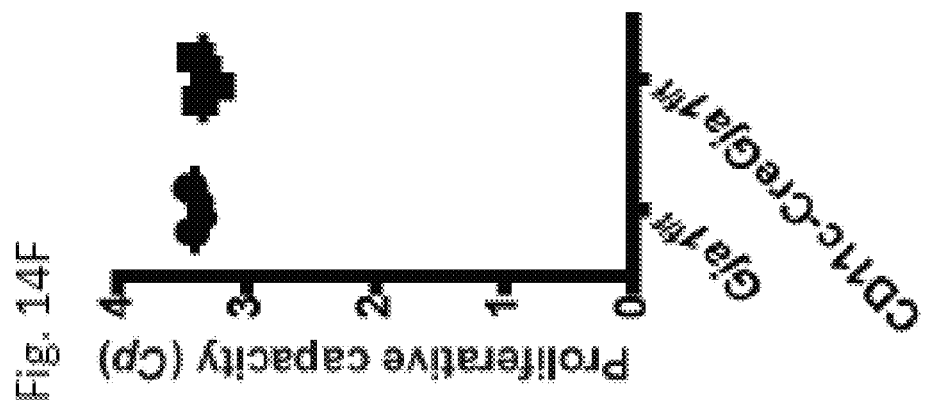
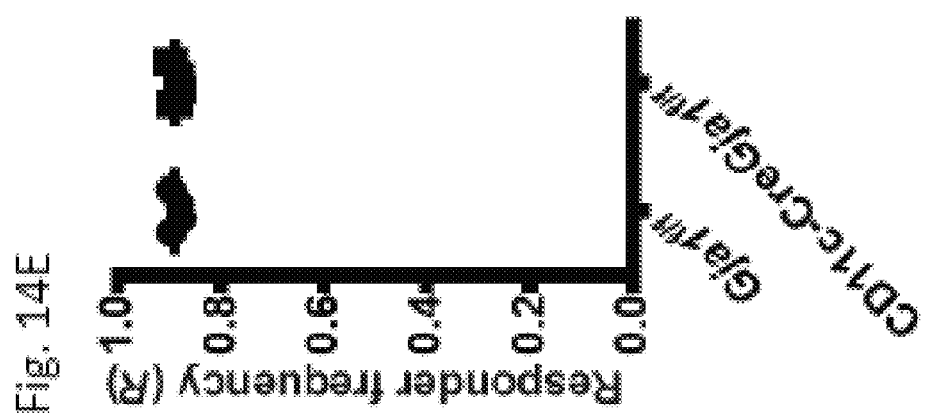
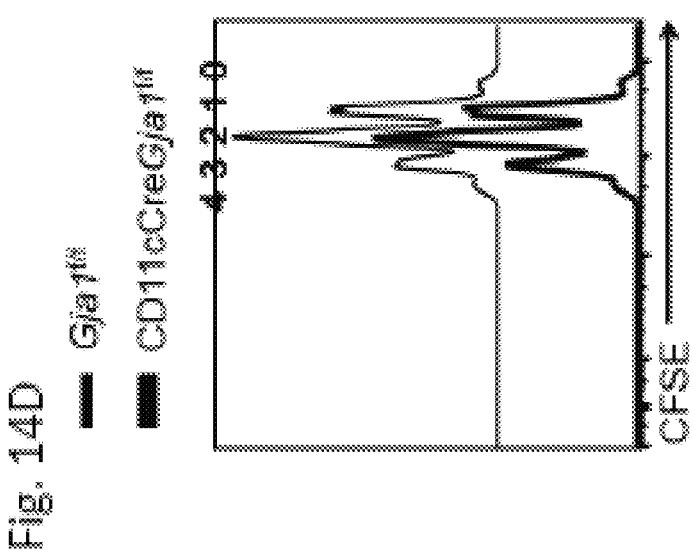
Fig. 14D
Fig. 14E
Fig. 14F

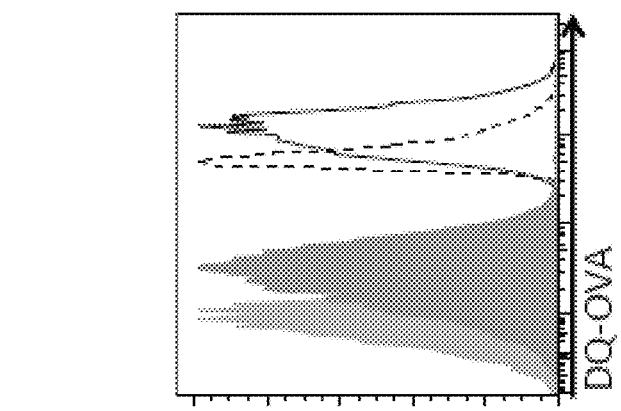
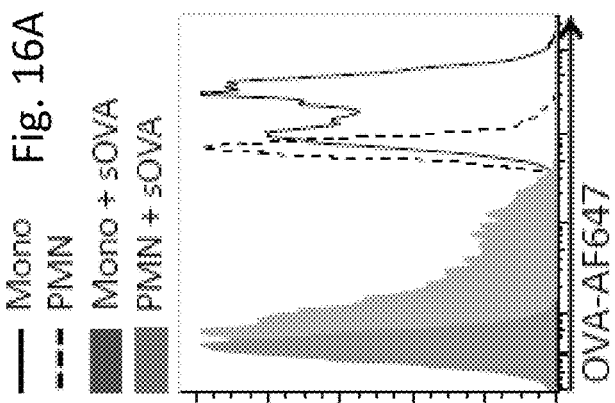
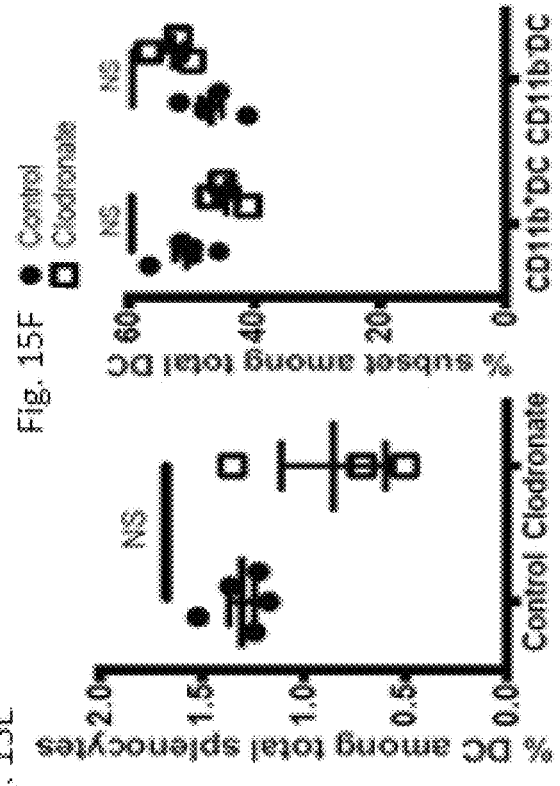
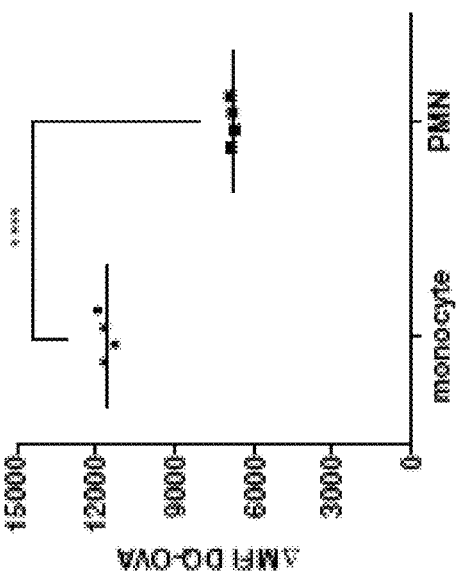
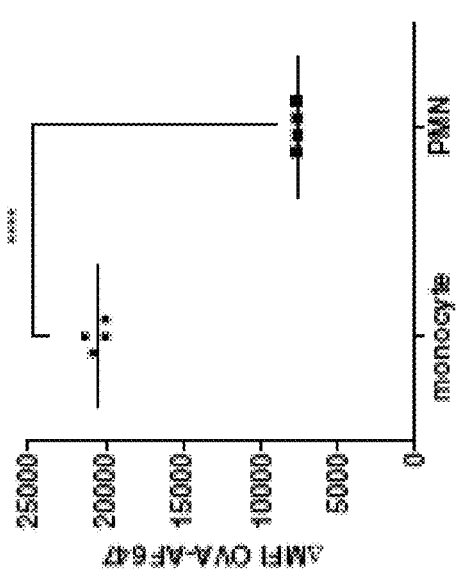

CELL-BASED VACCINE COMPOSITIONS AND METHODS OF USE

CROSS-REFERENCE TO RELATED APPLICATIONS

This patent application is a national stage filing under 35 U.S.C. 371 of International Application No. PCT/US2017/016362, filed Feb. 3, 2017, which claims the benefit of priority of U.S. Provisional Patent Application No. 62/291,086 filed on Feb. 4, 2016, both of which are incorporated herein by reference in their entirety.

STATEMENT REGARDING FEDERALLY SPONSORED RESEARCH

This invention was made with government support awarded by the National Institutes of Health grant numbers 1R01AI047262, P50CA190991 and CA225622. The government has certain rights in this invention.

SEQUENCE LISTING

This application is being filed electronically via EFS-Web and includes an electronically submitted Sequence Listing in .txt format. The .txt file contains a sequence listing entitled "2017-02-03_5667-00387_Sequence_Listing.txt" created on Feb. 3, 2017 and is 1,852 bytes in size. The Sequence Listing contained in this .txt file is part of the specification and is hereby incorporated by reference herein in its entirety.

INTRODUCTION

A novel method of generating an immune response in humans or other mammals using a cell-based vaccine composition is provided herein. The methods and vaccine compositions can be used to generate anti-tumor immune responses for use in treatment of patients with a variety of diseases including infectious diseases and malignancies.

Stimulation of anti-tumor immune responses has been shown to result in increased survival, remission, or even cure in a number of cases. Unfortunately, attempts to obtain such results in most patients have failed, in large part because methods of stimulating anti-tumor immunity are limited. One method, vaccination with tumor antigen-loaded dendritic cells (DC vaccines), has been approved for a single tumor type, but efficacy is limited. In most cases, DC vaccination is expensive, extremely cumbersome and not very effective. A novel vaccination method that is simple, cost-effective and stimulates an effective immune response in more than one type of disease is needed to overcome these obstacles.

SUMMARY

Methods of generating an autologous cellular vaccine composition are provided herein. The methods include selecting monocyte cells and/or neutrophil cells from a sample from a subject, contacting the selected cells with at least one antigenic polypeptide or at least one polynucleotide encoding the at least one antigenic polypeptide, and harvesting the resulting antigen-loaded cells to prepare the autologous cellular vaccine composition.

Cell-based antigen-loaded vaccine compositions made by the methods described herein are provided. The vaccine compositions may be used in the methods described herein. Pharmaceutical compositions comprising the antigen loaded cells and a pharmaceutical carrier are also provided.

Methods of eliciting an antigen-specific immune response in a subject by administering an effective amount of the vaccine compositions to the subject and eliciting an antigen-specific immune response in the subject are also provided.

Kits for generating a cellular vaccine composition are also provided. The kits include at least one antibody to a cell surface marker to isolate the monocytes or neutrophils; at least one antigenic polypeptide or at least one polynucleotide encoding the at least one antigenic polypeptide; and at least one reagent to facilitate uptake of the antigenic polypeptide or a polynucleotide encoding the antigenic polypeptide into the cells. For example an antibody to a cell surface protein such as CD14, Ly6G, GR-1 and CD66b may be used.

BRIEF DESCRIPTION OF THE DRAWINGS

FIG. 1 shows immune responses induced by Ag-loaded monocytes. FIG. 1A shows flow cytometry plots showing frequency of OVA-specific (SIINFEKL-H-2K$^b$ tetramer$^+$) CD8 T cells among splenic total CD8 T cells on Day 7 after SQ injection of 200 μg OVA in CFA (OVA/CFA), IV injection of OVA-loaded monocytes (OVA-mono), or IV injection of unloaded monocytes (Mono). All panels are gated on CD8 T cells and representative of 4 mice per group. FIG. 1B shows the frequency of OVA-specific CD8 T cells after the indicated treatments. NS: non-significant; **** $P<0.0001$ (one-way ANOVA with Tukey's test). FIGS. 1C and 1D show expression of cytotoxicity-related markers on splenic OVA-specific CD8 T cells presented as mean fluorescent intensity (MFI) (FIG. 1C) and % of positive cells among OVA-specific CD8 T cells (FIG. 1D) on Day 7 after injection with OVA/CFA or OVA-loaded monocytes ($4\times10^6$ cells). N=4 per group. Eomes: Eomesodermin. GZB: Granzyme B. * $P<0.05$;  $P<0.01$; * $P<0.001$; ** $P<0.0001$ (two-way ANOVA with Bonferroni's test). FIG. 1E shows the in vivo CTL activity of splenocytes toward SIINFEKL-pulsed targeted cells 7 days post SQ PBS/CFA, SQ OVA/CFA, and $4\times10^6$ IV OVA-loaded monocytes. N=4-5 per group. * $P<0.001$; ** $P<0.0001$ (one-way ANOVA with Tukey's test).

FIG. 2 shows in vivo tracking of IV injected Ag-loaded monocytes reveals the role of the spleen in monocyte vaccination. FIGS. 2A-2D show that CD45.1 OVA-loaded monocytes ($4\times10^6$ per mouse) were IV injected into CD45.2 recipient mice and in vivo tracked in different tissues over time post injection. FIG. 2A is a graph showing the absolute cell number of injected monocytes and OVA-specific CD8 T cells in different tissues over time post monocyte injection. N=3 per group. Monocyte cell number comparison: D7 v.s. D1; OVA-specific CD8 T cell number comparison: D7 v.s. D3. * $P<0.05$;  $P<0.01$; * $P<0.001$; **** $P<0.0001$ (unpaired two-tailed Student's t-test). FIGS. 2B and 2C shows representative flow plots gated on injected OVA-loaded monocytes in spleens showing expression of Ly-6C (FIG. 2B) and phenotypic DC differentiation (CD11c$^+$ MHCII$^+$) (FIG. 2C) over time post monocyte injection. FIG. 2D is a graph showing phenotypic DC differentiation of injected OVA-loaded monocytes in different tissues over time post monocyte injection. DC gating was the same as shown on (FIG. 2C) across different tissues. N=3 per group. % of DC comparison on D7: * P<0.05; *** P<0.001 (one-way ANOVA with Bonferroni's test).

FIG. 3 shows monocyte-induced T cell responses are impaired in the absence of endogenous DC. FIG. 3A shows the frequency of OVA-specific CD8 T cells in the spleen on Day 7 post IV injection with OVA-loaded WT, MHCI$^{-/-}$ or MHCII$^{-/-}$ monocytes ($4 \times 10^6$ per mouse). NS: non-significant (one-way ANOVA with Tukey's test). FIG. 3B is a set of histograms showing proliferation of adoptively transferred CFSE-labeled OT-I cells in the spleen of indicated recipient mouse strain on D3 post indicated monocyte treatment ($4 \times 10^6$ cells per mouse if treated). FIG. 3C is a set of histograms showing proliferation of CFSE-labeled OT-I and OT-II cells in spleens on D3 post monocyte vaccination ($3 \times 10^6$ per mouse). The experimental schematic is shown in FIG. 10C. FIG. 3D is a graph and statistics derived from FIG. 3C. **** P<0.0001 (unpaired two-tailed Student's t-test). FIG. 3E is a set of FACs histograms showing representative dot plots of CFSE-labeled human T cell proliferation in co-cultures of: CMVpp65 mRNA untransfected (Mono) or transfected (pp65-mono) human monocytes, plus or minus human monocyte-derived DC (DC) for 64 hours. L/D: Live/Dead dye. Samples from two CMV(+) donors. FIG. 3F is a graph derived from FIG. 3E. Each dot represents a single data point derived from samples of one donor. Data are representative of two independent experiments and presented as mean±s.e.m.

FIG. 4 shows differential sensitivity of monocyte-induced CD4 and CD8 T cell responses to pertussis toxin. FIG. 4A is a graph showing the frequency of OVA-specific CD8 T cells in the spleen on D7 post IV injection with OVA-loaded monocytes with the indicated chemokine receptor deletions. FIG. 4B shows a dot plot of OVA-specific CD8 T cells among total CD8 T cells in the spleen on D7 post IV injected with OVA-loaded monocytes ($4 \times 10^6$ per mouse) with (+) or without (−) PTX pre-treatment. FIG. 4C shows a graph and statistics derived from FIG. 4B. N=4 per group. FIG. 4D is a set of histograms showing proliferation of adoptively transferred CFSE-labeled OT-I and OT-II cells in spleens on D3 post IV injection of OVA-loaded monocytes ($4 \times 10^6$ per mouse) with (+) or without (−) PTX pre-treatment. FIG. 4E is a set of graphs and statistics derived from FIG. 4D showing total number of splenic OT-I and OT-II cells proliferating after IV monocyte injection. Data are representative of two independent experiments and presented as mean±s.e.m. * P<0.05; *** P<0.001 (unpaired two-tailed Student's t-test).

FIG. 5 shows mechanisms of antigen transfer from monocytes to dendritic cells. FIG. 5A is a graph showing proliferation of OT-I and OT-II cells cultured with OVA-loaded monocytes and DC in the presence or absence of transwells. ** P<0.0001 (compared to all the other groups; one-way ANOVA with Tukey's test). FIG. 5B shows images of DQ-OVA-loaded monocytes (arrows) cultured with splenic DC (arrowheads). Time display: hh:mm. FIG. 5C is a photograph showing interactions between donor CD45.2$^+$ OVA-monocytes and recipient splenic DC 1 day post injection. Scale bar: 50 µm. FIG. 5E shows distribution of Cx43 in the spleen. Scale bar: 100 µm. FIG. 5F shows presence of Cx43 at sites of monocyte-DC interactions. Scale bar: 10 µm. FIG. 5G shows a three-dimensional reconstruction of inset in FIG. 5F. Scale bar: 2 µm. FIG. 5I is a set of representative dot plots showing frequency of OVA-specific CD8 T cells in the spleens of control and DC Cx43$^{-/-}$ mice after IV OVA-monocyte injection. Gja1: Cx43 gene. FIG. 5J is a set of graphs and statistics derived from FIG. 5I. * P<0.001 (unpaired two-tailed Student's t-test). FIG. 5K shows proliferation of OT-II cells in spleens of DC Cx43$^{-/-}$ and control mice on D3 post IV OVA-loaded monocyte injection ($3 \times 10^6$ per mouse). FIG. 5L is a set of histograms showing proliferation of splenic OT-I and OT-II cells in mice treated with control liposomes or liposomal clodronate on Day 3 post IV OVA-loaded monocyte injection ($4 \times 10^6$ per mouse). FIG. 5M is a graph and statistics derived from FIG. 5L. N=5 per group. NS: non-significant; *** P<0.001 (two-way ANOVA with Bonferroni's test). In FIGS. 5H and 5M the % of CFSE$^{lo}$ cells is normalized to the mean of the % seen in the control group. Data are representative of two independent experiments and presented as mean±s.e.m.

FIG. 6 shows the anti-tumor efficacy of Ag-loaded monocytes. FIGS. 6A and 6B are graphs showing growth of SQ B16/F10-OVA tumors in mice untreated (Tumor alone) or vaccine-treated beginning 8 days post tumor inoculation. In FIG. 6A vaccines: $10^6$ OVA-loaded monocytes IV weekly ×3 (Mono 3×) or $10^6$ intradermal OVA RNA-DC weekly ×3 (DC 3×) with tetanus-diphtheria toxoid immunization (Td) and adoptive lymphocyte (OT-I) transfer (ALT) N=8. In FIG. 6B vaccines: $3 \times 10^6$ OVA-loaded monocytes IV ×1 (Mono 1×) or OVA RNA-pulsed DC×3+Td without ALT. N=8 per group. FIG. 6C is a graph showing growth of SQ B16/F10-OVA tumors in mice untreated (No treatment) or immunized 42 days earlier with $3 \times 10^6$ OVA-loaded monocytes IV ×1 (Mono). N=9 per group. FIG. 6D shows survival curves of mice from FIG. 6C. FIG. 6E-6G are graphs showing growth of SQ B16/F10-OVA tumors in mice untreated or treated with checkpoint blockade, monocytes+ control Ab, or monocytes+checkpoint blockade. In FIG. 6E, treatments: Anti-CTLA4 (αCTLA4), $2 \times 10^6$ OVA-loaded monocytes IV ×1 and control Ab (Mono+isotype), or OVA-loaded monocytes IV ×1 and anti-CTLA4 (Mono+αCTLA4). N=9 per group. In FIG. 6F, treatments: Anti-PD-L1 (αPD-L1), $2 \times 10^6$ OVA-loaded monocytes IV ×1 and control Ab (Mono+isotype), or OVA-loaded monocytes IV ×1 and anti-PD-L1 (Mono+αPD-L1). N=9 per group. In FIG. 6G, treatments: Anti-PD-1 (αPD-1), $2 \times 10^6$ OVA-loaded monocytes IV ×1 and control Ab (Mono+isotype), or OVA-loaded monocytes IV ×1 and anti-PD-1 (Mono+αPD-1). N=9 per group. FIG. 6H is a graph showing growth of SQ B16/F10 tumors in mice untreated or treated with $10^6$ TRP2$_{180-188}$-loaded monocytes IV ×6 (TRP2-mono) on Days 2, 4, 6, 8, 10 and 14 post tumor inoculation. N=9 per group. FIG. 6I is a graph showing survival curves of mice from FIG. 6H. FIG. 6J is a set of graphs showing survival curves of mice intra-cranially inoculated with CT-2A-mIDH1 cells and either untreated or treated with anti-PD-1 Ab (αPD-1) or anti-PD-1 and $3×10^6$ mIDH1 peptide-loaded monocytes IV ×1 (αPD-1+mIDH1-mono) beginning 3 days post tumor inoculation. N=8-10 per group. Data representative of two independent experiments (mean±s.e.m.). Tumor size comparisons: NS: non-significant; * P<0.05;  P<0.01; * P<0.001; **** P<0.0001 (unpaired two-tailed Student's t-test). Survival curve comparisons: * P<0.05;  P<0.01; * P<0.001 (Log-rank test).

FIG. 7 shows antigen-loading of purified bone marrow (BM)-derived monocytes. Murine classic Ly-6C$^{hi}$ monocytes were purified from BM cells via negative selection with MACS columns. FIG. 7A is a set of histograms showing representative dot plots showing percentages of classic Ly-6C$^{hi}$ monocytes among total BM cells pre- and post-purification. FIG. 7B shows a set of histograms showing the phenotype of purified monocytes. FIG. 7C is a graph showing monocyte purity pre- and post-purification (n=3 per group). Data are presented as mean±s.e.m. ** P<0.0001 (unpaired two-tailed Student's t-test). FIG. 7D shows a photograph of cytospins of MACS-purified cells stained with Wright-Giemsa (scale bar: 10 µm). FIG. 7E shows representative histograms of OVA uptake by monocytes at increasing incubation times and OVA concentrations. Purified monocyes were incubated with AF647-conjugated OVA protein and uptake measure by flow cytometric analysis. FIG. 7F is a set of graphs of OVA protein uptake as a function of OVA concentration and incubation time (MFI: geometric mean fluorescent intensity). FIG. 7G is a set of representative dot plots showing monocyte uptake of FITC-conjugated OVA$_{323-339}$ peptide at the indicated concentrations with 1.5-hour co-incubation time. Based on these results, we chose to incubate monocytes with 1 mg/ml of protein or 200-250 µg/ml of peptide for 1.5-2 hours as our standard procedure. These conditions were used for all studies unless otherwise noted. FIG. 7H shows flow cytometric analysis of monocytes 4 hours after they were loaded with EGFP mRNA using lipofectamine transfection. FIG. 7I shows the percentage of GFP$^+$ monocytes after transection with increasing concentrations of EGFP mRNA. ** P<0.0001 (compared to all the other groups; one-way ANOVA with Tukey's test).

FIG. 8 shows T cell responses induced by Ag-loaded monocytes. FIG. 8A is a set of representative dot plots gated on CD8 T cells showing frequency of OVA-specific (SIINFEKL-H-2K$^b$ tetramer$^+$) CD8 T cells among total CD8 T cells in the spleen on D7 post different treatments as indicated. OVA-RNA mono: IV OVA-mRNA-loaded monocyte injection at a dose of $6×10^6$ cells. FIG. 8B is a set ofrRepresentative dot plots gated on Vα2$^+$CD4$^+$ T cells showing proliferation of adoptively transferred OT-II cells (Vα2$^+$CFSE$^+$) in spleens on D3 post IV injection of OVA$_{323-339}$-loaded monocytes. Mono: peptide-unloaded monocytes ($4×10^6$ per mouse). OVA$_{323-339}$-mono: OVA$_{323-339}$-loaded monocytes ($4×10^6$ per mouse). Data are presented as mean±s.e.m. ** P<0.01 (one-way ANOVA with Tukey's test).

FIG. 9 shows in vivo monocyte tracking. Representative dot plots gated on live CD45$^+$ cells in spleens at indicated time points post CD45.1 monocyte injection into CD45.2 recipient mice. The percentages represent the frequency of the injected CD45.1$^+$ monocytes among total live CD45$^+$ cells in spleens.

FIG. 10 shows monocyte-driven T cell proliferation in APC-deficient mice. FIG. 10A shows a set of representative histograms showing OT-I cell proliferation in spleens of recipient mice on D7 post monocyte vaccination. The numbers on the top of the plots indicate the generation number of the proliferating cells. FIG. 10B is a set of graphs with statistics derived from FIG. 10A. N=4 per group.

FIG. 11 shows PTX effects on in vivo monocyte migration and endogenous DCs. Monocytes were treated (+) or untreated (−) with PTX during co-incubation with OVA proteins. FIG. 11C shows photographs of immunoflurescent staining of spleen sections on D1 post OVA-loaded monocyte injection. The injected monocytes are CD45.2$^{+/+}$ and recipients are CD45.1 mice. Scale bar: 100 µm.

FIG. 14 shows the phenotypes of CD11c-CreGja1$^{f/f}$ mice. FIG. 14A is a graph showing relative Cx43 (Gja1) mRNA expression of splenic DCs revealed by real-time PCR. N=3 per group. **** P<0.0001 (unpaired two-tailed Student's t-test). FIG. 14B shows representative contour plots showing frequency of DCs among total live splenocytes and frequency of DC subsets among total splenic DCs. FIG. 14C shows graphs and statistics derived from FIG. 14B. FIG. 14D shows representative histograms showing proliferation of CFSE-labeled OT-I cells being stimulated by SIINFEKL-pulsed splenic DCs for 64 hours. The numbers on top of the histogram indicate the proliferating generations of OT-I cells. FIGS. 14E and 14F show graphs and statistics derived from FIG. 14D. Data are presented as mean±s.e.m. No statistical significance was found by two-way ANOVA with Bonferroni's test (the most far right panel of FIG. 14C and unpaired two-tailed Student's t-test (all the other panels except FIG. 14A).

FIG. 15 shows depletion of splenic macrophages. Liposomal clodronate was given i.p. to deplete macrophages in vivo. Splenic macrophage and DC populations were assessed on D5 post clodronate treatment. FIG. 15E shows the frequency of DCs among total live splenocytes. FIG. 15F shows the frequency of DC subsets among total splenic DCs. Data are presented as mean±s.e.m. NS: non-significant; * $P<0.05$; *** $P<0.001$ (unpaired two-tailed Student's t-test).

FIG. 16 shows a set of data showing that antigen-loaded neutrophils can induce antigen-specific T cell responses. FIG. 16A is a set of FACS plots showing that monocytes and neutrophils can be loaded with antigen. FIG. 16B is a set of graphs comparing the number of cells loaded with antigen and indicates monocytes are loaded with antigen more efficiently than neutrophils.

DETAILED DESCRIPTION

Figure 1F:
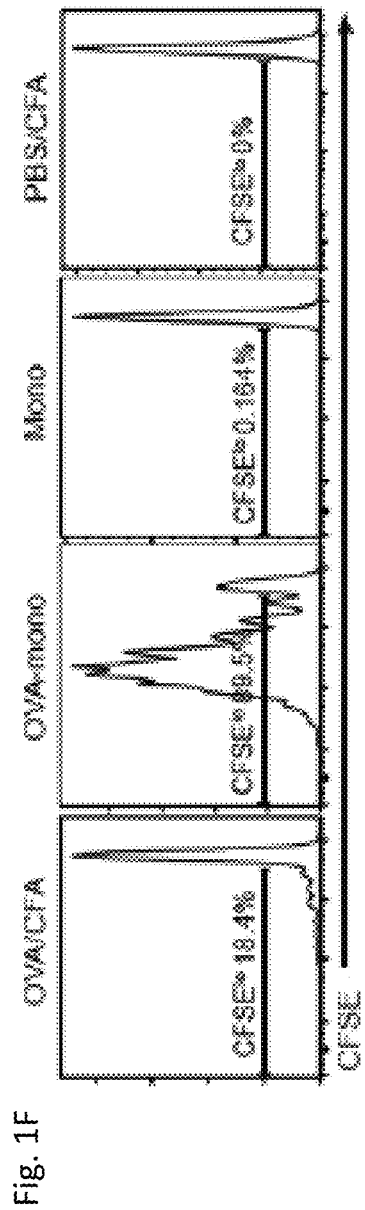
FIG. 1F shows a set of representative histograms showing proliferation of adoptively transferred CFSE-labeled OT-II cells in spleens on Day 3 after the indicated treatments. Monocyte dose: $4\times10^6$ cells per mouse.

In the course of examining the basic mechanisms of immune response, the inventors made an observation that was contrary to all current dogma and expectations. Specifically, the inventors found that dendritic cells that migrate from tissues into lymphoid organs are not the stimulus for Th1 immune responses, the most potent type of immune response. Instead, the inventors found that monocytes entering lymphoid organs from the blood are both sufficient and necessary to induce Th1 immune responses.

All current cell-based vaccines are DC vaccines. These DC vaccines are based on a technology of generating dendritic cells in vitro, loading them with tumor antigens, then injecting them into patients, typically by the subcutaneous route. However, the inventors' recent research suggested that the cells being injected are not the cells that normally stimulate the most potent immune responses. Instead, the most potent immune responses could be induced by injecting antigen-loaded monocytes.

To test this hypothesis that antigen-loaded monocytes may be more efficient at stimulating a protective immune response, monocyte vaccination was directly compared with the standard DC vaccination in mice bearing melanoma tumors expressing the model antigen OVA. As shown in FIG. 6, a single dose of monocyte vaccine almost completely inhibited tumor growth, while 3 doses of an optimized DC vaccine had no effect. The monocyte vaccine was also more effective than immunization with protein in Complete Freund's Adjuvant (CFA), a therapy that is too toxic to be used in humans. This result demonstrates that monocyte vaccination has the potential to be much more efficacious than DC vaccination.

The other potential advantage of monocyte vaccination is its simplicity. While DC vaccination requires complex methods to culture and stimulate the differentiation of cells into DC over several days, monocyte vaccination requires only 1-2 hours of antigen loading, after which the cells are immediately re-infused into the patients. Thus, monocyte vaccination is the first fully practical and efficacious means to stimulate anti-tumor immune responses in humans.

In more recent results shown in the Examples, we demonstrate that neutrophils can also be antigen loaded and present another cell-type for making cell-based vaccine compositions. The vaccine compositions disclosed herein may be monocyte-based vaccines, neutrophil-based vaccines or a combination of the two cell types in any ratio. Suitably, the vaccine compositions described herein do not include dendritic cells or at most contain less than 0.01%, 0.1%, 1%, 2%, 3% or 5% dendritic cells. In some embodiments, the monocytes cells used in the vaccine compositions have not been exposed to cytokines in vitro. The vaccine compositions may comprise 50%, 60%, 70%, 80%, 90%, 95%, 98% or even 99% of the selected and isolated cell type, i.e. monocytes and/or neutrophils.

Methods of making cell-based vaccine compositions, the cell-based vaccine compositions made using those methods and the methods of using the cell-based vaccine compositions to treat diseases are all provided herein. In brief, the cell-based vaccine compositions are made by selecting monocytes and/or neutrophils from a sample from the subject. The selected monocytes and/or neutrophils are then contacted with an antigenic polypeptide or a polynucleotide encoding the antigenic polypeptide in order to load the cells with the antigenic polypeptide or polynucleotide encoding the antigenic polypeptide. More than one antigenic polypeptide or polynucleotide may be loaded into the cells. Finally, the loaded cells are collected to prepare the vaccine composition. The resultant vaccine composition can be administered to the subject to treat the disease or condition. Mammals and in particular humans represent suitable subjects though any animal with an immune system comprising T cells can be used in the methods.

Suitably the cells are autologous and the cells used to create the cell-based vaccine are from the same person who will eventually be treated with the cell-based vaccine formulation. The sample used to obtain the cells may be a sample containing blood cells such as a peripheral blood sample, from which the red blood cells and other cells types are removed prior to preparing the cell-based vaccine composition. A bone marrow sample may also be used. The cells may be isolated to avoid inclusion of cells in the vaccine compositions that may have inhibitory effects on the vaccination methods. The methods of isolating monocytes and/or neutrophils are well known in the art and include elutriation, FACS (using cell surface markers), MACS, density gradients and other similar methods. The monocytes may be positively selected for CD14 and may be selected as negative for CD1, CD83 and/or CCR7. These markers are found on dendritic cells and not on monocytes. The neutrophils may be positively selected by expression of CD66b or size and granularity profiles.

Cells may be contacted with the antigen directly or indirectly in vitro or ex vivo. Contacting encompasses administration to a cell or tissue. Further, contacting a cell includes adding an antigen to a cell by addition in the culture media to allow uptake of the antigen. Other suitable methods may include introducing or administering an antigen to a cell or tissue using appropriate procedures and routes of administration to allow the antigen to enter the cell. For example a polynucleotide encoding an antigenic polypeptide may be electroporated, transformed or transfected into a cell. Other means of delivering an antigenic polypeptide or a nucleic acid encoding the antigenic polypeptide include but are not limited to liposomal mediated delivery, receptor-mediated delivery, inclusion in a viral or other agent capable of infecting the cell, and translocation by linking the antigenic polypeptide to a protein capable of crossing the cellular membrane or an antibody that binds an endocytic receptor. Delivery particles may be used to load either the antigenic polypeptide or the nucleic acid encoding the antigenic polypeptide into the cells to produce the cell-based vaccines. Delivery particles suitable for delivering polynucleotides and/or proteins are known in the art and may include, without limitation, polymeric nanoparticles, liposomal nanoparticles, and nanoparticles including lipids and at least one type of polymer. The polynucleotide encoding the antigenic polypeptide may be a DNA or RNA molecule.

The cells may be contacted with the antigenic polypeptide or the polynucleotide encoding the antigenic polypeptide for at least 15 minutes, 30 minutes, 45 minutes, 1 hour, 1.5 hours, 2 hours or more. In some embodiments the contacting step is minimized to minimize the time the cells are in vitro prior to being administered to the subject. Suitably the cells are not contacted with the antigenic polypeptide or polynucleotide encoding the antigenic polypeptide for more than 2 hours, 4, 6, 8, 10, 12, 16, 20, 24 or 48 hours. The amount of time the cells remain ex vivo without being frozen may be minimized.

An antigenic polypeptide is a polypeptide that is capable of being specifically recognized by the adaptive immune system. An antigenic polypeptide includes any polypeptide that is immunogenic. The antigenic polypeptides include, but are not limited to, antigens that are pathogen-related, allergen-related, tumor-related, cancer-related or other disease-related. Pathogens include viral, parasitic, fungal and bacterial pathogens as well as protein pathogens such as the prions. The antigenic polypeptides may be full-length proteins or portions thereof. It is well established that immune system recognition of many proteins is based on a relatively small number of amino acids, often referred to as the epitope. Epitopes may be only 8-10 amino acids. Thus, the antigenic polypeptides described herein may be full-length proteins, 8 amino acid long epitopes or 10, 12, 15, 18, 20, 25, 30, 35, 40, 50 amino acids long or any portion between these extremes. In fact the antigenic polypeptide may include more than one epitope from a single disease or protein. The antigenic polypeptide may be natively expressed or may represent one or more common mutations associated with a disease. The antigenic polypeptide may be a tumor antigen, or a tumor lysate without any particular antigen identified. The antigenic polypeptide may be a CD4 peptide, CD8 peptide, CD8/CD4 peptide. In other words, the antigenic polypeptide may be a known epitope for binding CD4, CD8 or both T cells via interaction with MHC class I, MHC class II or both and eliciting a T cell mediated immune response.

Once the monocytes and or neutrophils are loaded with the antigenic polypeptide, the cells can be harvested to prepare the vaccine composition. The harvesting step may only entail removing excess antigenic polypeptide or polynucleotide and suspending the cells in a pharmaceutically acceptable carrier or buffer for administration to the subject or may require washing the cells to remove excess antigenic polypeptide or polynucleotide or any delivery vehicle used to help load the cells with the antigenic polypeptide prior to suspending the cells in a pharmaceutically acceptable carrier.

Methods of eliciting an antigen-specific immune response in a subject by administering an effective amount of the vaccine composition to the subject are provided. The administration of the vaccine composition results in an antigen-specific immune response and this immune response is beneficial to the subject. The immune response may be a CD4 or CD8 T cell response and may alleviate at least one symptom of a disease or condition in the subject. The antigen-specific immune response may be an anti-tumoral or anti-cancer immune response and may result in a reduction in the size or growth of the tumor or cancer or treatment of the disease or cancer.

Treating cancer includes, but is not limited to, reducing the number of cancer cells or the size of a tumor in the subject, reducing progression of a cancer to a more aggressive form, reducing proliferation of cancer cells or reducing the speed of tumor growth, killing of cancer cells, reducing metastasis of cancer cells or reducing the likelihood of recurrence of a cancer in a subject. Treating a subject as used herein refers to any type of treatment that imparts a benefit to a subject afflicted with a disease or at risk of developing the disease, including improvement in the condition of the subject (e.g., in one or more symptoms), delay in the progression of the disease, delay the onset of symptoms or slow the progression of symptoms, etc.

Pharmaceutical compositions comprising the cell-based vaccine compositions (i.e., antigen-loaded monocytes and/or neutrophils from a sample from the subject) described above and a pharmaceutically acceptable carrier are provided. A pharmaceutically acceptable carrier is any carrier suitable for in vivo administration. Examples of pharmaceutically acceptable carriers suitable for use in the composition include, but are not limited to, water, buffered solutions, glucose solutions, oil-based or bacterial culture fluids. Additional components of the compositions may suitably include, for example, excipients such as stabilizers, preservatives, diluents, emulsifiers and lubricants. Examples of pharmaceutically acceptable carriers or diluents include stabilizers such as carbohydrates (e.g., sorbitol, mannitol, starch, sucrose, glucose, dextran), proteins such as albumin or casein, protein-containing agents such as bovine serum or skimmed milk and buffers (e.g., phosphate buffer). Especially when such stabilizers are added to the compositions, the composition is suitable for freeze-drying or spray-drying. The composition may also be emulsified.

The cell-based vaccines described herein may also be co-administered with other agents such as the immune checkpoint inhibitors described in the Examples. The checkpoint inhibitory agents may be an antibody antagonistic for an inhibitory checkpoint molecule including but not limited to CTLA-4, PD1, PD-L1, A2AR, B7-H3 (CD276), B7-H4, BTLA, IDO, KIR, LAG3, TIM-3, and VISTA. In the Examples, a PD1 antibody, a PD-L1 antibody and a CTLA-4 antibody were used. Other similar antibodies are commercially available or in clinical trials such as ipilimumab, pembrolizumab, and nivolumab. The vaccine formulations may be administered before, during or after treatment with other cancer therapeutic or prevention agents or may be administered simultaneously with other cancer therapeutic or prevention agent. The vaccine formulations described herein may also be combined with adjuvants to increase immunogenicity of the vaccine and derive pharmaceutical compositions. In some embodiments, these compositions comprise one or more of a mineral adjuvant, gel-based adjuvant, tensoactive agent, bacterial product, oil emulsion, particulated adjuvant, fusion protein, and lipopeptide. Vaccine compositions may further comprise cytokines (e.g.

IFN-γ, granulocyte-macrophage colony stimulating factor (GM-CSF) IL-2, or IL-12) or immunostimulatory molecules such as FasL, CD40 ligand or a toll-like receptor agonist, or carbohydrate adjuvants.

Co-administration of the cell-based vaccine formulations with these other agents described above includes administration in any order, at the same time and may occur via the same or different routes of administration or as part of a unitary composition. The cell-based vaccine formulations and other therapeutics may be administered such that one is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks or more.

An effective amount or a therapeutically effective amount as used herein means the amount of a compound that, when administered to a subject for treating a state, disorder or condition is sufficient to effect a treatment (as defined above) for the disease or disorder such as cancer. The therapeutically effective amount will vary depending on the compound, formulation or composition, the disease and its severity and the age, weight, physical condition and responsiveness of the subject to be treated. Those of skill in the art will be able to determine the therapeutically effective amount.

The cell-based vaccine formulations described herein may be administered by any means known to those skilled in the art, including, but not limited to, intraperitoneal, parenteral, intravenous, intramuscular, subcutaneous, intrathecal, nasopharyngeal, intra-tumoral, or intracranial. Thus the vaccine compositions may be formulated as an injectable, topical or suppository formulation. The vaccine compositions may also be delivered within a liposomal or time-release vehicle. Administration of the vaccine compositions to a subject in accordance with the invention appears to exhibit beneficial effects in a dose-dependent manner. Thus, within broad limits, administration of larger quantities of the vaccine compositions is expected to achieve increased beneficial biological effects than administration of a smaller amount. Moreover, efficacy is also contemplated at dosages below the level at which toxicity is seen.

It will be appreciated that the specific dosage administered in any given case will be adjusted in accordance with the vaccine compositions being administered, the disease to be treated or inhibited, the condition of the subject, and other relevant medical factors that may modify the activity of the vaccine compositions or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the vaccine compositions of the invention and of a known agent, such as by means of an appropriate conventional pharmacological or prophylactic protocol.

The maximal dosage for a subject is the highest dosage that does not cause undesirable or intolerable side effects. The number of variables in regard to an individual prophylactic or treatment regimen is large, and a considerable range of doses is expected. The route of administration will also impact the dosage requirements. It is anticipated that dosages of the vaccine compositions will reduce growth of a tumor or other symptoms of the condition at least 10%, 20%, 30%, 40%, 50%, 60%, 70%, 80%, 90% or 100% compared to pre-treatment or progression of the disease if it was left untreated. It is specifically contemplated that pharmaceutical preparations and compositions may palliate or alleviate symptoms of the disease without providing a cure, or, in some embodiments, may be used to cure the disease or disorder.

Suitable effective dosage amounts for administering the vaccine compositions may be determined by those of skill in the art, but typically range from about $10^3$ cells to $10^{10}$ cells. The compound can be administered as a single dose or as divided doses. For example, the composition may be administered two or more times separated by a day, two days, three days, four days, one week, two weeks, three weeks or by four or more weeks.

Kits for generating a cellular vaccine composition are also provided herein. The kits may include at least one antigenic polypeptide or at least one polynucleotide encoding the at least one antigenic polypeptide, reagents to facilitate the uptake of the antigenic polypeptide or polynucleotide encoding the at least one antigenic polypeptide by the cells and/or reagents and equipment to collect, antigen load and/or administer the cells. The reagents and equipment may include cell suspension or elutriation buffers, gelatin or gelatin solutions in physiological buffers, sucrose or sucrose solutions, and elutriation chambers or systems. The kits may include instructions for collection and isolation of the cells, instructions for loading the antigen in the cells and/or instructions for harvesting and administering the cell-based antigen-loaded vaccines. The kits may further include antibodies for positive or negative selection such as CD14, CD66b, CD1, CD83 and CCR7 or other means of selecting against dendritic cells.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

EXAMPLES

Example 1

Monocyte Antigen Transfer to Dendritic Cells Induces Efficacious Anti-Tumor Immunity Abstract To date, tumor vaccines have shown poor efficacy in clinical trials. Importantly, such vaccines do not target the pathways by which endogenous CTL responses are generated. Based on evidence that CTL responses are induced by resident lymphoid organ dendritic cells (DC) that receive antigens from monocytes or their progeny, we tested the hypothesis that administration of antigen-loaded monocytes, with no further manipulation, will induce anti-tumor immune responses superior to those seen with conventional tumor vaccines. We find that monocytes loaded with either model or known tumor antigens induce robust antigen-specific $CD4^+$ and $CD8^+$ T cell responses in mice, display anti-tumor efficacy superior to that seen with dendritic cell vaccines, and can be combined with checkpoint blockade to further increase their efficacy. These monocyte-induced responses do not involve antigen presentation by monocytes, but rather the transfer of antigen to endogenous splenic DC. This transfer occurs via gap junctions for $CD8^+$ T cell responses and macrophages for $CD4^+$ T cell responses. We conclude that antigen-loaded monocytes effectively target and activate resident splenic DC for CTL induction via two distinct antigen transfer mechanisms and that this strategy may serve as a simple and efficacious immunotherapeutic platform for the treatment of human cancers.

Introduction

Despite increasingly sophisticated and targeted anti-cancer therapies, evidence suggests that the effective treatment of most tumors will require exogenous stimulation of anti-tumor T cell immunity (1). Unfortunately, stimulating effective anti-tumor T cell responses in the majority patients has proven difficult. A variety of tumor vaccination strategies that have shown promise in preclinical studies have now been examined in clinical trials. These strategies include vaccination with peptides, recombinant viruses, whole tumor cells, plasmid DNA, and ex vivo-generated dendritic cells (DC) (2-6). In the majority of patients, such strategies generate tumor-specific cytotoxic T cell (CTL) responses. However, objective response rates for all of these modalities remain low, at around 5%, and in very few cases are these modalities associated with increased patient survival (7).

Almost all current tumor vaccines are based on one of two strategies. They either deliver tumor antigens (Ags) to DC in the context of a DC-activating agent or they administer Ag-loaded DC that have been generated ex vivo. However, evidence suggests that neither of these strategies recapitulate the pathways by which endogenous CTL responses are actually generated, perhaps explaining their poor efficacy. The most effective CTL responses are generated by cross-priming, the process by which DC process exogenous Ags into the MHCI Ag presentation pathway to stimulate $CD8^+$ T cells (8, 9). Importantly, not all DC types can cross-prime $CD8^+$ T cells. In most cases, this function is performed by $CD8^+$ DC that are resident in lymphoid organs (9-11) and no current vaccine strategy specifically targets resident lymphoid organ DC. Subcutaneous or intradermal peptide, viral, whole tumor cell, and DNA vaccines target peripheral migratory DC and typically include adjuvants that have poor CTL immunogenicity. The ex vivo generation of DC results in a heterogeneous population of cells, of which, only a minority appear to be true DC and none have the phenotype of $CD8^+$ DC (12, 13).

We hypothesize that the administration of Ag-loaded monocytes would better recapitulate endogenous pathways of CTL generation and therefore stimulate CTL and anti-tumor immune responses that are more robust than seen with current tumor vaccines. Our rationale is as follows. Because lymphoid organ-resident DC do not patrol peripheral tissues, they must have Ags and activation signals delivered to them. Several lines of evidence suggest that monocytes and their progeny are the major cell types that perform this function in vivo (14). First, monocytes and macrophages are highly efficient at Ag capture. Monocytes have been shown to capture Ags in peripheral tissues for delivery to lymph nodes and are the only cell type in blood that effectively captures circulating viral antigens (15, 16). Second, monocytes, macrophages, and monocyte-derived DC efficiently transfer Ags to resident $CD8^+$ DC. Monocytes or their progeny have been shown to effectively transfer Ags to DC during contact sensitization (17), infection (18-21), the induction of oral tolerance (22), and after Ag phagocytosis (23, 24). In several models, monocyte or macrophage depletion results in loss of CTL responses (17, 18, 25). Third, cells of the monocyte lineage provide signals that are required for the development of effective T cell responses and are not provided by direct DC stimulation alone (26-28). Lastly and importantly, by differentiating into antigen presenting cells, monocytes may provide activities, such as the stimulation of T cell help, that further enhance CTL response (29).

Taken together, these studies strongly suggest that effective anti-tumor immune responses could best be generated by mimicking endogenous pathways of CTL generation and that endogenous CTL responses could be best mimicked using Ag delivery by monocytes, rather than traditional adjuvant or DC-based vaccines. Here, we test this hypothesis by examining the transfer of Ags from exogenously administered Ag-bearing monocytes to resident DC and the ability of this process to stimulate effective T cell and anti-tumor immune responses.

Results

Intravenously Injected Monocytes Induce Robust CD4+ and CD8+ T Cell Responses

Figure 1H:
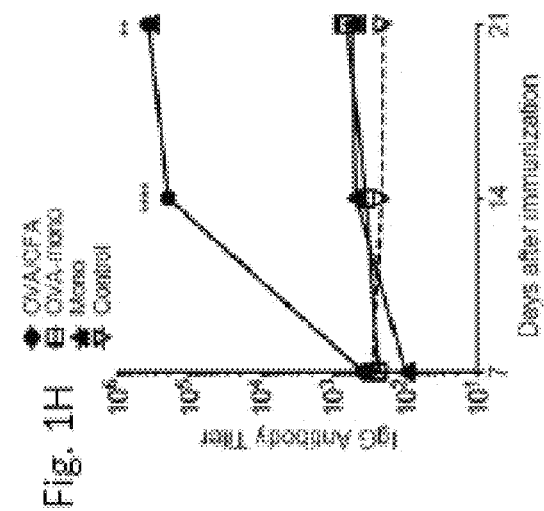
FIG. 1H is a graph showing the OVA-specific serum IgG titers after the indicated treatments. Control: naïve serum (N=1); other groups: N=3-4. Monocyte dose: $4\times10^6$ cells per mouse. D14:  $P<0.0001$; D21:  $P<0.01$ (compared to all the other groups; one-way ANOVA with Tukey's test). Data are representative of two independent experiments and presented as mean±s.e.m.
Figure 1G:
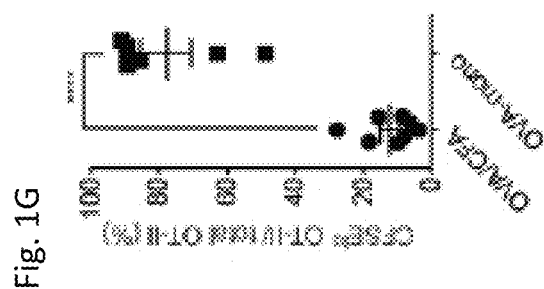
FIG. 1G is a graph showing proliferation of OT-II cells in spleens on Day 3 after the indicated treatments  $P<0.0001$ (unpaired two-tailed Student's t-test).

Based on the rationale outlined above, we reasoned that intravenous (IV) administration of antigen (Ag)-loaded monocytes would deliver Ag to resident splenic DC and thereby stimulate potent T cell responses. To test this hypothesis, we first determined that monocytes can be effectively loaded with ovalbumin protein (OVA), peptide ($OVA_{323-339}$) or RNA (FIG. 7A-I). We then examined T cell responses after IV administration of OVA protein-loaded monocytes. We find that a dose of $3\times10^6$ monocytes results in splenic CD8+ T cell expansion to an extent equal to that seen after SQ injection of OVA in Complete Freund's Adjuvant (CFA) (FIG. 1A,B). This dose was chosen based on initial titration studies (data not shown) and was used in all subsequent studies unless otherwise noted. Among activation markers, OVA protein-loaded monocytes induce the expression of T-bet, Eomesodermin and IFNγ in OVA-specific CD8+ T cells to a greater extent than OVA/CFA (FIG. 1C,D). Consistent with our hypothesis, OVA-loaded monocytes induce much greater CTL activity than OVA/CFA (FIG. 1E). However, this finding may result from favorable CD4+ T cell help induced by monocyte vaccination over OVA/CFA immunization. We detect robust OVA-specific CD4 T cell proliferation in the spleen by 64 hours after monocyte injection while OVA/CFA induces only a minimal CD4+ T cell response (FIG. 1F,G). In contrast to OVA/CFA, monocytes induce no OVA-specific IgG responses (FIG. 1H). Monocytes loaded with OVA RNA or $OVA_{323-339}$ also induce OVA-specific CD8+ or CD4+ T cell responses in the spleen (FIG. 8A,B). These findings demonstrate that IV injection of Ag-loaded monocytes, in the absence of any further stimulation, induce strong Ag-specific CTL and CD4+ T cell responses without triggering humoral immunity.

IV Injected Monocytes Preferentially Induce T Cell Responses in the Spleen

Figure 2C:
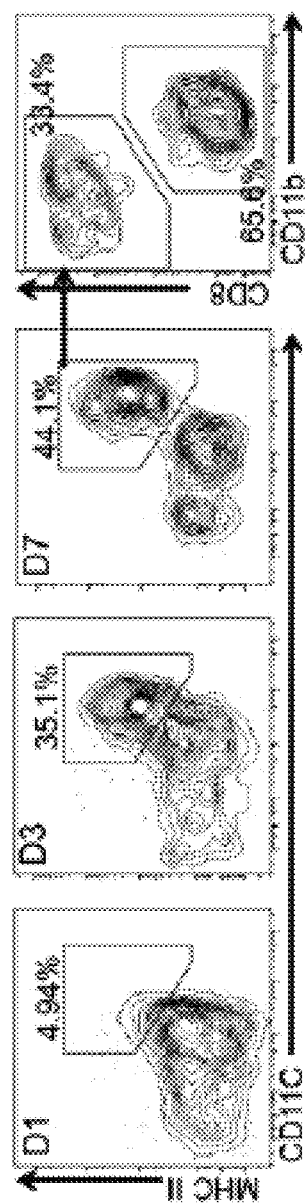
Figure 2D:
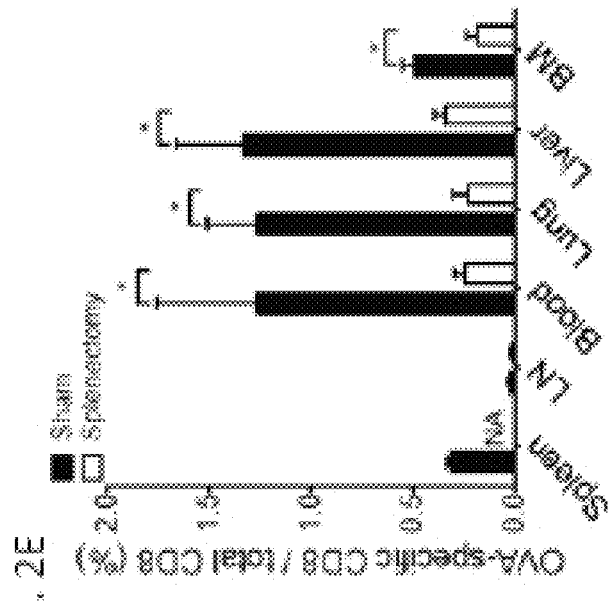
Figure 2E:
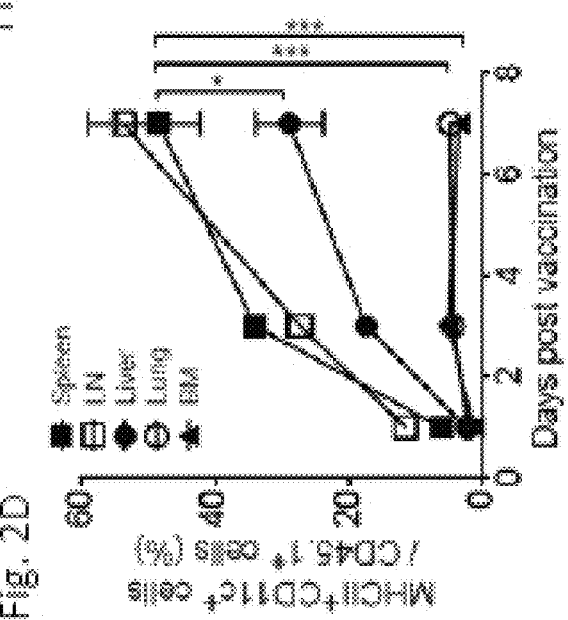
FIG. 2E is a graph showing the frequency of OVA-specific CD8 T cells across different tissues on D7 post IV OVA-loaded monocyte injection ($4 \times 10^6$ per mouse) into sham-operated or splenectomized mice. N=4 per group. * P<0.05 (Mann-Whitney test). LN: pool of bilateral inguinal and popliteal lymph nodes. BM: bone marrow from right femoral bone. Data are representative of two independent experiments and presented as mean±s.e.m.

In the above studies, monocytes may be inducing T cell responses by transferring Ag to DC or by presenting Ag to T cells directly after differentiating into DC. In either case, this may occur in a number of potential sites. To determine the fate of IV injected monocytes, we injected CD45.1 OVA-loaded monocytes into CD45.2 mice and tracked their numbers and phenotype over time. On day 1 post injection, CD45.1+ donor cells are found in significant numbers in the liver, spleen, lungs, bone marrow, and, to a lesser extent, lymph nodes (FIG. 2A). The number of donor cells in these organs decreases rapidly over 7 days, with the highest persistence of cells seen in the spleen (FIG. 2A; FIG. 9). Donor monocytes rapidly lose expression of Ly-6C (FIG. 2B). In spleen, lymph nodes, and, to a lesser extent, liver, a significant portion of donor monocytes increase expression of MHCII and CD11c, consistent with differentiation into DC (FIG. 2C,D). To determine where injected monocytes may be stimulating T cells, we examined the expansion of OVA-specific CD8+ T cells in the course of the above studies. Seven days post monocyte injection, the largest numbers of OVA-specific T cells are found in the spleen, followed by the lungs and liver, with minimal expansion seen in the bone marrow and lymph nodes (FIG. 2A). These findings suggest that IV injected monocytes activate T cells primarily in the spleen. To confirm this, we administered OVA-loaded monocytes to splenectomized mice and examined the frequency of OVA-specific CD8+ T cells in multiple organs and blood. Relative to sham-operated mice, splenectomized recipients display a >75% decrease in CD8+ T cell frequency in blood and almost all organs on day 7 (FIG. 2E).

IV Injected Monocytes Stimulate T Cells Indirectly

Figure 10C:
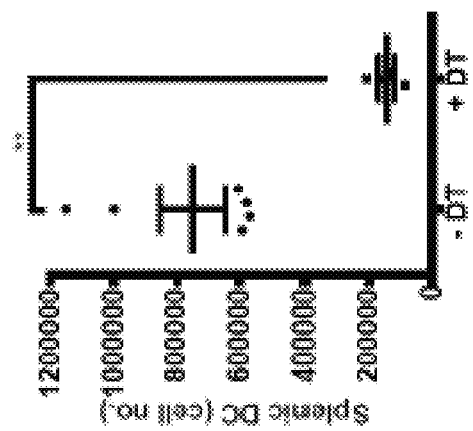
FIG. 10C shows the schematic experimental design of FIG. 10D and FIG. 3C.
Figure 10D:
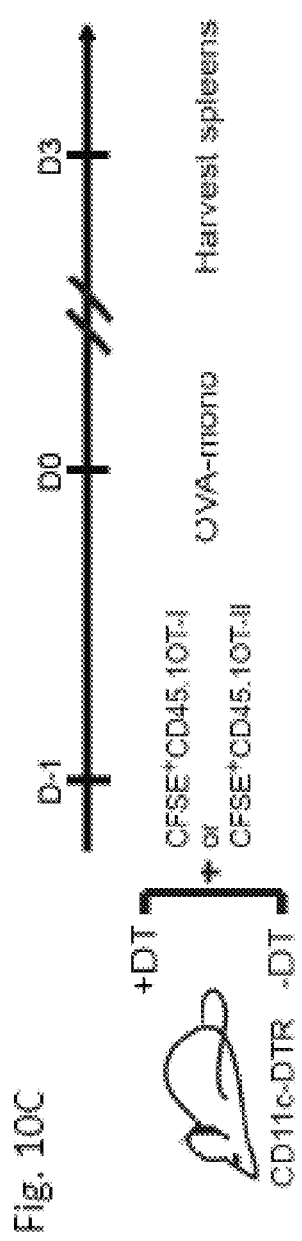
FIG. 10D shows representative contour plots showing percentages of DCs among total endogenous splenocytes in DT-untreated (left) and DT-treated (right) CD11c-DTR mice.
Figure 10E:
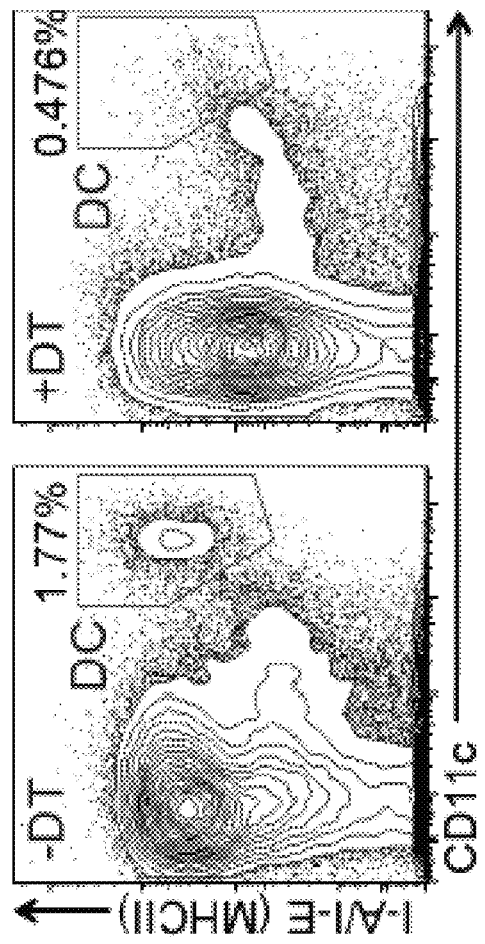
FIG. 10E is a graph and statistics derived from FIG. 10D. Data are presented as mean±s.e.m.  P<0.01; * P<0.001; **** P<0.0001 (unpaired two-tailed Student's t-test).
Figure 11A:
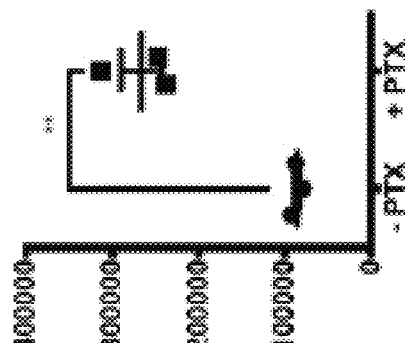
FIGS. 11A and 11B are graphs and statistics showing frequency of injected monocytes among total CD45$^+$ splenocytes (FIG. 11A) and absolute numbers of injected monocytes (FIG. 11B) in the spleen on D1 post IV OVA-loaded monocyte injection ($4×10^6$ per mouse).
Figure 11B:
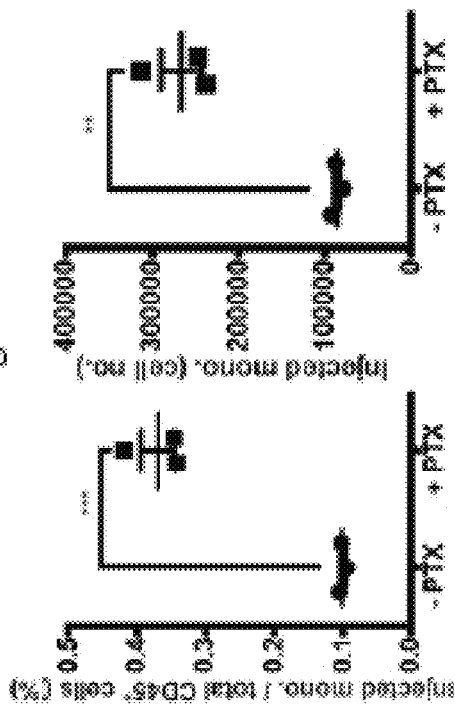
Figure 11D:
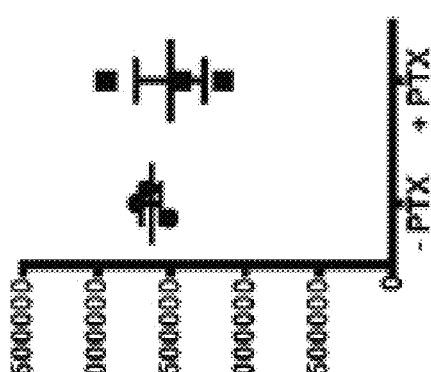
FIGS. 11D and 11E are graphs and statistics showing frequency of endogenous DCs among total splenocytes (FIG. 11D) and absolute numbers of endogenous splenic DCs (FIG. 11E) on D1 post IV OVA-loaded monocyte injection ($4×10^6$ per mouse). Data are presented as mean±s.e.m.  P<0.01; * P<0.001 (unpaired two-tailed Student's t-test).
Figure 11E:
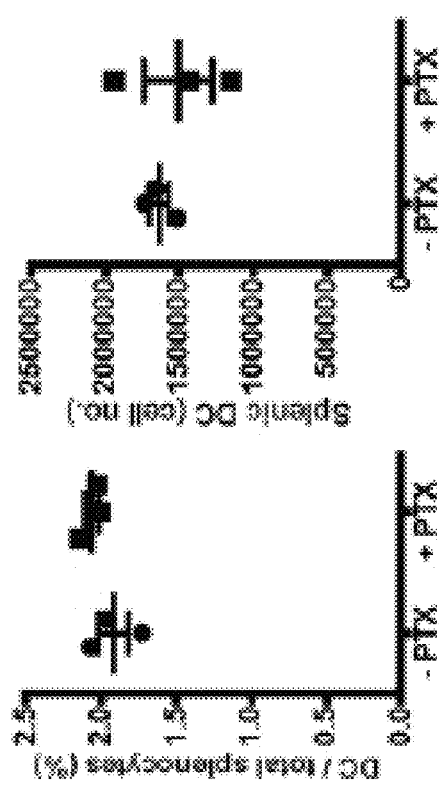

To determine whether IV injected monocytes are directly activating T cells in the spleen or are activating T cells indirectly via Ag transfer, we loaded either MHCI- or MHCII-deficient monocytes with OVA protein, injected these into wild-type mice, and examined T cell responses. We find that the lack of MHC molecules on injected monocytes leads to no decrease in the expansion of OVA-specific CD8+ T cells (FIG. 3A). To confirm that T cell responses are dependent on Ag presentation by recipient cells, we injected wild-type OVA-loaded monocytes into MHCI-deficient mice that had received OT-I cells via adoptive transfer. OVA-specific CD8+ T cell responses are significantly reduced in these mice (FIG. 3B; FIG. 10A,B). In addition, both CD4+ and CD8+ Ag-specific T cell responses are almost completely eliminated when recipient DC are depleted by injecting CD11c-DTR recipient mice with diphtheria toxin prior to monocyte vaccination (FIG. 3C,D; FIG. 10C-E). These findings strongly suggest that IV injected monocytes do not activate T cells directly, but instead, transfer Ag to endogenous splenic DC, which then present that Ag to T cells. To determine if this phenomenon could be recapitulated in vitro in the human system, we co-cultured human monocytes and CFSE-labeled T cells obtained from CMV-seropositive donors in the presence or absence of autologous monocyte-derived DC. Monocytes were either naïve or transfected with CMV pp65 RNA. T cells cultured with naïve monocytes do not proliferate under any conditions (FIG. 3E,F). In contrast, T cells cultured with pp65-loaded monocytes proliferate in a manner dependent on monocyte number, but only in the presence of DC (FIG. 3E,F). This finding supports that Ag-loaded human monocytes also stimulate T cells indirectly by transferring antigens to DC.

Monocytes Stimulate Splenic CD4+ and CD8+ T Cells Via Different Pathways

The finding that monocytes transfer Ag to DC suggested that these two cell types must be in physical proximity. We speculated that this may require the activity of specific chemokines acting on monocytes. However, OVA-loaded monocytes lacking either CCR7 or both CCR2 and CCR7 retain their ability to induce OVA-specific CD8+ T cell responses (FIG. 4A). To more globally inhibit monocyte chemokine receptor activity, we pre-treated monocytes with pertussis toxin (PTX), which is known to block all Gαi-mediated receptor signaling (30, 31). PTX-treated monocytes fail to stimulate endogenous OVA-specific CD8+ T cell responses as assessed by tetramer staining (FIG. 4B,C). Consistent with this, the proliferation of adoptively transferred CD8+ OT-I T cells is severely impaired in the mice receiving PTX-treated monocytes (FIG. 4D,E). However, upon examining monocyte numbers and distribution in spleens on day 1 post IV monocyte injection, we found PTX actually increased the accumulation of monocytes in the spleen and had no effect on either the distribution pattern of monocytes in the spleen or the total number of endogenous splenic DC (FIG. 11A-E). Surprisingly, in contrast to CD8+ T cells, the proliferation of OVA-specific CD4+ OT-II T cells is not inhibited by PTX treatment of monocytes (FIG. 4D,E). This finding provided an initial clue that monocytes stimulate splenic CD4+ and CD8+ T cells via different mechanisms, which may involve the transfer of MHCI and MHCII antigens via different pathways. This phenomenon is examined in more detail below.

Gap Junctions are Required For Monocyte-to-DC Antigen Transfer to Activate $CD8^+$ T Cells In the above studies, the impairment of $CD8^+$ T cell responses when monocytes are treated with PTX did not appear to be due to the inhibition of chemokine function. We therefore considered two other potential antigen transfer mechanisms that are known to be PTX-sensitive: the production of exosomes and the function of gap junctions. Both these phenomenon require $G\alpha_i$ activity (32)(33), are known to mediate Ag transfer between cells, and have been described in monocytes and DC (34-39). One key difference in these mechanisms is that Ag transfer via gap junctions is dependent on cell-cell contact, while transfer via exosomes is not (35, 36). We therefore determined if cell-cell contact is required for the transfer of antigens from MHCI-deficient monocytes to DC using in vitro transwell assays. Similar to FIG. 3e above, we find that co-culturing OVA-loaded monocytes with DC and CFSE-labeled OT-I cells results in robust T cell proliferation (FIG. 5A). However, when monocytes are separated from the other cell types by a transwell membrane, T cell proliferation does not occur (FIG. 5A), suggesting that MHCI antigen transfer from monocytes to DC is cell contact-dependent. Of note, in contrast to OT-I cells, co-culturing OVA-loaded MHCII-deficient monocytes with DC and CFSE-labeled OT-II cells does not result in $CD4^+$ T cell proliferation (FIG. 5A), a point we will discuss further below.

Figure 12:
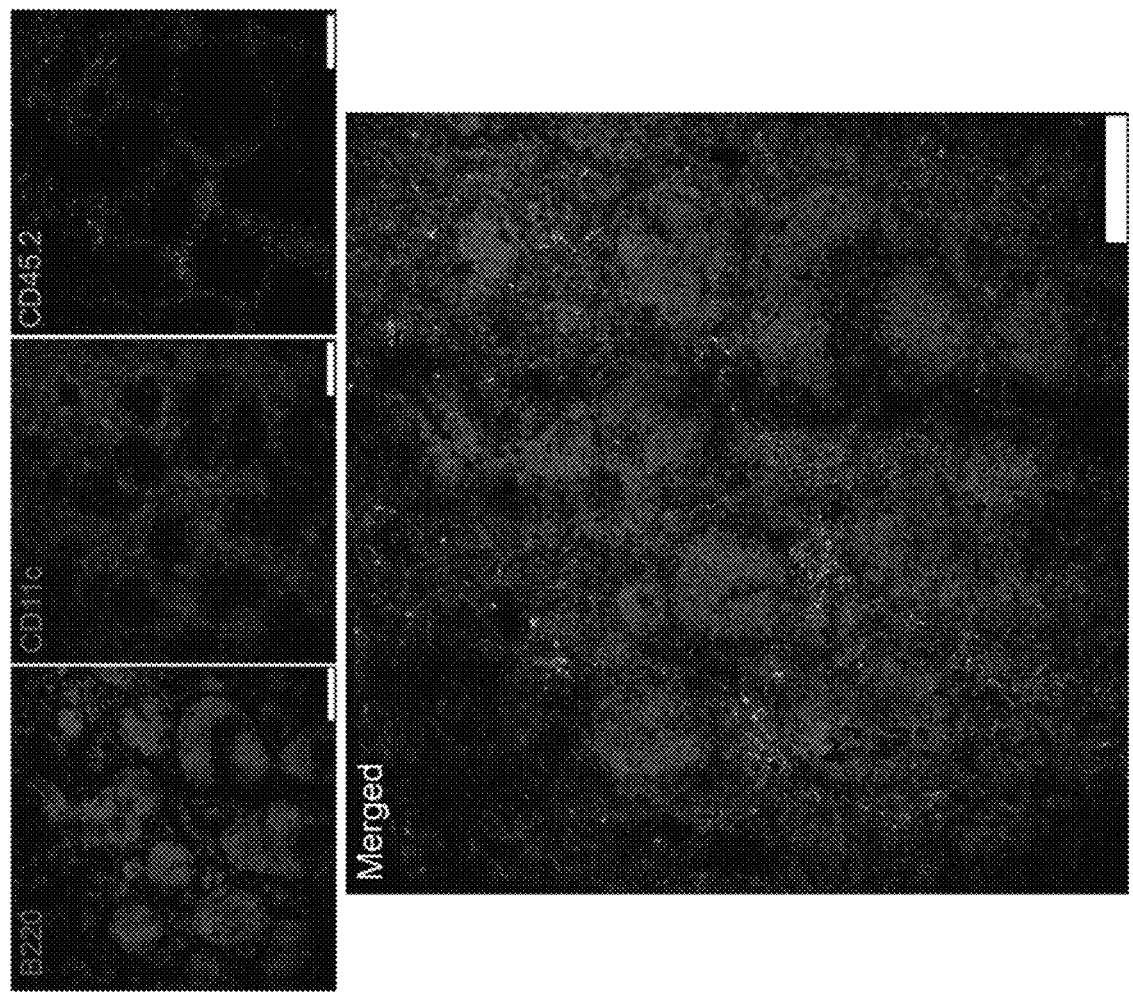
FIG. 12 shows in vivo interaction between injected monocytes and splenic DCs. Immunoflurescent staining of spleen sections on D1 post IV OVA-loaded monocyte (CD45.2) injection. Recipients are CD45.1 mice. B220: B cells. CD11c: DCs. CD45.2: injected monocytes. Scale bar: 250 µm.

We next determined if monocytes actually form stable interactions with DC. When monocytes and DC are co-cultured in vitro, these cells form prolonged cell-cell contacts lasting at least 2 hours (FIG. 5B). Similarly, staining of spleen sections prepared from the mice injected with OVA-loaded monocytes, whether pretreated with PTX or not, reveals that half of the injected monocytes form direct contacts with DC (FIG. 5C,D; FIG. 11C,FIG. 12). Based on these studies, we conclude that MHCI antigen transfer from monocytes to DC is cell contact-dependent and therefore not mediated by exosomes.

Figure 5H:
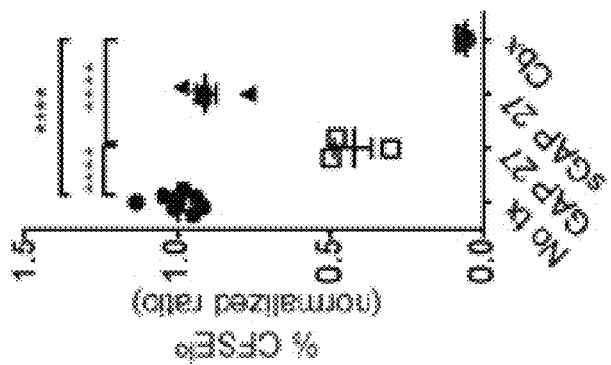
FIG. 5H is a graph showing proliferation of OT-I cells cultured with OVA-loaded monocytes and splenic DC in the presence of a Cx43 inhibitory peptide (GAP27), the scrambled GAP27 peptide (sGAP27), or carbenoxolone (Cbx).  P<0.0001 (one-way ANOVA with Tukey's test).
Figure 5E:
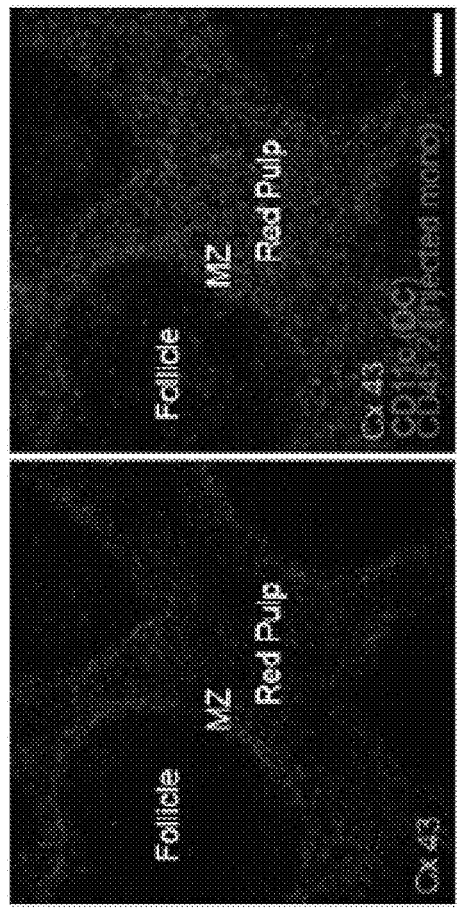
FIGS. 5E-5G are photographs of localization of connexin 43 (Cx43, arrows) relative to donor CD45.2$^+$ OVA-monocytes and recipient splenic DC 1 day post injection. MZ: marginal zone.
Figure 5G:
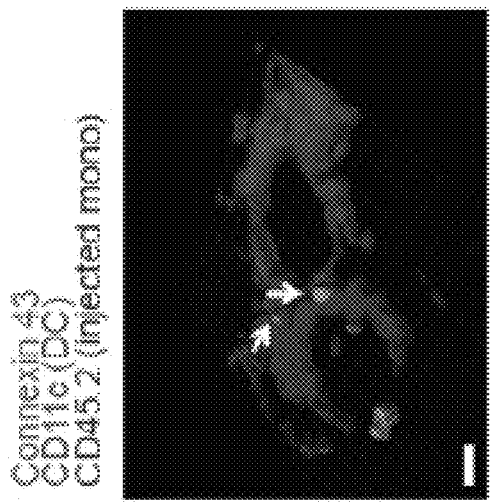
Figure 5D:
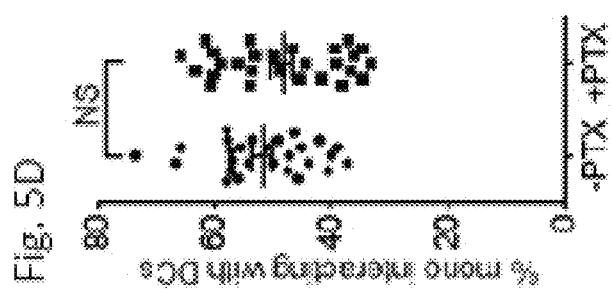
FIG. 5D is a graph showing the percentage of PTX-untreated (−PTX) and treated (+PTX) donor monocytes interacting with DC. N=27 fields from 3 mice per group. NS: non-significant (unpaired two-tailed Student's t-test).
Figure 5F:
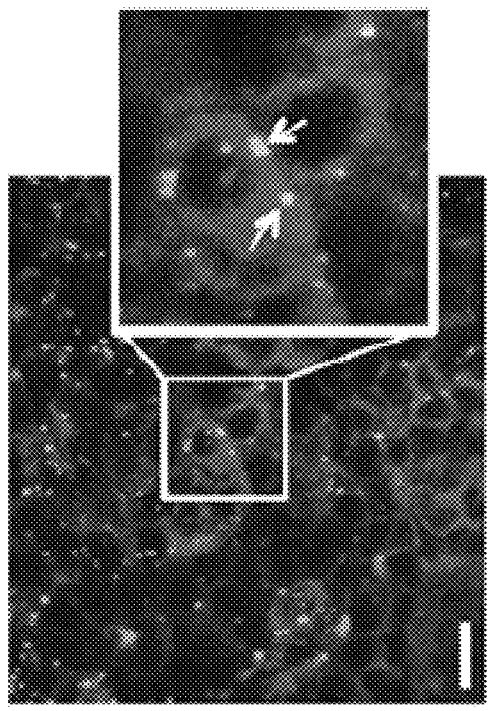
Figure 13:
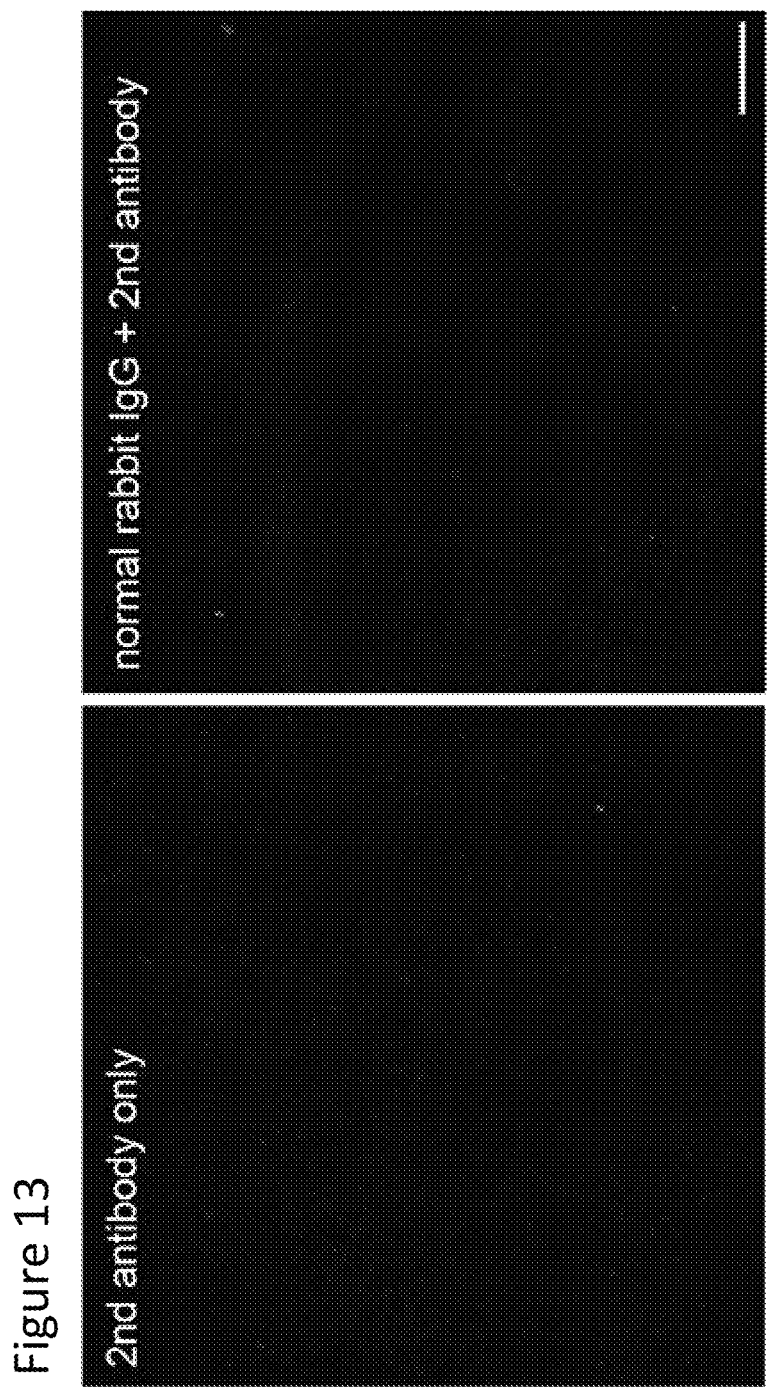
FIG. 13 shows control staining of connexin 43 on splenic tissue sections. Control staining of connexin 43 was performed with secondary antibody alone (left) or with normal rabbit IgG as primary antibody plus secondary antibody (right). Scale bar: 100 µm.
Figure 15A:
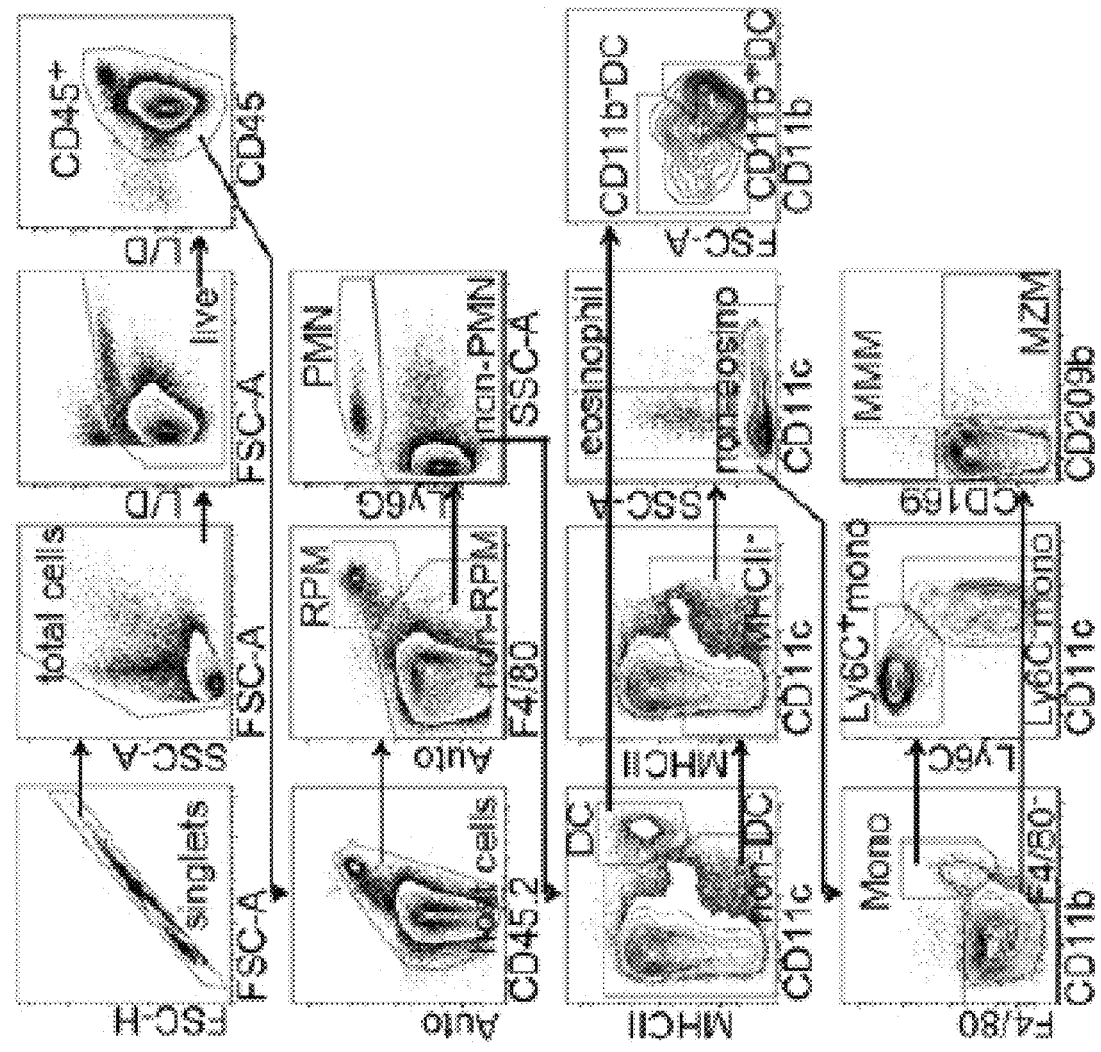
FIG. 15A shows the gating strategy used to define the cell types shown in FIGS. 15B-15F.
Figure 15C:
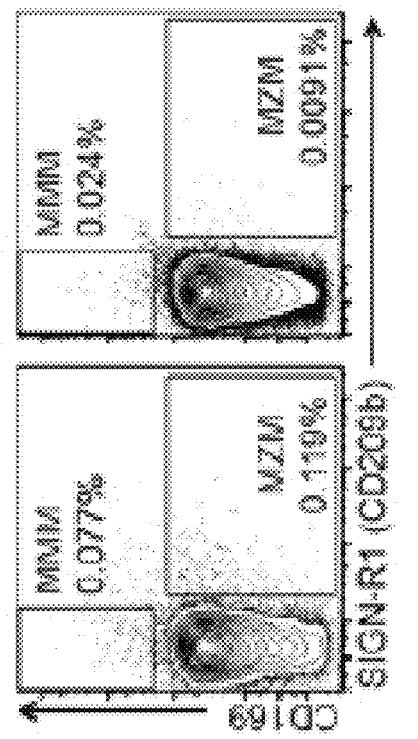
FIG. 15C shows representative flow plots showing percentages of marginal zone macrophages (MZM) and marginal metallophilic macrophages (MMM) among total live splenocytes.
Figure 15B:
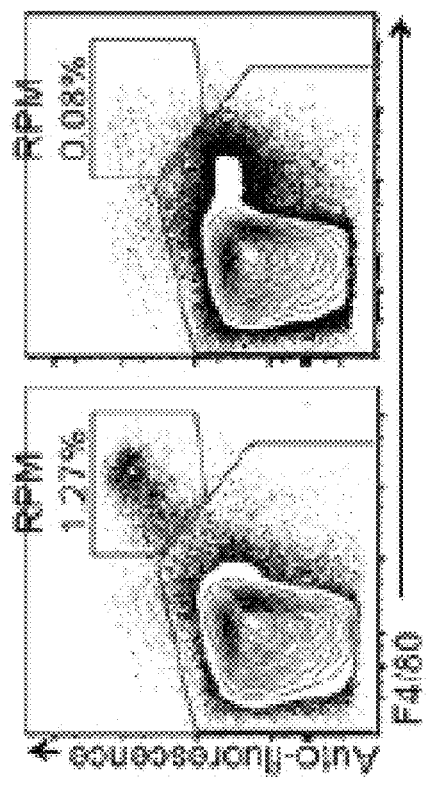
FIG. 15B shows representative flow plots showing percentages of red pulp macrophages (RPM) among total live splenocytes.
Figure 15D:
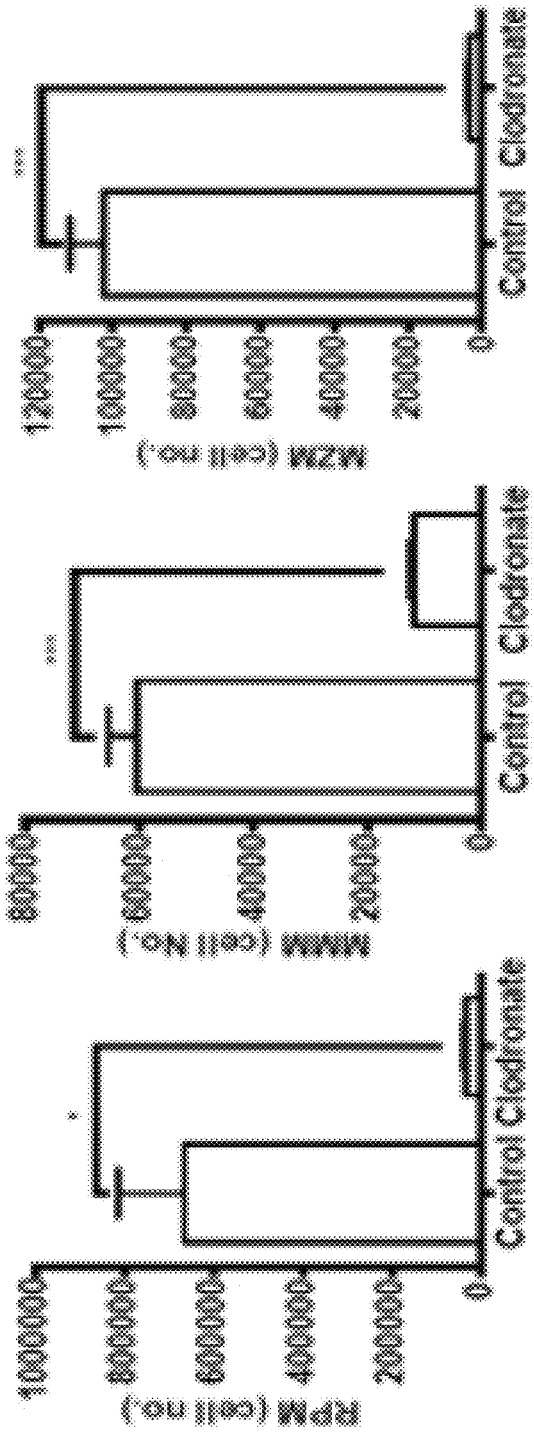
FIG. 15D shows graphs and statistics derived from FIGS. 15B and 15C. N=5 per group.

Gap junctions between cells are formed by two hexameric hemichannels (connexons) comprised of connexin (Cx) proteins(35). Among Cx proteins, Cx43 is the most widely distributed and known to be expressed on monocytes and splenic DC(22, 35). We find that the distribution of Cx43 in the spleen is noticeably skewed toward marginal zones (FIG. 5E; FIG. 13) where monocyte-DC interactions are frequent and that it appears at contact points between monocytes and DC (FIG. 5E-G; FIG. 11C, FIG. 12). In co-cultures of OVA-loaded MHCI-deficient monocytes, splenic DC, and OT-I cells, addition of the selective Cx43 inhibitor peptide Gap27 (40) or the non-specific gap junction blocker carbenoxolone (41) significantly reduces or abrogates OT-I cell proliferation while a scrambled Gap27 peptide (sGAP27) has no effect (FIG. 5H). To determine if gap junctions are required for MHCI antigen transfer in vivo, we crossed CD11c-Cre mice with Cx43 gene (Gja1) floxed mice, resulting in the complete loss of Gja1 RNA expression in splenic DC (FIG. 14A). This resulted in no change in splenic DC numbers or antigen presenting capacity (FIG. 14B-F). However, OVA-specific $CD8^+$ T cell proliferation is significantly reduced in CD11c-CreGja1$^{f/f}$ mice injected with OVA-loaded monocytes (FIG. 5I,J). We conclude that gap junctions mediate MHCI antigen transfer from monocytes to splenic DCs.

MHCII Antigen Transfer from Monocytes to DC is Macrophage-Dependent

As noted above, unlike OT-I cells, the proliferation of OVA-specific $CD4^+$ OT-II T cells is not inhibited by PTX treatment of monocytes (FIG. 3D,E), suggesting that MHCII antigens are not transferred from monocytes to DC via gap junctions. Consistent with this, OVA-specific $CD4^+$ T cell proliferation induced by OVA-loaded monocytes is not impaired in CD11c-CreGja1$^{f/f}$ mice (FIG. 5K). Moreover, while $CD4^+$ T cells responses require recipient DC in vivo (FIG. 3C,D), co-culturing OVA-loaded MHCII-deficient monocytes, splenic DC, and OT-II cells does not result in OT-II cell proliferation (FIG. 5A), suggesting that an additional cell type is required. Because previous studies have suggested that marginal zone and red pulp macrophages are involved in antigen processing (42), we speculated that splenic macrophages might be required for $CD4^+$ T cell responses. We therefore used liposome-clodronate to deplete splenic macrophages in mice prior to IV co-transfer of OT-I and OT-II cells and injection of OVA-loaded monocytes (FIG. 15A-D). In these mice, OT-II proliferation is severely impaired while OT-I proliferation remains intact (FIG. 5L,M). Although clodronate treatment depleted about 30% of splenic DC, this depletion was not DC subset-specific (FIG. 15E,F) and would not account for the differential responses of $CD4^+$ and $CD8^+$ T cells to monocyte injection. We thus conclude that MHCII antigen transfer from monocytes to splenic DC is a macrophage-dependent process.

Monocyte Vaccination Induces Anti-Tumor Responses Better than DC Vaccines

The above findings demonstrate that IV injection of Ag-loaded monocytes results in the efficient delivery of Ag to resident splenic DC and the induction of robust $CD4^+$ T cell and CTL responses. As noted above, we believe that this recapitulates the pathway by which most endogenous CTL responses are generated. For this reason, we thought it possible that monocyte administration could induce anti-tumor responses more effectively than current tumor vaccine strategies. To test this, we compared IV monocytes with an optimized DC vaccination protocol in a melanoma model in which mice are injected SQ with OVA-transfected B16F10 melanoma cells. This DC vaccination protocol, which we have used previously, involves adoptive OT-I T lymphocyte transfer (ALT), preconditioning the vaccine site with tetanus/diphtheria (Td) toxoid, then 3 intradermal injections of Ag-loaded DC (43). We find that 3 doses of $10^6$ OVA protein-loaded monocytes, administered without ALT beginning eight days after tumor inoculation, inhibits tumor growth as effectively as the DC vaccine administered with ALT (FIG. 6A). Moreover, a single dose of $3 \times 10^6$ monocytes markedly inhibits tumor growth, while 3 doses of the DC vaccine administered in the absence of ALT fails to inhibit tumor growth to any detectable extent (FIG. 6B). Monocytes also induce robust memory responses, as tumor growth is significantly inhibited and survival is significantly increased when mice are inoculated with melanoma cells 42 days after IV monocyte administration (FIG. 6C,D).

Checkpoint blockade has proven to be a remarkably effective tumor immunotherapeutic strategy in some patients. Combining checkpoint blockade with tumor vaccines has been advocated as a promising strategy to improve their efficacy (44). To determine if checkpoint blockade can improve the anti-tumor efficacy of monocyte vaccination, we examined the effects of administering anti-CTLA4, anti-PD-1 or anti-PD-L1 antibodies in combination with OVA-loaded monocytes in the B16F10-OVA tumor model. For these studies, the dose of monocytes was reduced to a single administration of 2×10⁶ cells. In this model, anti-CTLA4 alone has no effect on tumor growth, but in combination with monocyte vaccination results in significantly improved tumor growth inhibition over administration of monocytes alone (FIG. 6E). Similarly, both anti-PD-1 and anti-PD-L1 antibodies, which display some anti-tumor efficacy by themselves, significantly improve monocyte vaccine efficacy (FIG. 6F,G).

To determine if monocyte vaccination is efficacious when used with a true endogenous tumor Ag, we tested monocytes loaded with the major CTL epitope of Tyrosinase-related Protein 2 ($TRP2_{180-188}$), a known B16 melanoma Ag, in the B 16F10 melanoma model (45). For these studies, mice received 6 doses of 1×10⁶ monocytes. Six IV injections of $TRP2_{180-188}$-loaded monocytes markedly inhibit tumor growth and significantly prolong survival of B16-F10 melanoma tumor-bearing mice with a more than 30% long-term survival rate (FIG. 6H,I). To test a second endogenous tumor Ag, we examined the efficacy of monocytes loaded with mutant (R132H) isocitrate dehydrogenase 1 (mIDH1) peptide in a model of aggressive intracranial glioblastoma (GBM). Mutant IDH1 is seen as a promising tumor vaccine target due to its widespread expression on low-grade gliomas and its suggested function as a driver mutation (46, 47). However, mIDH1 peptides have proven to be very poorly immunogenic. Mutant IDH1 DC vaccines have not shown efficacy in our hands and, to our knowledge, anti-tumor responses have only been seen with peptide/CFA immunization (47). For these studies, mice were intra-cranially injected with mIDH1-transfected CT-2A astrocytoma tumor cells (48) and, 3 days later, treated with either anti-PD-1 alone or anti-PD-1 plus a single IV injection of mIDH1 peptide-loaded monocytes. Mice treated with anti-PD-1 alone demonstrate no survival benefit; however, mice treated with anti-PD-1 plus mIDH1-loaded monocytes display significantly improved survival, with 25% of treated mice surviving long term (FIG. 6J).

Discussion

In this study, we tested the hypothesis that using a vaccine strategy that mimics an endogenous pathway of CTL induction, namely the cell-mediated delivery of Ag to resident splenic DC, would generate immune responses superior to those seen with more conventional vaccines. Our results demonstrate that, for the responses we examined, this hypothesis is correct. We find that IV injection of Ag-loaded monocytes stimulates remarkably strong CD4⁺ T cell, CTL, and anti-tumor immune responses in mice. Monocyte administration stimulates stronger T cell responses than those seen with protein/CFA immunization, especially in terms of CTL activity. The anti-tumor responses induced by monocyte injection are far stronger than we have been able to achieve using DC vaccination with the same Ags. In our view, these results are not surprising, as neither SQ immunizations nor monocyte-derived DC administration would be expected to specifically target or recapitulate the activity of the resident DC populations that most commonly induce endogenous CTL responses.

We chose to use monocytes as our Ag delivery vehicle based on the large number of studies demonstrating that monocytes and their progeny can efficiently transfer Ag to resident DC (17-24) and the evidence suggesting that monocytes perform this function in many endogenous CTL responses (14). The true extent to which monocytes are responsible for endogenous CTL induction in vivo remains an open question. However, our findings, when compared with previous studies, suggest that monocytes perform this function more effectively than other cell types. The induction of CTL responses has been examined after the administration of several Ag-loaded cell types including lymphocytes, whole blood cells, and total splenocytes (49-51). In each of these cases, administration of greater than 10⁷ cells is required to generate effective CTL responses, while we were able to induce robust CTL responses using about 10-fold fewer monocytes. It is not presently clear if this increased potency of monocytes relative to other cell types in stimulating CTL responses is due to more efficient Ag transfer or if monocytes provide specific signals to DC that other cell types do not.

The transfer of Ags from monocytes or macrophages to DC has been found to occur by several different mechanisms including peptide transfer via gap junctions, microparticles or exosomes, and transfer of MHCI/peptide complexes (18, 22-24). Here, we find that the transfer of Ags from monocytes to DC occurs by two distinct mechanisms that differ depending on the type of Ag that is being transferred. The transfer of MHCI Ags requires direct cell-cell contact and the formation of Gap junctions between monocytes and DC. Gap junction mediated transfer of MHCI Ags is a well-recognized phenomenon. The transfer of immunogenic MHCI Ags between adjacent tumor cells (34), tumor cells and monocyte-derived cells (34), tumor cells and DC (39), and between human DC (52), has been shown to require Gap junctions. In contrast, we find that MHCII Ag transfer to endogenous DC is not Gap junction dependent but rather requires the presence of macrophages. This may be due to the fact that MHCII Ags are typically too large for effective Gap junction transfer, as only molecules less than 1.2 KDa (~11 amino acids) can be transferred through Gap junctions (35). Alternatively, Gap junction transfer may not target Ags to the MHCII presentation pathway. Although in a murine oral tolerance model, gap junctions mediate MHCII Ag transfer by facilitating exchange of membranes with their associated peptide-MHCII complexes between monocyte-derived intestinal macrophages and DC (22), our finding that monocytes still transfer MHCII Ag to Cx43-deficient splenic DC and activate CD4 T cells is not consistent with this mechanism. The exact role that macrophages play in MHCII Ag transfer has yet to be determined. We speculate this process might involve dead Ag-carrying monocytes being phagocytosed by macrophages, which then relay the Ags to splenic DCs in proximity. The fact that monocytes use multiple Ag-transfer pathways may explain their efficiency in inducing CTL responses. In addition, the specific Ag-transfer pathways used by monocytes may account for the absence of antibody responses, which are seen after administration of other Ag-loaded cell types (50).

Our results also raise the possibility that the administration of Ag-loaded monocytes could be used in the treatment of human cancers. Our results in mice suggest that monocyte vaccination in humans may display greater efficacy than current tumor vaccine strategies. Numerous approaches have been proposed to enhance cross-priming and thereby improve tumor vaccine efficacy (53, 54). Our findings suggest that this can be best accomplished by mimicking endogenous mechanisms of CTL induction and that monocyte administration is an effective means to achieve this. Administration of Ag-loaded monocytes offers other potential advantages as a tumor vaccine platform. It is extremely simple, requiring no activation, stimulation, or differentiation of monocytes beyond Ag loading. Also, monocyte vaccination is rapid. Large numbers of high purity human monocytes can be obtained within a few hours (55, 56), with an additional 1-2 hours required for loading or transfecting monocytes with Ags. This means that monocyte vaccination could be performed in clinical settings in a single day. In terms of cost and feasibility, this represents a substantial improvement over DC vaccines. Monocytes can also be easily transfected or electroporated with mRNA, allowing simultaneous vaccination with multiple tumor antigens. In addition, our findings demonstrate that that monocyte vaccination may be combined with checkpoint blockade to further enhance its therapeutic efficacy. In summary, we conclude that monocyte vaccination induces robust T cell and anti-tumor immune responses in mice and has the potential to provide greater efficacy than current tumor vaccines in humans while being simple, inexpensive, and feasible for routine clinical use.

Methods

Mice, drugs and tumor cell lines. C57BL/6 wild-type mice were purchased from Charles River. Splenectomized and sham-operated C57BL/6, CD11c-DTR (B6.FVB-Tg(Itgax-DTR/EGFP)57Lan/J), CD45.1, OT-I, OT-II, Gja1$^{f/f}$ (B6.129S7-Gja1tm1Dlg/J), CD11c-cre (B6.Cg-Tg(Itgax-cre)1-1Reiz/J), B$_2$m$^{-/-}$ (B6.129P2-B2mtm1Unc/J), MHCII$^{-/-}$ (B6.129S2-H2dlAb1-Ea/J). Ccr2$^{-/-}$ (B6.129S4-Ccr2tm1Ifc/J) and Ccr7$^{-/-}$ (B6.129P2(C)-Ccr7tm1Rfor/J) mice were from The Jackson Laboratory. Ccr2$^{-/-}$ Ccr7$^{-/-}$ mice were generated by the crossing of CCR2$^{-/-}$ to CCR7$^{-/-}$ mice. OT-ICD45.1 and OT-IICD45.1 mice were generated from the crossing of CD45.1 to OT-I and OT-II mice respectively. CD11c-creGja1$^{f/f}$ mice were generated from the crossing of CD11c-cre to Gja1$^{f/f}$ mice. Anionic liposomal clodronate (Clophosom-A; FormuMax) was given 100 µl (=0.7 mg of clodronate) per mouse by intraperitoneal (i.p.) injection to deplete macrophages in vivo up to one week. Diphtheria toxin (DT; Sigma) was injected i.p. at a dose of 100 ng per mouse to deplete DCs in CD11c-DTR mice for a week. All of the mice were bred and maintained in specific pathogen-free (SPF) condition and used for experiments between 6 and 12 weeks old. All the experiments were performed under the approval of the Institutional Animal Care and Use Committee of Duke University. The B16/F10 and B16/F10-OVA tumor cell lines were kind gifts from R. Vile, PhD (Mayo Clinic)(57, 58). The CT-2A-mutant IDH1-R132H (CT-2A-mIDH1-R132H) cell line was provided by Vidyalakshmi Chandramohan, PhD. To generate this tumor cell line, the mouse IDH1-R132H cDNA was cloned into pLenti6.2 construct (Life Technologies). Lentivirus expressing mIDH1-R132H cDNA was generated in HEK293 cells. CT-2A cells were infected with the mIDH1-R132H lentivirus and stable clones were selected with Blasticidin. CT2A-mIDH1-R132H clone was further validated by western blot for mIDH1-R132H protein expression and by measurement of D-2HG by liquid chromatography/tandem mass spectrometry (LC/MS-MS). Tumor cell lines were tested mycoplasma free before use.

Antibodies and the tetramer. The antibodies used for mouse monocyte purification are specific to CD3ε (eBio500A2), CD4 (GK1.5), CD8α (53-6.7), CD19 (MB19-1), B220 (RA3-6B2), CD49b (DX5), TER-119 (TER-119; all from eBioscience); CD11c (HL3), Ly-6G (1A8), I-A$^b$ (AF6-120.1), Sca-1 (E13-161.7), c-Kit (2B8; all from BD Pharmingen); and CCR3 (83101; R&D). Anti-Ly-6G and anti-CCR3 are FITC-conjugated and all the others are biotinylated. For mouse cell phenotyping and FACS cell sorting, the antibodies conjugated to FITC, PE, PE-Cy5.5, PE-Cy7, Allophycocyanin, eFluor 660, Allophycocyanin-Cy7, Brilliant Violet 421, V450, Pacific Blue, Alexa Fluor 700, eFluor 605NC, Brilliant Violet 605, Brilliant Violet 650, eFluor 650NC, Brilliant Violet 711 or Brilliant Violet 786 and specific to the following mouse antigens were used: CD3ε (145-2C11), CD4 (GK1.5 or RM4-5), CD14 (Sa14-2), CD25 (PC61), CD44 (IM7), CD45 (30F-11), CD45.2 (104), CD115 (AFS98), CD169 (3D6.112), B220 (RA3-6B2), F4/80 (BM8), IFN$_γ$ (XMG1.2; all from BioLegend); CD8α (53-6.7), CD11c (N418), CD19 (eBio1D3), CD49b (DX5), CD86 (GL1), CD209b/SIGN-R1 (eBio22D1), F4/80 (BM8), NK1.1 (PK136), I-A/I-E (M5/114.15.2), Eomes (Dan11mag), Granzyme B (NGZB), T-bet (eBio4B10; all from eBioscience); CD11b (M1/70), CD40 (3/23), CD45.1 (A20), CD62L (MEL-14), Ly-6C (AL-21), Ly-6G (1A8), Vα2 (B20.1; all from BD Pharmingen). Isotype control antibodies were from the corresponding sources. Anti-mouse CD16/32 (93; functional grade, eBioscience) was used for Fc$_γ$R blocking. Anti-mouse PD-1 (RMP1-14), anti-mouse PD-L1 (10F.9G2) and anti-mouse CTLA-4 (9H10) for checkpoint blockade treatment and the isotype-matched control antibodies were from Bio X Cell. PE-Cy7-conjugated anti-human CD3 (OKT3) was from BioLegend. PE-conjugated H-2K$^b$-SIINFEKL tetramer was from Beckman Coulter.

Flow cytometry and cell sorting. Cells were surface stained with antibodies for 30 min at 4° C. in PBS containing 3% FBS, 100 µg/ml of anti-CD16/32, 5% normal rat serum, 5% normal mouse serum and 10 mM EDTA. Intracellular staining was done after surface staining with BD Cytofix/Cytoperm™ kit (BD Biosciences) according to the manufacturer's instruction. Tetramer staining was done for 30 min at room temperature. Dead cells were positively stained with LIVE/DEAD Fixable Aqua Dead Cell Stains (Molecular Probes) or 7AAD (eBioscience) and excluded from analysis. Stained cells were washed and analyzed on a LSRII flow cytometer (BD Biosciences) and FlowJo software (Tree Star). For splenic DC sorting, spleens were minced and digested in HBSS containing 5% FBS, 10 mM HEPES with collagenase A (1 mg/ml; Roche) and DNase I (0.4 mg/ml; Roche) for 30 min at 37° C. Post-digested splenocyte suspensions were passed through a cell strainer (70 um Nylon; Falcon) and resuspended in HBSS containing 5% FBS, 10 mM HEPES and 10 mM EDTA. Red blood cells (RBCs) were lysed with ammonium-chloride-potassium bicarbonate (ACK) lysing buffer. To obtain DC-enriched splenocytes, cells were incubated with biotinylated Ly-6G/Gr-1 (RB6-8C5; eBioscience), CD19, B200 and CD3 (all at 1.25 µg/ml) for 30 min at 4° C., followed by a 15-minute incubation with streptavidin-conjugated MACS magnetic MicroBeads (Miltenyi) at 4° C. The cells were negative selected via MACS LD columns (Miltenyi). The effluent cells were further surface stained with anti-CD11c, CD45, CD8, I-A/I-E and 7AAD. High purity (>95%) splenic DCs were sorted for CD11c$^+$I-A/I-E$^+$ CD45$^+$7AAD$^-$ cells on a FACS Aria II cell sorter (BD Biosciences). The resulting splenic DCs were composed of both CD8$^+$CD11b$^-$DCs (~25%) and CD8$^-$CD11b$^+$DCs (~75%). For naïve T cell sorting, spleens from OT-I or OT-II mice were minced and the cell suspensions were RBC-lysed and passed through a cell strainer (70 um Nylon; Falcon). The resulting single-cell suspensions were surface stained with anti-Vα2, CD62L, CD44, CD8 (for OT-I), CD4 (for OT-II), CD25 and 7AAD (eBioscience). High purity (>95%) naïve OT-I or OT-II cells were sorted for Vα2$^+$CD62L$^{hi}$CD44$^{lo}$CD25$^-$7AAD$^-$CD4$^+$ (OT-II) or CD8$^+$(OT-I) cells on a MoFlo XDP sorter (Beckman Coulter).

Mouse monocyte purification and monocyte transfer (vaccination). Classic (Ly-6C$^+$) monocytes were purified from bone marrow cells as previously described (26). Bone marrow cells were harvested in cRPMI-10 medium (glutamine-free RPMI-1640 medium with 10% FBS, 100 U/ml penicillin, 100 µg/ml streptomycin, 100 µM MEM-non-essential amino acids, 2 mM L-glutamine and 1 mM sodium pyruvate). Red blood cells were lysed with ammonium chloride-potassium bicarbonate buffer. The resulting cell suspensions were passed through a 70 um Nylon cell strainer (Falcon). The filtered cells were incubated for 30 min at 4° C. with biotinylated anti-CD3ε, CD4, CD8α, CD11c, CD19, B220, CD49b, I-A$^b$, Sca-1, c-Kit, TER-119, and FITC-conjugated anti-Ly-6G and anti-CCR3 (5 ul/ml for anti-CCR3; all the others at a concentration of 1.25 ug/ml), followed by a 15 min incubation with streptavidin-conjugated and anti-FTIC MicroBeads (Miltenyi). Highly enriched classic monocytes (>90% purity) were negatively selected with MACS LD columns (Miltenyi) per the manufacturer's instruction. The morphology of the purified monocytes was examined with the cytopin and the cells were stained with PROTOCOL Hema 3 Fixative and Solutions (comparable to Wright-Giemsa stain; Fisher HealthCare) according to the manufacturer's instruction. For monocyte administration, antigen-loaded monocytes were intravenously injected into the recipient mice via retro-orbital route in a volume of 60 ul with the desired cell number.

Antigen loading of mouse monocytes. To load full-length proteins on monocytes, ovalbumin protein (OVA) (Sigma A5503), DQ™ ovalbumin (DQ-OVA) (Molecular Probes) or Alexa Fluor 647 conjugated ovalbumin (OVA-AF647) (Molecular Probes) (all at a concentration of 1 mg/ml except otherwise indicated) was incubated with purified monocytes ($10^6$/ml) in cRPMI-20 medium (glutamine-free RPMI-1640 medium with 20% FBS, 100 U/ml penicillin, 100 µg/ml streptomycin, 100 µM MEM-non-essential amino acids, 2 mM L-glutamine and 1 mM sodium pyruvate) for 1.5 hours with 5% $CO_2$ at 37° C. For peptide loading, mutant IDH1-R132H 25-mer (GWVKPIIGHHAYGDQYRATDFVVP; SEQ ID NO: 5; JPT, Germany; 250 µg/ml), TRP2$_{180-188}$ (SVYDFFVWL, SEQ ID NO: 6; 250 µg/ml), FITC-labeled OVA$_{323-339}$ (ISQAVHAAHAEINEAGR, SEQ ID NO: 7; 1-200 µg/ml) or OVA$_{323-339}$-NH$_2$ peptide (ISQAVHAA-HAEINEAGR, SEQ ID NO: 7; 200 µg/ml) (all from AnaSpec) was incubated at the concentrations as indicated with monocytes ($10^6$/ml) in cRPMI-20 medium for 2 hours with 5% $CO_2$ at 37° C. To transfect RNAs into monocytes, mRNA encoding full-length ovalbumin (OVA-mRNA) was used at a dose of 5 µg/$10^6$ cells. OVA-mRNA was thoroughly mixed with Lipofectamine MessengerMax (Invitrogen) at a ratio of 1:4 (wt/vol) after both were 10-fold diluted in Opti-MEM medium (Gibco). The lipid-mRNA mixture was left at room temperature for 5 minutes and was then added into monocyte suspensions ($10^6$/ml) in cRPMI-20 medium for 2 hr-incubation with 5% $CO_2$ at 37° C. In case of pertussis toxin (PTX; Sigma) treatment, PTX was added into the incubation medium at a concentration of 100 ng/ml. Post-incubated monocytes were washed thoroughly with PBS before use.

Restimulation of total splenocytes with PMA and ionomycin. Total splenocytes were isolated from mice vaccinated 7 days earlier with OVA-loaded monocytes i.v. ($4\times10^6$ per mouse), OVA/CFA s.c. (1:1 emulsion; 200 µg OVA/200 µg per mouse; Sigma) or PBS/CFA (1:1 emulsion; 200 µl per mouse; Sigma) s.c. and were cultured at $5\times10^6$/ml for 4 hours in cRPMI-10 medium containing 50 µM 2-mercapto-ethanol (2-ME), PMA (50 ng/ml; Abcam), ionomycin (500 ng/ml; Sigma), brefeldin A (BD Biosciences) and monensin (eBioscience) with 5% $CO_2$ at 37° C. Cells were then washed and stained with H-2K$^b$-SIINFEKL tetramer, followed by Aqua Dead cell staining, surface staining and intracellular staining with anti-Eomes, T-bet, Granzyme B and IFNγ. Live tetramer$^+$CD8 T cells were gated for further analysis of effector functions. In vivo CTL assay. In vivo CTL assay was performed as previously described (59) with some modifications. In brief, target cells were prepared from RBC-depleted naïve syngeneic splenocytes with or without SIINFEKL peptide pulsing (1 µg/ml for 45 min at 37° C.). SIINFEKL-pulsed and -unpulsed splenocytes were labeled with CFSE at high (5 µM; CFSE$^{high}$) and low concentrations (0.5 µM; CFSE$^{low}$) respectively. CFSE$^{high}$ and CFSE$^{low}$ cells were mixed well at a 1:1 ratio and were thoroughly washed with PBS before use. Total $10\times10^6$ cells ($5\times10^6$ from each population) in 50 ul PBS were intravenously injected in each recipient mouse immunized 7 days earlier with OVA-loaded monocytes ($4\times10^6$ cells i.v.), OVA/CFA (200 µg OVA/200 µl s.c.) or PBS/CFA (200 µl s.c.). Spleens were harvested 6 hrs later from recipient mice and single-cell suspensions were prepared for flow cytometry. Peptide-pulsed and—unpulsed target cells were identified by their differential CFSE intensity. Up to $10^4$ CFSE-positive cells were collected for analysis. Specific lysis was quantified with the following formula: % specific lysis=$[1-(R_{naive}/R_{immunized})]\times100$, where R=% CFSE$^{low}$ cells/% CFSE$^{high}$ cells.

CFSE-labeling and T cell proliferation assay. Sorted naïve OT-I or OT-II cells were incubated with CFSE (5 µM; Molecular Probes) for 10 min at 37° C. and thoroughly washed. CFSE-labeled cells were injected into recipient mice ($5\times10^5$ per mouse) or co-cultured ($10^5$ per sample) with other cells in vitro and were harvested 64 hours after in vivo vaccination or in vitro co-culture. Cell proliferation based on CFSE dilution was analyzed on FlowJo software (Tree Star). Responder frequency (R) and proliferative capacity (the number of daughter cells that the average responder cell can generate) (Cp) were calculated as previously described (60).

Co-culture of mouse monocytes, T cells and DCs. Monocytes, splenic DCs and CFSE-labeled naïve OT-I or OT-II cells were co-cultured with $10^5$ cells for each cell type in 700 µl of cRMPI-10 medium with 50 µM 2-ME per well in a 24-well plate. To block gap junctions, GAP27 (500 µM; batch 7A, TOCRIS), scrambled GAP27 (500 µM; negative control; AnaSpec) or carbenoxolone (150 µM; TOCRIS) was added as required. For transwell experiments, $10^5$ OVA-loaded monocytes in 100 µl culture medium were placed in a transwell (0.4 µm pore size; Corning) on top of the bottom well where splenic DCs ($10^5$) and CFSE-labeled OT-I or OT-II cells ($10^5$) were cultured in 600 µl culture medium. The cells were harvested 64 hours later for T cell proliferation analysis by flow cytometry. To examine APC function of splenic DCs, FACS-sorted splenic DCs ($10^5$ cells) were pulsed with SIINFEKL peptides (10 µM) and co-cultured with CFSE-labeled naïve OT-I cells ($10^5$ cells) in 200 µl medium for 64 hours.

Co-culture of autologous human monocytes, lymphocytes and DCs. Human blood cells were obtained from volunteers after informed consent under clinical protocol PRO-00009403, approved by the Duke Institutional Review Board. Highly-enriched human monocytes (>80%) and lymphocytes (>95%) were obtained from two CMV-positive donors by elutriation with a cell separator (Elutra™; Terumo BCT, Lakewood, CO) (55). After collection, the cells were frozen and assessed for contamination and lineage purity as previously described(61). Autologous DCs were generated from monocytes in AIM V medium (Gibco) containing GM-CSF (800 U/ml) and IL-4 (500 U/ml) using the method described previously(62). The 1.932-kb CMV pp65 full-length cDNA insert was obtained from B. Britt and RNA was generated as previously reported(62). To transfect RNAs into monocytes, mRNA was used at a dose of 5 µg per 10⁶ cells. CMV pp65-mRNA was thoroughly mixed with Lipofectamine MessengerMax (Invitrogen) at a ratio of 1:4 (wt/vol) after both were 10-fold diluted in Opti-MEM medium (Gibco). The lipid-mRNA mixture was left at room temperature for 5 minutes and was then added into monocyte suspensions ($10^6$/ml) in AIM V medium with 10% FBS (the culture medium) for 2 hour-incubation with 5% $CO_2$ at 37° C. Post-incubated monocytes were washed thoroughly with PBS and resuspended in the culture medium. Autologous CMV pp65 RNA-transfected human monocytes, CFSE-labeled lymphocytes ($10^5$) and/or DCs (all at a number of $10^5$ cells per well) were co-cultured in a 96-well plate with 5% $CO_2$ at 37° C. for 64 hours before flow cytometric analysis of T cell proliferation.

Cell isolation from multiple organs for phenotyping. Mice were systemically perfused with PBS via the left and right ventricles. Lungs, livers and spleens were dissolved with HBSS medium containing 5% FBS, 10 mM HEPES, collagenase A (1 mg/ml; Roche) and DNase I (0.4-0.6 mg/ml; Roche) for 30 minutes at 37° C. by gentle shaking. The resulting cell suspensions were minced and passed through a 70 um cell strainer (Falcon) and RBCs were lysed by ACK lysing buffer. A lymph node (LN) sample was pooled from bilateral inguinal and popliteal LNs (n=4). Single-cell suspensions from LNs were prepared in the same way as described above for the solid organs except no RBC lysis was required. Single-cell suspensions of BM samples were prepared from femoral bones with a RBC lysis process and cell strainer filtering. Blood was collected by submandibular bleeding methods. Mononuclear blood cell-enriched samples were prepared by density gradient centrifugation methods with Lymphocyte Separation Medium (LSM, density=1.077-1.08 g/ml at 20° C.; Cellgro).

Time-lapse live imaging of monocyte-DC co-culture. DQ-OVA-loaded/labeled mouse monocytes and FACS-sorted mouse splenic DCs were co-cultured in a 1:1 ratio by cell number in cRPMI-20 medium for 18 hours in a temperature, humidity and $CO_2$-controlled incubation chamber. A fixed field of the culture dish was continuously imaged with a Zeiss Axio Observer Z1. The images were processed and analyzed on MetaMorph and FIJI.

Immunofluorescence. Freshly harvested spleens were immediately frozen in OCT-filled cassettes. Frozen sections of 10 μm-thickness were prepared and stained with the following primary antibodies: rat anti-mouse B220 (RA3-6B2; BioLegend), Armenian hamster anti-mouse CD11c (N418; eBioscience), biotinylated mouse anti-mouse CD45.2 (104; eBioscience), rabbit anti-mouse connexin 43 (polyconal, affinity purified; Sigma) and normal rabbit IgG (Santa Cruz). The secondary antibodies were Alexa Fluor 488-conjugated donkey anti-rat IgG, Alexa Fluor 488-conjugated donkey anti-rabbit IgG, Alexa Fluor 568-conjugated goat anti-hamster IgG and Alexa Fluor 647-conjugated streptavidin (all from Molecular Probes). Control staining of connexin 43 was performed with normal rabbit IgG as primary antibody plus secondary antibody or with secondary antibody alone. For obtaining statistics of OVA-loaded monocyte-splenic DC interaction, three fields as shown in FIG. 6c were randomly picked up from the two ends and the central portion of a splenic section (total 9 fields per splenic section) per mouse. There were 3 mice per group and therefore, total 27 fields from the mice of a single group were examined. The percentage of DC-interacting injected monocytes among total injected monocytes in the chosen field was recorded. The data from total 27 fields were pooled per group for comparison with the other group. Confocal images were taken with a Leica SP5 inverted confocal microscope and analyzed on Imaris and Fiji/ImageJ.

Quantitative real-time PCR. RNA was extracted from FACS-sorted splenic DCs by using TRIzol Reagent (Ambion) and the contaminated DNA was removed with a DNA removal kit (DNA-free™; Invitrogen). RNA was reverse transcribed into cDNA with iScript cDNA synthesis kit (Bio-Rad). Quantitative PCR was performed with iQ SYBR Green Supermix reagent (Bio-Rad) on a StepOnePlus Real-Time PCR System (Applied Biosystems). The expression of connexin 43 gene (Gja1) was normalized to ribosomal protein L32 (Rpl32) housekeeping gene(22) and the PCR samples were duplicated. Results were quantified by the $2^{-\Delta\Delta CT}$ method(63). The primer sequences are as followed: Gja1-forward 5'-ACTTCAGCCTCCAAGGAGTTC (SEQ ID NO: 1) and Gja1-reverse 5'-GGAGTAGGCTTGGACCTTGTC-3' (SEQ ID NO: 2); Rpl32-forward 5'-AAGCGAAACTGGCGGAAAC-3' (SEQ ID NO: 3) and Rpl32-reverse 5'-TAACCGATGTTGGG-CATCAG-3' (SEQ ID NO: 4).

ELISA to measure anti-OVA titers in serum. ELISA assays were performed in Corning Costar high binding immunoassay plates. All wash steps were with 300 μl of 0.1% (v/v) Tween 20 in phosphate buffered saline (PBST) in a BioTek 405TS plate washer. Assay wells were coated with 100 μl of 00 ug/ml ovalbumin (Sigma A5503) in PBS by incubating the plate 16 hours at 4° C. After washing, the wells were blocked with 200 μl of blocking solution (2% w/v bovine serum albumin, 5% v/v goat serum in PBS) for 2 hours at room temperature. After washing, 100 μl volumes of serial dilutions of serum from immunized or control mice were added. After 1.5 hours at room temperature, the plates wash were washed and 100 μl of peroxidase-conjugated goat anti-mouse Fc antibody (IgG- or IgM-specific; Pierce) diluted 1:5000 in PBST was added. After 1 hour at room temperature, the wells were washed and 100 μl of TMB (3,3',5,5'-tetramethylbenzidine; Pierce) substrate was added. After 15 minutes at room temperature, the reaction was stopped by adding 100 μl of 2M sulfuric acid. Absorbance values at 450 nm were used to calculate half maximal titers.

Tetanus-diphtheria (Td) toxoid Immunizations and DC vaccination. A Td toxoid-involved DC vaccination protocol for optimal anti-tumor efficacy was followed as previously reported(43). Female 6-8 week-old C57BL/6 mice received a primary intramuscular (i.m.) vaccine of Td toxoid (Sanofi Aventis; Tenivac®; 1 Lf, 100 μl) administered bilaterally into the quadriceps muscle (50 μl per leg). An intramuscular booster (0.5 Lf, 50 μl) was administered two weeks later. Vaccine site pre-conditioning with Td toxoid (0.5 Lf) was given intradermally (i.d.) two weeks after the booster and randomized to the right or left groin site. DCs were resuspended at $1\times10^6$/100 μL PBS (Gibco) and administered i.d. on both sides 0.8 cm from the groin crease 24 hours after i.d. pre-conditioning. DCs injected in the groin ipsilateral to the Td pre-conditioning side were directly injected i.d. within the erythematous nodule produced by Td pre-conditioning. DCs were generated from the bone marrow of 6-8 week old female C57BL/6 wild-type mice and electroporated with 10 μg OVA-mRNA per $5\times10^6$ DCs as previously described(43, 64).

Mouse tumor models. In subcutaneous melanoma models, B16/F10-OVA and B16/F10 cells were grown as previously published(58) and injected subcutaneously (s.c.) at a dose of $2\times10^5$ (B16/F10-OVA) or $5\times10^4$ (B16/F10) cells in 200 μL of PBS in the flank of C57BL/6 mice at time points either after (memory model) or before (therapeutic model) vaccination/immunization as indicated in each experiment.

Depending on the experiments, the mice were injected with OVA/CFA (1:1 emulsion; 200 µg OVA/200 µl per mouse) on the back s.c., OVA RNA-electroporated DCs ($10^6$ per mouse weekly ×3 doses) i.d., $TRP2_{180-188}$ peptide-loaded monocytes ($10^6$ per mouse ×6 doses at indicated time points) or OVA protein-loaded monocytes ($3 \times 10^6$ per mouse single-dose or $10^6$ per mouse weekly ×3 doses) i.v. Mice vaccinated with OVA-DCs also received Td toxoid immunizations plus or minus autologous lymphocyte transfer (ALT) of $10 \times 10^6$ OT-I splenocytes and $10^6$ C57BL/6 splenocytes given intravenously as previously described(43) right before DC vaccination on day 8 post tumor implantation. For combination therapy with checkpoint blockade treatment, anti-CTLA4 (100 µg per mouse), anti-PD-1 (250 µg per mouse), anti-PD-L1 (150 m per mouse) or the equivalent dose of control antibody was given i.p. on days 8, 11 and 14 post tumor inoculation. Randomization of mice occurred after tumor inoculation prior to vaccine site Td pre-conditioning and the first OVA-DC or OVA-monocyte vaccination. Beginning ten days after tumor inoculation, flank sites were monitored daily for tumor growth, and tumor size was measured every two days by an unblinded observer. Tumor volume ($mm^3$) was calculated by the formula ($\pi/6 \times length \times width^2$) in a perpendicular fashion. Mice were sacrificed when ulceration occurred (predefined exclusion criteria) or when the tumor reached either 2 cm in any direction or an estimated volume of 2,000 $mm^3$. Analysis of tumor growth focused on follow-up assessments and tumor sizes were compared between different groups at the time points when significant dropout occurred in any group. In the therapeutic intracranial (i.c.) tumor model, CT-2A-mIDH1-R132H cells were i.c. injected at a dose of $5 \times 10^4$ per mouse 3 days prior to the treatment began. The mice were treated with anti-PD-1 (250 µg per mouse) i.p. on D3, D6 and D9 either alone or with IV mIDH1(R132H) 25-mer peptide-loaded monocytes ($3 \times 10^6$ per mouse) on D3 post tumor injection. Mice were sacrificed by a blinded observer when the protocol-defined humane points occurred.

Statistical analysis. For both in vitro and animal studies, group sizes were determined based on numbers required to obtain significant differences in previous studies of similar models. All the numerical data were analyzed for significance ($P<0.05$) by ANOVA or by unpaired two-tailed Student's t-test. Variance was similar between groups in all studies. Kaplan-Meier survival curves were analyzed for significance ($P<0.05$) by Log-rank (Mantel-Cox) test. The statistics were performed with Prism (GraphPad Software, Inc.).

REFERENCES

1. Tivnan A, Heilinger T, Lavelle E C, and Prehn J H. Advances in immunotherapy for the treatment of glioblastoma. *J Neurooncol.* 2016.
2. Kumai T, Kobayashi H, Harabuchi Y, and Celis E. Peptide vaccines in cancer-old concept revisited. *Curr Opin Immunol.* 2016; 45:1-7.
3. Cawood R, Hills T, Wong S L, Alamoudi A A, Beadle S, Fisher K D, et al. Recombinant viral vaccines for cancer. *Trends Mol Med.* 2012; 18(9):564-74.
4. Chiang C L, Coukos G, and Kandalaft L E. Whole Tumor Antigen Vaccines: Where Are We? *Vaccines (Basel).* 2015; 3(2):344-72.
5. Signori E, Iurescia S, Massi E, Fioretti D, Chiarella P, De Robertis M, et al. DNA vaccination strategies for anti-tumour effective gene therapy protocols. *Cancer Immunol Immunother.* 2010; 59(10):1583-91.
6. Palucka K, and Banchereau J. Cancer immunotherapy via dendritic cells. *Nat Rev Cancer.* 2012; 12(4):265-77.
7. Klebanoff C A, Acquavella N, Yu Z, and Restifo N P. Therapeutic cancer vaccines: are we there yet? *Immunol Rev.* 2011; 239(1):27-44.
8. Heath W R, and Carbone F R. Cross-presentation in viral immunity and self-tolerance. *Nature reviews Immunology.* 2001; 1(2):126-34.
9. Kurts C, Robinson B W, and Knolle P A. Cross-priming in health and disease. *Nature reviews Immunology.* 2010; 10(6):403-14.
10. den Haan J M, Lehar S M, and Bevan M J. CD8(+) but not CD8(−) dendritic cells cross-prime cytotoxic T cells in vivo. *J Exp Med.* 2000; 192(12):1685-96.
11. Belz G T, Smith C M, Eichner D, Shortman K, Karupiah G, Carbone F R, et al. Cutting edge: conventional CD8 alpha+ dendritic cells are generally involved in priming CTL immunity to viruses. *J Immunol.* 2004; 172(4):1996-2000.
12. Wimmers F, Schreibelt G, Skold A E, Figdor C G, and De Vries I J. Paradigm Shift in Dendritic Cell-Based Immunotherapy: From in vitro Generated Monocyte-Derived DCs to Naturally Circulating DC Subsets. *Front Immunol.* 2014; 5:165.
13. Helft J, Bottcher J, Chakravarty P, Zelenay S, Huotari J, Schraml B U, et al. GM-CSF Mouse Bone Marrow Cultures Comprise a Heterogeneous Population of CD11c(+)MHCII(+) Macrophages and Dendritic Cells. *Immunity.* 2015; 42(6):1197-211.
14. Randolph G J, Jakubzick C, and Qu C. Antigen presentation by monocytes and monocyte-derived cells. *Curr Opin Immunol.* 2008; 20(1):52-60.
15. Jakubzick C, Gautier E L, Gibbings S L, Sojka D K, Schlitzer A, Johnson T E, et al. Minimal differentiation of classical monocytes as they survey steady-state tissues and transport antigen to lymph nodes. *Immunity.* 2013; 39(3):599-610.
16. Gehring A J, Haniffa M, Kennedy P T, Ho Z Z, Boni C, Shin A, et al. Mobilizing monocytes to cross-present circulating viral antigen in chronic infection. *J Clin Invest.* 2013; 123(9):3766-76.
17. Le Borgne M, Etchart N, Goubier A, Lira S A, Sirard J C, van Rooijen N, et al. Dendritic cells rapidly recruited into epithelial tissues via CCR6/CCL20 are responsible for CD8+ T cell crosspriming in vivo. *Immunity.* 2006; 24(2):191-201.
18. Zhang Y, Zhang R, Zhang H, Liu J, Yang Z, Xu P, et al. Microparticles released by Listeria monocytogenes-infected macrophages are required for dendritic cell-elicited protective immunity. *Cell Mol Immunol.* 2012; 9(6):489-96.
19. Balboa L, Kviatcovsky D, Schierloh P, Garcia M, de la Barrera S, and Sasiain MD. Monocyte-derived dendritic cells early exposed to Mycobacterium tuberculosis induce an enhanced T helper 17 response and transfer mycobacterial antigens. *Int J Med Microbial.* 2016; 306(7):541-53.
20. Samstein M, Schreiber H A, Leiner I M, Susac B, Glickman M S, and Pamer E G. Essential yet limited role for CCR2(+) inflammatory monocytes during Mycobacterium tuberculosis-specific T cell priming. *Elife.* 2013; 2:e01086.
21. Srivastava S, and Ernst J D. Cell-to-cell transfer of M. tuberculosis antigens optimizes CD4 T cell priming. *Cell Host Microbe.* 2014; 15(6):741-52.
22. Mazzini E, Massimiliano L, Penna G, and Rescigno M. Oral tolerance can be established via gap junction transfer of fed antigens from CX3CR1(+) macrophages to CD103 (+) dendritic cells. *Immunity.* 2014; 40(2):248-61.
23. Xu Y, Liu Y, Yang C, Kang L, Wang M, Hu J, et al. Macrophages transfer antigens to dendritic cells by releasing exosomes containing dead-cell-associated antigens partially through a ceramide-dependent pathway to enhance CD4(+) T-cell responses. *Immunology.* 2016; 149(2):157-71.
24. Qu C, Nguyen V A, Merad M, and Randolph G J. MHC class I/peptide transfer between dendritic cells overcomes poor cross-presentation by monocyte-derived APCs that engulf dying cells. *J Immunol.* 2009; 182(6):3650-9.
25. Backer R, Schwandt T, Greuter M, Oosting M, Jungerkes F, Tuting T, et al. Effective collaboration between marginal metallophilic macrophages and CD8+ dendritic cells in the generation of cytotoxic T cells. *Proc Natl Acad Sci USA.* 2010; 107(1):216-21.
26. Nakano H, Lin K L, Yanagita M, Charbonneau C, Cook D N, Kakiuchi T, et al. Blood-derived inflammatory dendritic cells in lymph nodes stimulate acute T helper type 1 immune responses. *Nat Immunol.* 2009; 10(4):394-402.
27. Soudja S M, Ruiz A L, Marie J C, and Lauvau G Inflammatory monocytes activate memory CD8(+) T and innate NK lymphocytes independent of cognate antigen during microbial pathogen invasion. *Immunity.* 2012; 37(3):549-62.
28. Schreiber H A, Loschko J, Karssemeijer R A, Escolano A, Meredith M M, Mucida D, et al. Intestinal monocytes and macrophages are required for T cell polarization in response to Citrobacter rodentium. *J Exp Med.* 2013; 210(10):2025-39.
29. Allan R S, Waithman J, Bedoui S, Jones C M, Villadangos J A, Zhan Y, et al. Migratory dendritic cells transfer antigen to a lymph node-resident dendritic cell population for efficient CTL priming. *Immunity.* 2006; 25(1):153-62.
30. Cyster J G, and Goodnow C C. Pertussis toxin inhibits migration of B and T lymphocytes into splenic white pulp cords. *J Exp Med.* 1995; 182(2):581-6.
31. Geissmann F, Jung S, and Littman D R. Blood monocytes consist of two principal subsets with distinct migratory properties. *Immunity.* 2003; 19(1):71-82.
32. Kajimoto T, Okada T, Miya S, Zhang L, and Nakamura S. Ongoing activation of sphingosine 1-phosphate receptors mediates maturation of exosomal multivesicular endosomes. *Nature communications.* 2013; 4:2712.
33. Lampe P D, Qiu Q, Meyer R A, TenBroek E M, Walseth T F, Starich T A, et al. Gap junction assembly: PTX-sensitive G proteins regulate the distribution of connexin43 within cells. *American journal of physiology Cell physiology.* 2001; 281(4):C1211-22.
34. Neijssen J, Herberts C, Drijfhout J W, Reits E, Janssen L, and Neefjes J. Cross-presentation by intercellular peptide transfer through gap junctions. *Nature.* 2005; 434 (7029):83-8.
35. Oviedo-Orta E, and Howard Evans W. Gap junctions and connexin-mediated communication in the immune system. *Biochimica et biophysica acta.* 2004; 1662(1-2):102-12.
36. Thery C, Ostrowski M, and Segura E. Membrane vesicles as conveyors of immune responses. *Nature reviews Immunology.* 2009; 9(8):581-93.
37. Aharon A, Tamari T, and Brenner B. Monocyte-derived microparticles and exosomes induce procoagulant and apoptotic effects on endothelial cells. *Thromb Haemost.* 2008; 100(5):878-85.
38. Ekstrom K, Omar O, Graneli C, Wang X, Vazirisani F, and Thomsen P. Monocyte exosomes stimulate the osteogenic gene expression of mesenchymal stem cells. *PLoS One.* 2013; 8(9):e75227.
39. Saccheri F, Pozzi C, Avogadri F, Barozzi S, Faretta M, Fusi P, et al. Bacteria-induced gap junctions in tumors favor antigen cross-presentation and antitumor immunity. *Science translational medicine.* 2010; 2(44):44ra57.
40. Chaytor A T, Bakker L M, Edwards D H, and Griffith T M. Connexin-mimetic peptides dissociate electrotonic EDHF-type signalling via myoendothelial and smooth muscle gap junctions in the rabbit iliac artery. *British journal of pharmacology.* 2005; 144(1):108-14.
41. Rozental R, Srinivas M, and Spray D C. How to close a gap junction channel. Efficacies and potencies of uncoupling agents. *Methods Mol Biol.* 2001; 154:447-76.
42. Davies L C, Jenkins S J, Allen J E, and Taylor P R. Tissue-resident macrophages. *Nat Immunol.* 2013; 14(10):986-95.
43. Mitchell D A, Batich K A, Gunn M D, Huang M N, Sanchez-Perez L, Nair SK, et al. Tetanus toxoid and CCL3 improve dendritic cell vaccines in mice and glioblastoma patients. *Nature.* 2015; 519(7543):366-9.
44. Sharma P, and Allison J P. Immune Checkpoint Targeting in Cancer Therapy: Toward Combination Strategies with Curative Potential. *Cell.* 2015; 161(2):205-14.
45. van Elsas A, Sutmuller R P, Hurwitz A A, Ziskin J, Villasenor J, Medema J P, et al. Elucidating the autoimmune and antitumor effector mechanisms of a treatment based on cytotoxic T lymphocyte antigen-4 blockade in combination with a B16 melanoma vaccine: comparison of prophylaxis and therapy. *J Exp Med.* 2001; 194(4): 481-9.
46. Hodges T R, Choi B D, Bigner D D, Yan H, and Sampson J H. Isocitrate dehydrogenase 1: what it means to the neurosurgeon: a review. *J Neurosurg.* 2013; 118(6):1176-80.
47. Schumacher T, Bunse L, Pusch S, Sahm F, Wiestler B, Quandt J, et al. A vaccine targeting mutant IDH1 induces antitumour immunity. *Nature.* 2014; 512(7514):324-7.
48. Oh T, Fakurnejad S, Sayegh E T, Clark A J, Ivan M E, Sun M Z, et al. Immunocompetent murine models for the study of glioblastoma immunotherapy. *J Transl Med.* 2014; 12:107.
49. Russo V, Cipponi A, Raccosta L, Rainelli C, Fontana R, Maggioni D, et al. Lymphocytes genetically modified to express tumor antigens target DCs in vivo and induce anti-tumor immunity. *J Clin Invest.* 2007; 117(10):3087-96.
50. Phua K K, Boczkowski D, Dannull J, Pruitt S, Leong K W, and Nair S K. Whole Blood Cells Loaded with Messenger RNA as an Anti-Tumor Vaccine. *Adv Healthc Mater.* 2013.
51. Jung S, Unutmaz D, Wong P, Sano G, De los Santos K, Sparwasser T, et al. In vivo depletion of CD11c+ dendritic cells abrogates priming of CD8+ T cells by exogenous cell-associated antigens. *Immunity.* 2002; 17(2):211-20.
52. Mendoza-Naranjo A, Saez P J, Johansson C C, Ramirez M, Mandakovic D, Pereda C, et al. Functional gap junctions facilitate melanoma antigen transfer and cross-presentation between human dendritic cells. *J Immunol.* 2007; 178(11):6949-57.

53. Fehres C M, Unger W W, Garcia-Vallejo J J, and van Kooyk Y. Understanding the biology of antigen cross-presentation for the design of vaccines against cancer. *Front Immunol.* 2014; 5:149.

54. Andersen B M, and Ohlfest J R. Increasing the efficacy of tumor cell vaccines by enhancing cross priming. *Cancer Lett.* 2012; 325(2):155-64.

55. Berger T G, Strasser E, Smith R, Carste C, Schuler-Thurner B, Kaempgen E, et al. Efficient elutriation of monocytes within a closed system (Elutra) for clinical-scale generation of dendritic cells. *J Immunol Methods.* 2005; 298(1-2):61-72.

56. Kim S, Kim H O, Baek E J, Choi Y, Kim H S, and Lee M G. Monocyte enrichment from leukapheresis products by using the Elutra cell separator. *Transfusion.* 2007; 47(12):2290-6.

57. Daniels G A, Sanchez-Perez L, Diaz R M, Kottke T, Thompson J, Lai M, et al. A simple method to cure established tumors by inflammatory killing of normal cells. *Nat Biotechnol.* 2004; 22(9):1125-32.

58. Sanchez-Perez L, Kottke T, Diaz R M, Ahmed A, Thompson J, Chong H, et al. Potent selection of antigen loss variants of B16 melanoma following inflammatory killing of melanocytes in vivo. *Cancer research.* 2005; 65(5):2009-17.

59. Lin K L, Sweeney S, Kang B D, Ramsburg E, and Gunn M D. CCR2-antagonist prophylaxis reduces pulmonary immune pathology and markedly improves survival during influenza infection. *J Immunol.* 2011; 186(1):508-15.

60. Gudmundsdottir H, Wells A D, and Turka L A. Dynamics and requirements of T cell clonal expansion in vivo at the single-cell level: effector function is linked to proliferative capacity. *J Immunol.* 1999; 162(9):5212-23.

61. Thurner B, Roder C, Dieckmann D, Heuer M, Kruse M, Glaser A, et al. Generation of large numbers of fully mature and stable dendritic cells from leukapheresis products for clinical application. *J Immunol Methods.* 1999; 223(1):1-15.

62. Nair S, Archer G E, and Tedder T F. Isolation and generation of human dendritic cells. *Current protocols in immunology/edited by John E Coligan [et al].* 2012; Chapter 7:Unit7 32.

63. Schmittgen T D, and Livak K J. Analyzing real-time PCR data by the comparative C(T) method. *Nature protocols.* 2008; 3(6):1101-8.

64. Inaba K, Swiggard W J, Steinman R M, Romani N, and Schuler G. Isolation of dendritic cells. *Current protocols in immunology/edited by John E Coligan [et al].* 2001; Chapter 3:Unit 3 7.

Example 2

Vaccination with Antigen-Loaded Neutrophils

Materials and Methods
Mouse Neutrophil Purification and Transfer (Vaccination).

Bone marrow cells were harvested in cRPMI-10 medium (glutamine-free RPMI-1640 medium with 10% FBS, 100 U/ml penicillin, 100 ug/ml streptomycin, 100 uM MEM-non-essential amino acids, 2 mM L-glutamine and 1 mM sodium pyruvate). Red blood cells were lysed with ammonium chloride-potassium bicarbonate buffer. The resulting cell suspensions were passed through a 70 um Nylon cell strainer (Falcon). The filtered cells were incubated for 30 min at 4° C. with biotinylated anti-Ly-6G (BioLegend), followed by a 15 min incubation with streptavidin-conjugated MicroBeads (Miltenyi). Ly6G$^+$ neutrophils (>84% purity) were positively selected with MACS LS columns (Miltenyi) per the manufacturer's instructions. For neutrophil vaccination, antigen-loaded neutrophils were intravenously injected into the recipient mice via retro-orbital route in a volume of 60u1 with the desired cell number.

Antigen Loading on Mouse Neutrophils.

To load full-length proteins on neutrophils, ovalbumin protein (OVA) (Sigma A5503) (1 mg/ml) was incubated with purified neutrophils ($10^6$/ml) in cRPMI-20 medium (glutamine-free RPMI-1640 medium with 20% FBS, 100 U/ml penicillin, 100 ug/ml streptomycin, 100 uM MEM-non-essential amino acids, 2 mM L-glutamine and 1 mM sodium pyruvate) for 1.5 hours with 5% $CO_2$ at 37° C.

Results

Figure 16D:
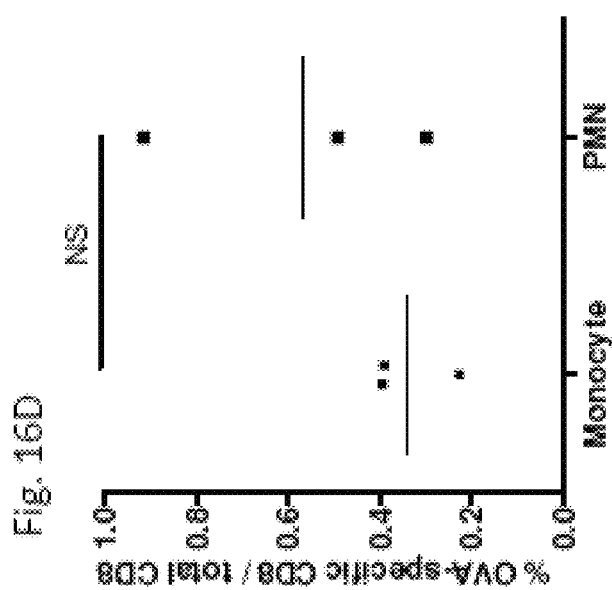
FIG. 16D is a graph showing that both monocyte and neutrophils loaded with antigen can induce antigen-specific CD8+ T cell proliferation.
Figure 16C:
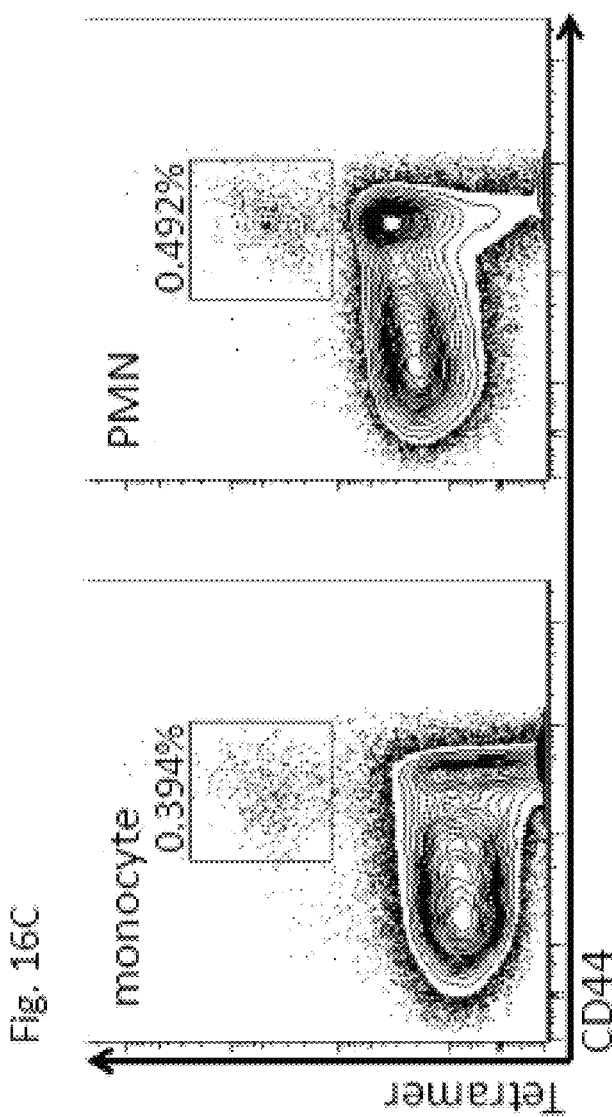
FIG. 16C is a set of FACS plots showing that both monocytes and neutrophils loaded with antigen can induce proliferation of tetramer$^+$ CD8$^+$ T cells.

To determine if the ability of antigen-loaded monocytes to stimulate CD4 and CD8 T cells responses was limited to only monocytes, we tested the ability of purified polymorphonuclear cells (PMNs or neutrophils) in antigen loading experiments similar to those described above. In FIG. 16A, the monocytes and PMNs were loaded with OVA using the protocols above and then subjected to FACs analysis for the OVA peptide. Both the monocytes and PMNs were able to load the antigen after a 1.5 hour incubation, but as shown in FIG. 16B the monocytes were significantly better than the PMNs at loading the peptide onto the cell surface. FIGS. 16C and 16D surprisingly demonstrated that the antigen-loaded PMN vaccination stimulated a higher percentage of tetramers and OVA specific CD8+ T cells than the antigen-loaded monocytes although these percentages were not statistically different.

Figure 17:
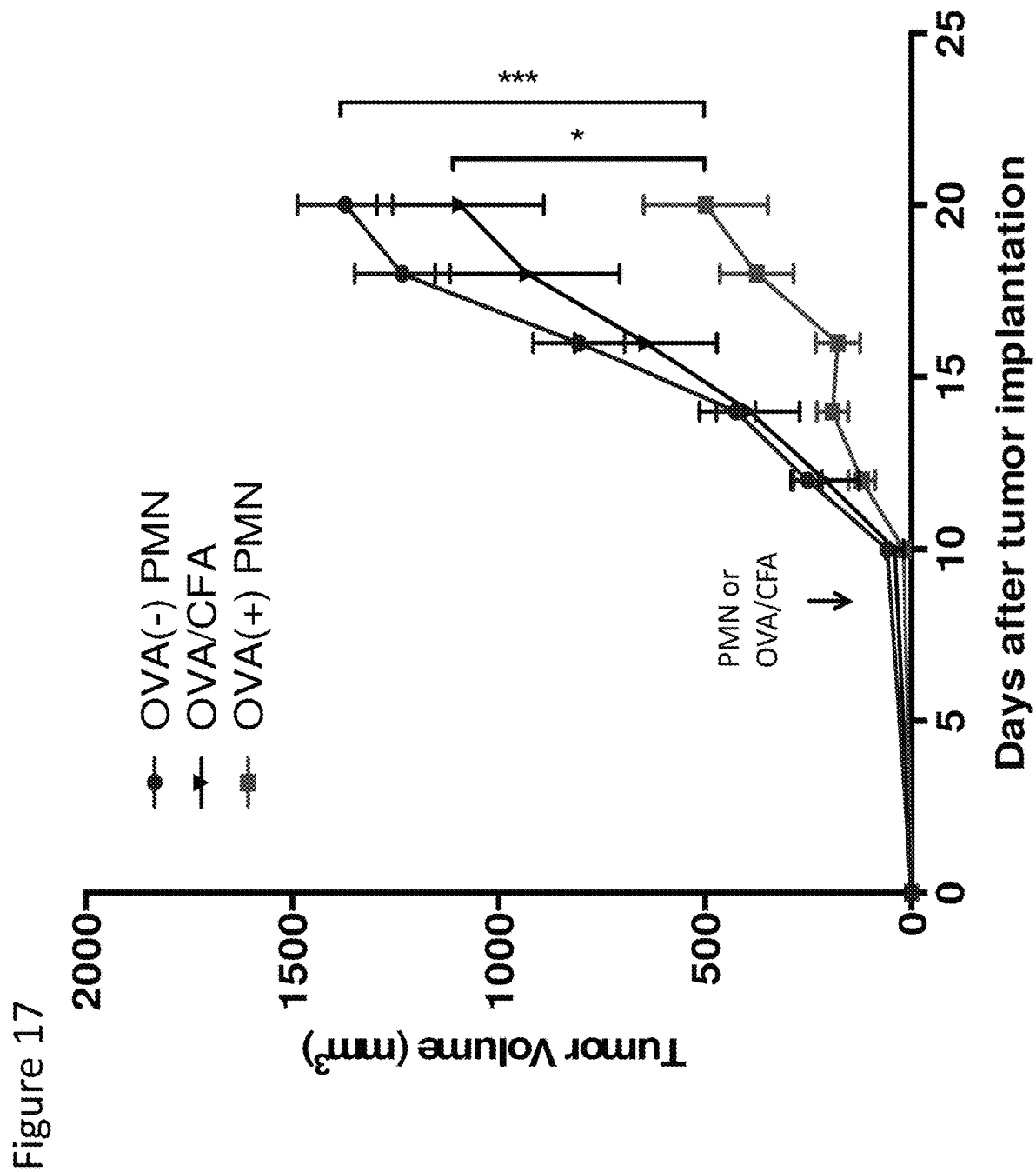
FIG. 17 is a graph showing that antigen-loaded neutrophils are capable of reducing tumor volume in a mouse model better that OVA-CFA.

Finally, mice were again injected in the flank with the B16-OVA cells at day 0 and subsequently immunized with PMNs, antigen loaded PMNS (OVA (+) PMN) or OVA-CFA and tumor volume was followed over time. As shown in FIG. 17, the OVA-loaded PMNs were able to significantly reduce tumor volume as compared to PMN not loaded with the antigen and in comparison to OVA-CFA. * P<0.05; *** P<0.001, Student's t test.

We claim:

1. A method of generating a cellular vaccine composition comprising:
    (a) isolating a population of cells comprising monocyte cells from a sample from a subject using negative selection for CD14, wherein less than 5% of the cells in the population of cells are dendritic cells, and wherein at least 50% of the cells in the population of cells are monocytes, wherein the monocytes are CD14+ and CCR7−;
    (b) contacting the population of cells from step (a) with at least one antigenic polypeptide or at least one polynucleotide encoding the at least one antigenic polypeptide, wherein the antigenic polypeptide comprises an isocitrate dehydrogenase 1 polypeptide or a tyrosinase-related protein 2 polypeptide; and
    (c) harvesting the population of cells of step (b), thereby generating a harvested population of cells, wherein less than 5% of the cells in the harvested population of cells are dendritic cells, wherein at least 70% of the cells in the harvested population of cells are monocytes, wherein the monocytes are CD14+, CD1−, CD83−, and CCR7−, suspending the population of cells in a pharmaceutically acceptable carrier, wherein the cells are suspended in a single dose formulation comprising a therapeutically effective amount, wherein the therapeutically effective amount is about 10-fold less than a therapeutically effective amount of antigen loaded lymphocytes, whole blood cells, or total splenocytes, to prepare the cellular vaccine composition.

2. The method of claim 1, wherein the sample is a peripheral blood sample from the subject.

3. The method of claim 1, wherein step (c) comprises washing the population of cells.

4. The method of claim 1, wherein at least 80% of the cells in the cellular vaccine composition population of cells are monocytes.

5. The method of claim 1, wherein the contacting step is for at least 30 minutes and is for no more than 24 hours.

6. The method of claim 1, wherein contacting in step (b) comprises electroporation, transfection or transformation of the population of cells with a nucleic acid encoding the antigenic polypeptide.

7. The method of claim 1, wherein contacting in step (b) comprises contacting the population of cells from step (a) with at least one polynucleotide encoding the at least one antigenic polypeptide, wherein the at least one polynucleotide is an RNA.

8. The method of claim 1, wherein the antigenic polypeptide comprises or consists of mIDH1 of SEQ ID NO: 5 or TRP2$_{(180\text{-}188)}$ of SEQ ID NO: 6.

9. The method of claim 1, wherein less than 5% of the cells in the harvested population of cells isolated in step (a) are antigen presenting cells (APCs).

10. The method of claim 1, wherein the method further comprises administering an effective amount of the cellular vaccine composition to a subject in need thereof to elicit an antigen-specific immune response in the subject.

11. The method of claim 1, wherein isolating comprises subjecting the sample from the subject to elutriation.

12. The method of claim 11, wherein isolating comprises subjecting the sample from the subject to elutriation with a cell separator.

13. The method of claim 1, wherein isolating comprises subjecting the sample from the subject to density gradient centrifugation.

14. The method of claim 1, wherein isolating comprises depleting cells expressing CD3, CD4, CD8, CD11c, CD19, B220, CD1, CD83 and/or CCR7 from the sample from the subject.

15. The method of claim 14, wherein isolating comprises depleting cells expressing CD3 and CD19 from the sample from the subject.

16. The method of claim 10, wherein administering comprises administering at least 4×10^6 cells to the subject.

17. The method of claim 10, wherein the subject has been diagnosed with a cancer.

\* \* \* \* \*

SEQUENCE LISTING

<160> NUMBER OF SEQ ID NOS: 7

<210> SEQ ID NO 1
<211> LENGTH: 21
<212> TYPE: DNA
<213> ORGANISM: Artificial Sequence
<220> FEATURE:
<223> OTHER INFORMATION: Synthetic: Gja1-forward

<400> SEQUENCE: 1

```
acttcagcct ccaaggagtt c                                            21

<210> SEQ ID NO 2
<211> LENGTH: 21
<212> TYPE: DNA
<213> ORGANISM: Artificial Sequence
<220> FEATURE:
<223> OTHER INFORMATION: Synthetic: Gja1-reverse

<400> SEQUENCE: 2
ggagtaggct tggaccttgt c                                            21

<210> SEQ ID NO 3
<211> LENGTH: 19
<212> TYPE: DNA
<213> ORGANISM: Artificial Sequence
<220> FEATURE:
<223> OTHER INFORMATION: Synthetic: Rpl32-forward

<400> SEQUENCE: 3
aagcgaaact ggcggaaac                                               19

<210> SEQ ID NO 4
<211> LENGTH: 20
<212> TYPE: DNA
<213> ORGANISM: Artificial Sequence
<220> FEATURE:
<223> OTHER INFORMATION: Synthetic: Rpl32-reverse

<400> SEQUENCE: 4
taaccgatgt tgggcatcag                                              20

<210> SEQ ID NO 5
<211> LENGTH: 25
<212> TYPE: PRT
<213> ORGANISM: Artificial Sequence
<220> FEATURE:
<223> OTHER INFORMATION: Synthetic: mutant IDH1-R132H 25-mer

<400> SEQUENCE: 5

Gly Trp Val Lys Pro Ile Ile Ile Gly His His Ala Tyr Gly Asp Gln
1               5                   10                  15

Tyr Arg Ala Thr Asp Phe Val Val Pro
            20                  25

<210> SEQ ID NO 6
<211> LENGTH: 9
<212> TYPE: PRT
<213> ORGANISM: Artificial Sequence
<220> FEATURE:
<223> OTHER INFORMATION: Synthetic: TRP2180-188

<400> SEQUENCE: 6

Ser Val Tyr Asp Phe Phe Val Trp Leu
1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic: OVA323-339
```

```
<400> SEQUENCE: 7

Ile Ser Gln Ala Val His Ala Ala His Ala Glu Ile Asn Glu Ala Gly
1               5                   10                  15
Arg
```